US012611378B2

(12) United States Patent
Cole et al.

(10) Patent No.: US 12,611,378 B2
(45) Date of Patent: Apr. 28, 2026

(54) TARGETED RELEASE RIFAXIMIN COMPOSITIONS

(71) Applicant: Bausch Health Ireland Limited, Dublin (IE)

(72) Inventors: Jacob Cole, Fairport, NY (US); Brian R. Rohrs, Fairport, NY (US); Daniel J. Stein, Rochester, NY (US); Robert J. Israel, Suffern, NY (US); Ezra R. Lowe, Bridgewater, NJ (US)

(73) Assignee: Bausch Health Ireland Limited, Dublin (IE)

( * ) Notice: Subject to any disclaimer, the term of this patent is extended or adjusted under 35 U.S.C. 154(b) by 58 days.

(21) Appl. No.: 18/012,362

(22) PCT Filed: Jun. 25, 2021

(86) PCT No.: PCT/EP2021/067583

§ 371 (c)(1),
(2) Date: Dec. 22, 2022

(87) PCT Pub. No.: WO2021/260211

PCT Pub. Date: Dec. 30, 2021

(65) Prior Publication Data

US 2023/0277447 A1 Sep. 7, 2023

Related U.S. Application Data

(60) Provisional application No. 63/190,349, filed on May 19, 2021, provisional application No. 63/107,400, filed on Oct. 29, 2020, provisional application No. 63/044,450, filed on Jun. 26, 2020.

(51) Int. Cl.

| | |
|---|---|
| ***A61K 9/00*** | (2006.01) |
| ***A61K 31/137*** | (2006.01) |
| ***A61K 31/437*** | (2006.01) |
| ***A61K 31/4468*** | (2006.01) |
| ***A61K 31/485*** | (2006.01) |
| ***A61K 45/06*** | (2006.01) |
| ***A61K 47/10*** | (2017.01) |
| ***A61K 47/14*** | (2017.01) |
| ***A61K 47/32*** | (2006.01) |
| ***A61K 47/38*** | (2006.01) |
| ***A61P 7/00*** | (2006.01) |
| ***A61P 7/04*** | (2006.01) |

(52) U.S. Cl.

CPC .......... *A61K 9/0056* (2013.01); *A61K 31/137* (2013.01); *A61K 31/437* (2013.01); *A61K 31/4468* (2013.01); *A61K 31/485* (2013.01); *A61K 45/06* (2013.01); *A61K 47/10* (2013.01); *A61K 47/14* (2013.01); *A61K 47/32* (2013.01); *A61K 47/38* (2013.01); *A61P 7/00* (2018.01); *A61P 7/04* (2018.01)

(58) Field of Classification Search

CPC ...... A61K 9/0056; A61K 47/10; A61K 47/32; A61K 47/38; A61K 9/5026; A61K 9/5078; A61K 9/5084; A61K 9/1676; A61P 7/00; A61P 7/04; A61P 1/00; A61P 7/06; A61P 9/10; A61P 25/16; A61P 25/28; A61P 35/02

See application file for complete search history.

(56) References Cited

U.S. PATENT DOCUMENTS

| | | | | |
|---|---|---|---|---|
| 4,341,785 | A | 7/1982 | Marchi et al. | |
| 4,557,866 | A | 12/1985 | Cannata et al. | |
| 4,717,569 | A | 1/1988 | Harrison et al. | |
| 6,352,720 | B1 | 3/2002 | Martin et al. | |
| 6,861,053 | B1 | 3/2005 | Lin et al. | |
| 7,045,620 | B2 | 5/2006 | Viscomi et al. | |
| 7,612,199 | B2 | 11/2009 | Viscomi et al. | |
| 7,902,206 | B2 | 3/2011 | Viscomi et al. | |
| 7,906,542 | B2 | 3/2011 | Viscomi et al. | |
| 7,915,275 | B2 | 3/2011 | Viscomi et al. | |
| 7,928,115 | B2 | 4/2011 | Forbes et al. | |
| 8,158,644 | B2 | 4/2012 | Viscomi et al. | |
| 8,158,781 | B2 | 4/2012 | Viscomi et al. | |
| 8,193,196 | B2 | 6/2012 | Viscomi et al. | |
| 8,309,569 | B2 | 11/2012 | Forbes et al. | |
| 8,383,151 | B2 * | 2/2013 | Kulkarni et al. | .... A61K 9/1652 424/464 |
| 8,518,949 | B2 | 8/2013 | Viscomi et al. | |
| 8,568,782 | B2 | 10/2013 | Viscomi et al. | |
| 8,617,598 | B2 | 12/2013 | Haeberlin et al. | |
| 8,741,904 | B2 | 6/2014 | Viscomi et al. | |

(Continued)

FOREIGN PATENT DOCUMENTS

| | | | |
|---|---|---|---|
| AU | 2014202520 | A1 | 5/2014 |
| CN | 101137350 | A | 3/2008 |

(Continued)

OTHER PUBLICATIONS

U.S. Appl. No. 13/181,481, filed Jul. 12, 2011, 2012/0077835.
U.S. Appl. No. 14/250,293, filed Apr. 10, 2014, U.S. Pat. No. 9,737,610.
U.S. Appl. No. 15/281,543, filed Sep. 30, 2016, 2017/0087134.
U.S. Appl. No. 15/615,121, filed Jun. 6, 2017, 2017/0333562.
U.S. Appl. No. 16/916,421, filed Jun. 30, 2020, 2020/0397904.
U.S. Appl. No. 16/369,509, filed Mar. 29, 2019, U.S. Pat. No. 10,874,647.
U.S. Appl. No. 17/101,609, filed Nov. 23, 2020.
U.S. Appl. No. 17/174,829, filed Feb. 12, 2021, U.S. Pat. No. 11,129,817.

(Continued)

*Primary Examiner* — Robert A Wax
*Assistant Examiner* — John Seungjai Kwon
(74) *Attorney, Agent, or Firm* — Morgan, Lewis & Bockius LLP

(57) ABSTRACT

Provided herein are GI specific rifaximin release compositions which can be formulated for targeted delivery of rifaximin to one or more portions of the GI tract. Methods of treating diseases and disorders with the disclosed compositions are also provided.

6 Claims, 4 Drawing Sheets

(56) References Cited

U.S. PATENT DOCUMENTS

| | | | | |
|---|---|---|---|---|
| 8,835,452 | B2 | 9/2014 | Viscomi et al. | |
| 8,853,231 | B2 | 10/2014 | Viscomi et al. | |
| 9,271,968 | B2 | 3/2016 | Viscomi et al. | |
| 9,737,610 | B2 | 8/2017 | Selbo et al. | |
| 10,874,647 | B2 | 12/2020 | Golden et al. | |
| 11,129,817 | B2 | 9/2021 | Golden et al. | |
| 11,311,521 | B2 | 4/2022 | Golden et al. | |
| 11,779,571 | B2 | 10/2023 | Forbes et al. | |
| 2004/0138231 | A1 | 7/2004 | Bateman et al. | |
| 2005/0101598 | A1 | 5/2005 | Viscomi et al. | |
| 2007/0141143 | A1 | 6/2007 | Smithey et al. | |
| 2007/0218138 | A1 | 9/2007 | Bittorf et al. | |
| 2008/0095754 | A1 | 4/2008 | Burke et al. | |
| 2009/0011020 | A1 | 1/2009 | Viscomi et al. | |
| 2009/0011024 | A1 | 1/2009 | Babcock et al. | |
| 2009/0028940 | A1 | 1/2009 | Jahagirdar et al. | |
| 2009/0124670 | A1 | 5/2009 | Sakai | |
| 2010/0174064 | A1 | 7/2010 | Gushurst et al. | |
| 2011/0118295 | A1 | 5/2011 | Forbes et al. | |
| 2011/0312973 | A1 | 12/2011 | Liepold et al. | |
| 2012/0077835 | A1 | 3/2012 | Selbo et al. | |
| 2012/0214833 | A1 | 8/2012 | Kulkarni et al. | |
| 2015/0164866 | A1 | 6/2015 | Randall | |
| 2017/0027975 | A1 | 2/2017 | Frieman et al. | |
| 2017/0087134 | A1 * | 3/2017 | Golden | A61K 31/439 |
| 2017/0333562 | A1 | 11/2017 | Selbo et al. | |
| 2018/0021297 | A1 | 1/2018 | Hauser | |
| 2019/0224175 | A1 | 7/2019 | Golden et al. | |
| 2020/0397904 | A1 | 12/2020 | Selbo et al. | |
| 2022/0040157 | A1 | 2/2022 | Golden et al. | |
| 2022/0378758 | A1 | 12/2022 | Angel et al. | |
| 2023/0027192 | A1 | 1/2023 | Bajaj | |

FOREIGN PATENT DOCUMENTS

| | | | | |
|---|---|---|---|---|
| CN | 101502513 | A | 8/2009 | |
| CN | 102716168 | A | 10/2012 | |
| CN | 103118666 | A | 5/2013 | |
| CN | 103263668 | A | 8/2013 | |
| CN | 103340856 | A | 10/2013 | |
| CN | 105025717 | A | 11/2015 | |
| CN | 107281210 | A | 10/2017 | |
| CN | 110290781 | A | 9/2019 | |
| EP | 2011486 | A1 | 1/2009 | |
| EP | 2542225 | A2 | 1/2013 | |
| EP | 1996710 | B1 | 8/2019 | |
| JP | 2002537317 | A | 11/2022 | |
| KR | 20130098300 | A | 9/2013 | |
| KR | 20130106400 | A | 9/2013 | |
| MX | 2012004954 | A | 9/2012 | |
| NZ | 231622 | A | 5/1991 | |
| RU | 2609833 | C2 | 2/2017 | |
| WO | WO-2002/051385 | A1 | 7/2002 | |
| WO | 03/101445 | A1 | 12/2003 | |
| WO | 2003101445 | A1 | 12/2003 | |
| WO | 200473692 | A1 | 9/2004 | |
| WO | 2005030142 | A2 | 4/2005 | |
| WO | 2005044823 | A2 | 5/2005 | |
| WO | WO-2006/026500 | A1 | 3/2006 | |
| WO | 2006094662 | A1 | 9/2006 | |
| WO | WO-2006/094737 | A2 | 9/2006 | |
| WO | 2007117556 | A2 | 10/2007 | |
| WO | WO-2009/008005 | A1 | 1/2009 | |
| WO | WO-2009/108730 | A2 | 9/2009 | |
| WO | WO-2009/118167 | A1 | 10/2009 | |
| WO | 2010044093 | A1 | 4/2010 | |
| WO | WO-2010/040020 | A1 | 4/2010 | |
| WO | WO-2010/067072 | A1 | 6/2010 | |
| WO | WO-2011/051971 | A2 | 5/2011 | |
| WO | WO-2011/061748 | A1 | 5/2011 | |
| WO | WO-2012/009387 | A1 | 1/2012 | |
| WO | WO-2012/009388 | A1 | 1/2012 | |
| WO | 2012035283 | A1 | 3/2012 | |
| WO | 2012103119 | A1 | 8/2012 | |
| WO | 2006112541 | A1 | 7/2013 | |
| WO | 2014006576 | A1 | 1/2014 | |
| WO | 2016014437 | A1 | 1/2016 | |
| WO | WO-2016/063289 | A2 | 4/2016 | |
| WO | WO-2016/178652 | A1 | 11/2016 | |
| WO | WO-2018/064472 | A1 | 4/2018 | |
| WO | WO-2018165404 | A1 * | 9/2018 | A61K 31/05 |
| WO | WO-2019/178652 | A1 | 9/2019 | |
| WO | WO-2020/047311 | A1 | 3/2020 | |
| WO | WO-2020/198136 | A1 | 10/2020 | |
| WO | WO-2021/108360 | A1 | 6/2021 | |

OTHER PUBLICATIONS

U.S. Appl. No. 17/468,457, filed Sep. 7, 2021, U.S. Pat. No. 11,311,521.

U.S. Appl. No. 17/468,461, filed Sep. 7, 2021, 2022/0040157.

U.S. Appl. No. 17/779,865, filed May 25, 2022, Pending.

U.S. Appl. No. 17/913,844, filed Sep. 23, 2022, Pending.

U.S. Appl. No. 17/913,843, filed Sep. 23, 2022, Pending.

U.S. Appl. No. 17/918,374, filed Oct. 12, 2022, Pending.

Office Action issued in European Patent Application No. 21739302.4, dated Jun. 13, 2024, 11 pages.

Scarpignato et al., "Impact of crystal polymorphism on the systemic bioavailability of rifaximin, an antibiotic acting locally in the gastrointestinal tract, in healthy volunteers," Drug Design, Development, and Therapy, 2014, pp. 1-10.

Siepmann et al., "Polymer Blends for Controlled Release Coatings," Journal of Controlled Release, 2008, 125:1-15.

Office Action issued in Chinese Patent Application No. 202180052294.0, dated Mar. 27, 2024, 30 pages.

Office Action issued in Eurasian Patent Application No. 202390175, dated Sep. 25, 2023, 12 pages.

Omez® DSR Label (LP-003998-061216. Dec. 6, 2016). State Register of Medicines [online] [retrieved Aug. 31, 2023]. Found on <https://grls.rosminzdrav.ru/InstrImg/2016/12/13/1413974/%D0%9B%D0%9F- 003998[2016]_0.pdf>, 27 pages.

International Search Report and Written Opinion issued in PCT/EP2021/067583, dated Sep. 29, 2021, 12 pages.

Acosta et al., Effects of Rifaximin on Transit, Permeability, Fecal Microbiome, and Organic Acid Excretion in Irritable Bowel Syndrome. Clin Transl Gastroenterol. May 26, 2016;7(5) :e173, 11 pages.

Bacchi et al., Polymorphism-structure relationships of rifamexil, an antibiotic rifamycin derivative. Mol Pharmacol. 1995;47(3):611-623.

Bajaj et al., Investigational Water-soluble Rifaximin Formulation Significantly Shortens Time to Recovery in Hospitalized Patients with Overt Hepatic Encephalopathy (OHE): A Phase 2, Randomized, Double-blind, Placebo-controlled Trial. Hepatology. 2020;72(1):57A-58A, Abstract 75.

Bajaj et al., Lactulose Withdrawal Can Potentiate Breakthrough Overt Hepatic Encephalopathy in Patients Controlled wtih Rifaximin Plus Lactulose Therapy: A Post Hoc Analysis of a Randomized Controlled Trial. Crohn's and Colitis Congress. Jan. 23-25, 2020;158(6) Suppl. 1:S1455-S1456, Abstract Tu1693.

Bajaj et al., Oral Rifaximin Soluble Solid Dispersion Immediate-release 40 mg Prevents Development of Cirrhosis-related Complications: a Phase 2, Randomized, Multicenter, Double-blind, Placebo-controlled Trial. Hepatology, 2016;64(1):1027A, Abstract 2064.

Bajaj et al., Rifaximin and Lactulose Combination Therapy Versus Lactulose Alone for Prevention of Overt Hepatic Encephalopathy Recurrence: A Pooled Analysis of Two Randomized Trials. Gastroenterology. 2019;156:S560, Abstract Su1519.

Bajaj, Review article: potential mechanisms of action of rifaximin in the management of hepatic encephalopathy and other complications of cirrhosis. Aliment Pharmacol Ther. Jan. 2016;43 Suppl 1:11-26.

Bavin, Polymorphism in process development. Chemistry & Industry. Aug. 2, 19891;16:527-529.

Blandizzi et al., Impact of crystal polymorphism on the systemic bioavailability of rifaximin, an antibiotic acting locally in the gastrointestinal tract, in healthy volunteers. Drug Des Devel Ther. Dec. 16, 2014;9:1-11.

(56) References Cited

OTHER PUBLICATIONS

Boulware, Travel medicine for the extreme traveler. Dis Mon. 2006;52(8):309-325.
Buhler, Polyvinylpyrrolidone Excipients for Pharmaceuticals, Povidone, Crospovidone and Copovidone. Springer, Chapter 2, Section 2.4.3, pp. 83-98, 2005.
Byrn et al., Hydrates and Solvates. Solid-State Chemistry of Drugs, Second Edition. SSCI, Inc., Chapter 11, pp. 233-247, (1999).
Byrn et al., Pharmaceutical solids: a strategic approach to regulatory considerations. Pharm Res. 1995;12(7):945-954.
Castelli et al., Epidemiology of travelers' diarrhea. J Travel Med. 2001;8(Suppl 2):S26-S30.
Cheng et al., Update on Traveler's Diarrhea. Curr Infect Dis Rep. 2002;4(1):70-77.
ClinicalTrials.gov, Rifaximin Versus Placebo in the Prevention of Travelers' Diarrhea. Identifier: NCT00098384, 6 pages, May 9, 2006.
ClinicalTrials.gov, Rifaximin, Loperamide and the Combination to Treat Travelers' Diarrhea. Identifier: NCT00292344, 6 pages, Apr. 20, 2009.
Crum et al., New issues in infectious diarrhea. Rev Gastroenterol Disord. 2005;5 Suppl 3:S16-S25.
Datta et al., Crystal structures of drugs: advances in determination, prediction and engineering. Nat Rev Drug Discov. 2004;3(1):42-57.
Dupont et al., A randomized, double-blind, placebo-controlled trial of rifaximin to prevent travelers' diarrhea. Ann Intern Med. 2005;142(10):805-812.
Dupont et al., Rifaximin versus ciprofloxacin for the treatment of traveler's diarrhea: a randomized, double-blind clinical trial. Clin Infect Dis. 2001;33(11):1807-1815.
Dupont et al., Treatment of travelers' diarrhea: randomized trial comparing rifaximin, rifaximin plus loperamide, and loperamide alone. Clin Gastroenterol Hepatol. 2007;5(4):451-456.
Dupont, Treatment of travelers' diarrhea. J Travel Med. 2001;8(Suppl 2):S31-S33.
Dutta et al., Effects of rifaximin on circulating aged neutrophils in sickle cell disease. Am J Hematol. Jun. 2019;94(6):E175-E176.
Dutta et al., Rifaximin on intestinally-related pathologic changes in sickle cell disease. Am J Hematol. Apr. 2020;95(4):E83-E86.
Emea, ICH Topic Q 6 A, Specifications: Test Procedures and Acceptance Criteria for New Drug Substances and New Drug Products: Chemical Substances. European Medicines Agency, CPMP/ICH/367/96. 32 pages, May 2000.
Ericsson, Rifaximin: a new approach to the treatment of travelers' diarrhea. Introduction. J Travel Med. 2001;8(Suppl 2):S25-S26.
Evonik Industries, EUDRAGIT® Acrylic Drug Delivery Polymers. Retrieved online at: http://eudragit.evonik.com/product/eudragit/en/products-services/eudragit-products/pages/default.aspx>> published on Apr. 23, 2010 as per Wayback Machine. 1 page.
FDA, Guideline for Submitting Supporting Documentation in Drug Applications for the Manufacture of Drug Substances. Center for Drug Evaluation and Research, Food and Drug Administration, Department of Health and Human Services. 47 pages, Feb. 1987.
Fiorucci et al., Inhibition of intestinal bacterial translocation with rifaximin modulates lamina propria monocytic cells reactivity and protects against inflammation in a rodent model of colitis. Digestion. 2002;66(4):246-256.
Gbinigie et al., Should azithromycin be used to treat COVID-19? A rapid review. BJGP Open. Jun. 23, 2020;4(2):1-8.
Gerard et al., Rifaximin: a nonabsorbable rifamycin antibiotic for use in nonsystemic gastrointestinal infections. Expert Rev Anti Infect Ther. 2005;3(2):201-211.
Ghoshal et al., Models for prediction of mortality from cirrhosis with special reference to artificial neural network: a critical review. Hepatol Int. 2008;2(1):31-38.
Gillis et al., Rifaximin. A review of its antibacterial activity, pharmacokinetic properties and therapeutic potential in conditions mediated by gastrointestinal bacteria. Drugs. 1995;49(3):467-484.
Gionchetti et al., Rifaximin in patients with moderate or severe ulcerative colitis refractory to steroid-treatment: a double-blind, placebo-controlled trial. Dig Dis Sci. 1999;44(6):1220-1221.
Guillory, Generation of Polymorphs, Hydrates, Solvates, and Amorphous Solids. Materials Science. Chapter 5, pp. 183-226, (1999).
Hancock et al., Characteristics and significance of the amorphous state in pharmaceutical systems. J Pharm Sci. Jan. 1997;86(1):1-12.
Huang et al., Rifaximin—a novel antimicrobial for enteric infections. J Infect. 2005;50(2):97-106.
Infante et al., Enteroaggregative *Escherichia coli* diarrhea in travelers: response to rifaximin therapy. Clin Gastroenterol Hepatol. 2004;2(2):135-138.
Jozwiakowski, Alteration of the Solid State of the Drug Substance: Polymorphs, Solvates, and Amorphous Forms. Water-Insoluble Drug Formulation. Ron Liu (Ed.), Taylor & Francis Group. Chapter 15, pp. 525-568, (2000).
Kakiyama et al., Modulation of the fecal bile acid profile by gut microbiota in cirrhosis. J Hepatol. May 2013;58(5):949-55.
Kalambokis et al., Rifaximin for the prevention of spontaneous bacterial peritonitis. World J Gastroenterol. Apr. 14, 2012;18(14):1700-1702.
Kalhor et al., Repurposing of the approved small molecule drugs in order to inhibit SARS-CoV-2 S protein and human ACE2 interaction through virtual screening approaches. J Biomol Struct Dyn. Feb. 2022;40(3):1299-1315.
Kalil et al., Treating COVID-19-Off-Label Drug Use, Compassionate Use, and Randomized Clinical Trials During Pandemics. JAMA. May 19, 2020;323(19):1897-1898.
Kallai et al., Evaluation of drug release from coated pellets based on isomalt, sugar, and microcrystalline cellulose inert cores. AAPS PharmSciTech. Mar. 2010;11(1):383-91.
Khankari et al., Pharmaceutical hydrates. Thermochimica Acta. 1995;248:61-79.
Koo et al., Current and future developments in travelers' diarrhea therapy. Expert Rev Anti Infect Ther. 2006;4(3):417-427.
Koo et al., The role of rifaximin in the treatment and chemoprophylaxis of travelers' diarrhea. Ther Clin Risk Manag. 2009;5:841-848.
Leuner et al., Improve Drug Solubility for Oral Delivery using Solid Dispersions. European Journal of Pharmaceutics and Biopharmaceutics. 2000;50:47-60.
Lim et al., Clinicopathologic consequences following discontinuation of rifaximin in patients with sickle cell disease. Am J Hematol. Jun. 2020;95(6):E151-E153.
Lim et al., Rifaximin for sickle cell disease. Am J Hematol. Dec. 2019;94(12):E325-E328.
Malamud et al., Treatment of gastrointestinal infections. Curr Opin Gastroenterol. 2000;16(1):51-55.
Martins, et al., Microstructured Ternary Solid Dispersions to Improve Carbamazepine Solubility. Powder Technology. Jan. 2012;215-216:156-165.
Mas et al., Comparison of rifaximin and lactitol in the treatment of acute hepatic encephalopathy: results of a randomized, double-blind, double-dummy, controlled clinical trial. J Hepatol. 2003;38(1):51-58.
Miglioli et al., Effects of daily oral administration of rifaximin and neomycin on faecal aerobic flora in rats. Pharmacol Res. 2001;44(5):373-375.
Neff et al., Analysis of hospitalizations comparing rifaximin versus lactulose in the management of hepatic encephalopathy. Transplant Proc. 2006;38(10):3552-3555.
New York Medical College. Rifaximin to Modify the Disease Course in Sickle Cell Disease. NCT03719729. Oct. 25, 2018, <https://clinicaltrials.gov/ct2/show/study/NCT03719729>.
Newman et al., Form Selection of Pharmaceutical Compounds. Handbook of Pharmaceutical Analysis. Lena Ohannesian (Ed.), Marcel Dekker, Inc., New York. Chapter 1, 61 pages, (2002).
Nguyenla et al., Discovery of SARS-CoV-2 antiviral synergy between remdesivir and approved drugs in human lung cells. bioRxiv, retrieved onilne at: https://www.biorxiv.org/content/10.1101/2020.09.18.302398v1.full.pdf. 32 pages, Sep. 18, 2020.
Paik et al., Comparison of rifaximin and lactulose for the treatment of hepatic encephalopathy: a prospective randomized study. Yonsei Med J. 2005;46(3):399-407.

(56) References Cited

OTHER PUBLICATIONS

Pakyz, Rifaximin: a new treatment for travelers' diarrhea. Ann Pharmacother. 2005;39(2):284-289.
Pawlowski et al., Diagnosis and treatment of acute or persistent diarrhea. Gastroenterology. 2009;136(6):1874-1886.
Pelizza et al., Polymorphism of rifampicin. Farmaco Sci. 1977;32(7):471-481.
Pigott, Foodborne illness. Emerg Med Clin North Am. 2008;26(2):475-497.
Preidis et al., Targeting the human microbiome with antibiotics, probiotics, and prebiotics: gastroenterology enters the metagenomics era. Gastroenterology. 2009;136(6):2015-2031.
Sahraei et al., Aminoquinolines against coronavirus disease 2019 (COVID-19): chloroquine or hydroxychloroquine. Int J Antimicrob Agents. Apr. 2020;55(4):105945.
Sanyal et al., Impact of Baseline Chronic Liver Disease Characteristics on the Efficacy of Oral Rifaximin Soluble Solid Dispersion Tablets for the Prevention of Further Decompensationor All-Cause Mortality in Patients With Cirrhosis and Ascites. Hepatology. 2016;64(1):47A, Abstract 86.
Scarpignato et al., Prevention and treatment of traveler's diarrhea: a clinical pharmacological approach. Chemotherapy. 1995;41 Suppl 1:48-81.
Scarpignato et al., Rifaximin, a poorly absorbed antibiotic: pharmacology and clinical potential. Chemotherapy. 2005;51 Suppl 1:36-66.
Solanki et al., Multiple Unit Dosage Forms: a Review. Pharmtechmedica. 2012;1(1):11-21.
Steffen et al., Therapy of travelers' diarrhea with rifaximin on various continents. Am J Gastroenterol. 2003;98(5):1073-1078.
Steffen, Rifaximin: a nonabsorbed antimicrobial as a new tool for treatment of travelers' diarrhea. J Travel Med. 2001;8(Suppl 2):S34-S39.
Su et al., Utility of the Nonabsorbed (<0.4%) Antibiotic Rifaximin in Gastroenterology and Hepatology. Gastroenterol Hepatol (N Y). 2006;2(3):186-197.
Taylor et al., A randomized, double-blind, multicenter study of rifaximin compared with placebo and with ciprofloxacin in the treatment of travelers' diarrhea. Am J Trop Med Hyg. 2006;74(6):1060-1066.
Taylor et al., Systemic pharmacokinetics of rifaximin in volunteers with shigellosis. Antimicrob Agents Chemother. 2008;52(3):1179-1181.
Trinh et al., Diarrheal diseases in the elderly. Clin Geriatr Med. 2007;23(4):833-856.
Van Den Mooter, Solid Dispersions as a Formulation Strategy for Poorly Soluble Compounds. 20th Annual Symposium of the Finish Society of Physical Pharmacy; Vithi, Finland; Katholieke Universiteit Leuven; 37 pages; Jan. 28-29, 2009.
Vasconcelos et al., Solid dispersions as strategy to improve oral bioavailability of poor water soluble drugs. Drug Discov Today. Dec. 2007;12(23-24):1068-75.
Vijayasekar, The Impact of COVID-19 Pandemic on Gastroenterology (GI) Outpatient Care: Pros and Cons of Telehealthcare. AMerican College of Gastroenterology. Retrieved online at: https://acgcasereports.gi.org/media/press-info-scientific-meeting/featured-science/p2542-the-impact-of-covid-19-pandemic-on-gastroenterology-gi-outpatient-care-pros-and-cons-of-telehealthcare/. 2 pages, Abstract P2542, Oct. 26, 2020.
Vippagunta et al., Crystalline solids. Adv Drug Deliv Rev. 2001;48(1):3-26.
Viscomi et al., Crystal forms of rifaximin and their effect on pharmaceutical properties. CrystEngComm. 2008;10:1074-1081.
Visser et al., Inulin solid dispersion technology to improve the absorption of the BCS Class IV drug TMC240. Eur J Pharm Biopharm. Feb. 2010;74(2):233-8.
Vlachogiannakos et al., Long-term administration of rifaximin improves the prognosis of patients with decompensated alcoholic cirrhosis. J Gastroenterol Hepatol. Mar. 2013;28(3):450-5.
Wagner et al., Travellers' diarrhoea—pros and cons of different prophylactic measures. Wien Klin Wochenschr. Oct. 2009;121 Suppl 3:13-8.
Williams et al., Rifaximin, a nonabsorbed oral antibiotic, in the treatment of hepatic encephalopathy: antimicrobial activity, efficacy, and safety. Rev Gastroenterol Disord. 2005;5 Suppl 1:S10-S18.
Xifaxan (rifaximin) Tablets, NDA 21-361/S-006. www.salix.com, 16 pages, (2006).
Xifaxan (rifaximin) Tablets, Revised Xifaxan Label. www.salix.com, 13 pages, May 21, 2004.
Declaration Under 37 C.F. R. Sec. 1.132 for U.S. Pat. No. 10,728,090.
Polymorph forms of rifaximin, processes for their production and use thereof in medicinal preparations. Viscomi. 12 pages, Jan. 10, 2006.
Decision to Grant issued in Russian Patent Application No. 2022110800, dated Jul. 1, 2024, 25 pages.
Decision on Rejection issued in Chinese Patent Application No. 202080067056.2, dated Sep. 9, 2024, 21 pages.
Office Action issued in Chinese Patent Application No. 202080067056.2, dated Apr. 26, 2024, 21 pages.
Office Action issued in European Patent Application No. 19163419.5, dated Mar. 13, 2024, 6 pages.
Office Action issued in European Patent Application No. 20785690.7, dated Apr. 17, 2024, 7 pages.
Office Action issued in U.S. Appl. No. 18/628,353, dated Aug. 22, 2024, 14 pages.
Office Action issued in U.S. Appl. No. 18/628,366, dated Sep. 17, 2024, 16 pages.
Office Action issued in Brazilian Patent Application No. 112022003500-4, dated Aug. 27, 2024, 5 pages.
Sharara et al., A Randomized Double-Blind Placebo-Controlled Trial of Rifaximin in Patients with Abdominal Bloating and Flatulence, Am J Gastroenterol, 101:326-333, 2006.
Marchina et al., Infectious diarrhea in the aged: controlled clinical trial of Rifaximin, Chemioterapia, 7(5):336-40, 1988.
Kornbluth Asher: "Efficacy and Safety of Open Label Rifaximin in the Treatment of Mild-Moderate Crohn's Disease (CD) Refractory to Multiple Medical Therapies", American College of Gastroenterology, vol. 111, Sep. 1, 2006, p. S449, XP93138081.
Kornbluth Asher et al: "Efficacy and Safety of Rifaximin in the Treatment of Mild-Moderate Crohn's Disease: Results of An Ope••Label Pilot Study", Gastroenterology, vol. 128, No. 4 Suppl 2, Apr. 1, 2005, pp. A-579, XP93138544.
Prantera et al: "Antibiotic treatment of Crohn's disease: results of a multicentre, double blind, randomized, placebo. controlled trial with rifaximin", Alimentary Pharmacology & Therapeutics, Blackwell Scientific Publications Ltd., Cambridge, GB, vol. 23, No. 8, Mar. 30, 2006, pp. 1117-1125, XP071540572.
Lu Bin, People's Health Publishing House, New Techniques and New Dosage Forms of Drugs, 2nd version in Jul. 2005, date of publication: May 31, 2005, pp. 51-53.
Office Action issued in Japanese Patent Application No. 2022-518665, mailed Oct. 1, 2024, 9 pages.
Arya, et al., "Rifaximin the promising anti-microbial for enteric infections", Journal of Infection, Academic Press, Loondon, GB, (Oct. 1, 2005), vol. 51, No. 3, p. 262.
Office Action issued in Mexican Patent Application No. MX/a/2022/003481, dated Oct. 18, 2024, 12 pages.
Office Action issued in corresponding Chinese Application No. 202180052294.0, dated Nov. 6, 2024, 18 pages.
Decision on Rejection issued in Chinese Patent Application No. 202180052294.0, dated Apr. 7, 2025, 31 pages.
Office Action issued in U.S. Appl. No. 18/012,362, dated Feb. 12, 2025, 12 pages.
Office Action issued in Mexican Patent Application No. MX/a/2022/003481, dated Apr. 22, 2025, 12 pages.
Office Action issued in U.S. Appl. No. 17/779,865, dated Mar. 13, 2025, 25 pages.
Hughes, J.P., Rees, S., Kalindjian, S.B., Philpott, K.L., Principles of early drug discovery, British Journal of Pharmacology, 162, p. 1239-1249 (Year: 2011).

(56) References Cited

OTHER PUBLICATIONS

Li, T. and Chiang, J.Y.L., Bile Acid Signaling in Metabolic Disease and Drug Therapy, Pharmacological Reviews, 66, p. 948-983 (Year: 2014).
Calanni, F., Renzulli, C., Barbanti, M, and Viscomi, G.C., Rifaximin: beyond the traditional antibiotic acitivty, The Journal of Antibiotics, 67, p. 667-670 (Year: 2014).
Shayto, R. H, Mrad, R.A., and Sharara, A.I., Use of rifaximin in gastrointestinal and liver diseases, World Journal of Gastroenterology, 22, p. 6638-6651 (Year: 2016).
Cosmetic Ingredient Information Online "PEG-60 Hydrogenated Castor Oil," https://cosmetic-ingredients.org/surfactants-emulsifying-agents/2066/.
Office Action issued in Japanese Patent Application No. 2022-518665, dated Apr. 1, 2025, 9 pages.
Office Action issued in Eurasian Patent Application No. 202390175, dated May 22, 2025, 25 pages.
Office Action issued in Japanese Patent Application No. 2022-580309, mailed Jul. 15, 2025, 7 pages.
Office Action issued in Canadian Patent Application. No. 3,151,010, dated Sep. 5, 2025, 3 pages.
Office Action issued in Australian Patent Application No. 2020355603, dated Aug. 22, 2025, 4 pages.
Office Action issued in U.S. Appl. No. 17/779,865, dated Sep. 19, 2025, 12 pages.

* cited by examiner

TARGETED RELEASE RIFAXIMIN COMPOSITIONS

CROSS-REFERENCE TO RELATED APPLICATIONS

This application is a 35 U.S.C. § 371 national stage filing of International Application No. PCT/EP2021/067583, filed on Jun. 25, 2021, which claims the benefit of priority to U.S. Provisional Application No. 63/044,450, filed Jun. 26, 2020, U.S. Provisional Application No. 63/107,400, filed Oct. 29, 2020, and U.S. Provisional Application No. 63/190,349, filed May 19, 2021, the entire contents of each of which are incorporated herein by reference.

BACKGROUND

Rifaximin is an orally available broad spectrum antibiotic with antimicrobial activity against Gram-positive and Gram-negative aerobic and anaerobic bacteria. Rifaximin is currently indicated for the treatment of traveler's diarrhea (TD), for maintaining remission of hepatic encephalopathy (HE), and for treating irritable bowel syndrome with diarrhea (IBS-D). Other uses for rifaximin include e.g., treating *C. difficile* infections, infectious diarrhea, small intestinal bacterial overgrowth (SIBO), inflammatory disease, inflammatory bowel disease (IBD), and diverticular disease. Currently, rifaximin is manufactured as 200 mg and 550 mg tablets and is approved for administration at daily dosages of 600 mg (for TD), 1100 mg (for HE), or 1650 mg (for IBS-D).

Because rifaximin is largely water-insoluble and poorly absorbed, systemic effects are unusual. For example, less than 0.5% of rifaximin is absorbed into the bloodstream when taken orally. This translates to a highly favorable safety profile that is comparable to placebo. Rifaximin is, however, increasingly soluble in bile. This results in higher luminal concentrations and enhanced antimicrobial effects against enteric bacteria. Larger effects in the small intestine as well as low microbial resistance and minimal effect on colonic microflora are also seen. As such, rifaximin is highly favored for use against conditions associated with the small intestine as well as for long term use (e.g., 6 months for longer or in instances where bacterial resistance is of concern).

Despite these beneficial features, new evidence suggests that the full therapeutic potential of rifaximin has not yet been realized.

SUMMARY

It has now been found that rifaximin absorption varies throughout certain regional environments of the gastrointestinal tract (GI). For example, FIG. 1 and Table 1, as discussed in more detail below, shows that the extent of rifaximin exposure for the mid small bowel (MSB) following delivery of a 150 mg solid dispersion of rifaximin was less than half the exposure for the proximal small bowel (PSB). It was also found that the distal small bowel (DSB) had the lowest relative bioavailability ($F_{Rel}$) next to the colon. See id. These findings, and other data provided herein, suggest that regional absorption occurs, which may be due in part to changes in intestinal rifaximin permeability. This offers the potential to increase the solubilized rifaximin concentration in targeted areas of the intestinal tract without increasing unwanted systemic exposure. Additionally, providing controlled rifaximin release, as demonstrated herein can reduce or eliminate inconsistencies in drug dissolution and unwanted side effects such as increased systemic exposure or uncontrolled reductions of the normal GI flora.

Provided herein, therefore, are GI specific rifaximin release compositions which can be formulated for targeted delivery of the API to one or more portions of the GI tract, such as the upper GI tract, mid-GI tract, lower GI tract, and/or the colon.

In an aspect, the disclosed compositions provide targeted release of rifaximin to the upper or mid, or lower GI tract. In some aspects, the disclosed compositions provide targeted release of rifaximin to the upper or mid GI tract.

In an aspect, the disclosed compositions comprise rifaximin and a nonpareil bead substrate such as a sugar sphere or cellulose sphere. Without being limited to any one theory of the invention, the use of a soluble sugar sphere in the beads described herein was chosen, in part, because it provides an osmotic pressure that assists in driving dissolution of the rifaximin coated on the beads.

In an aspect, the disclosed compositions comprise rifaximin, a nonpareil bead substrate such as a sugar sphere, at least one polymer.

In some aspects, the disclosed compositions are in unit dosage form and comprise a plurality of first and second targeted release beads each having a unique combination of rifaximin, a nonpareil bead substrate such as a sugar sphere, and at least one polymer, wherein the first and second targeted release rifaximin beads are configured to release rifaximin at different locations in a subject's gastrointestinal tract.

In some aspects, the at least one polymer of the disclosed compositions is selected from a first pH independent polymer and a second pH independent polymer. In some aspects, the at least one polymer of the disclosed compositions is selected from a first pH independent polymer, a second pH independent polymer, and a pH dependent polymer.

In some aspects, the first pH independent polymer of the disclosed compositions is present in an amount of from about 1% to about 20% by weight based on the total weight of rifaximin in the composition. In some aspects, the second pH independent polymer of the disclosed compositions is present in an amount of from about 10% to about 50% by weight based on the total weight of rifaximin in the composition. In some aspects, the pH dependent polymer of the disclosed compositions is present in an amount of from about 25% to about 75% by weight based on the total weight of rifaximin in the composition.

In an aspect, the disclosed compositions comprise a surfactant. In some aspects, the disclosed compositions comprise a non-ionic surfactant present in an amount of from about 1% to about 30% by weight based on the total weight of rifaximin in the composition.

In an aspect, the disclosed compositions comprise a pharmaceutically acceptable plasticizer.

In an aspect, the disclosed compositions comprise an enteric coating. In some aspects, the enteric coating further comprises an anti-adherent additive.

In an aspect, the rifaximin in the disclosed compositions is crystalline, non-crystalline, and/or amorphous.

In an aspect, the rifaximin in the disclosed compositions is present in an amount of from about 0.5% to about 50% by weight based on the total weight of the composition.

Also provided herein is the use of one or more disclosed compositions treating one or more diseases in a subject in need thereof. In an aspect, the one or more diseases may include bowel-related or liver function disorders, developmental disorders, cardiovascular conditions, disorders affect the central nervous system, disorders associated with cognitive impairment, and cancers.

The pharmaceutical compositions described herein represent embodiments of a targeted release technology for delivering a rifamycin compound, such as rifaximin, to selected areas or regions of a subject's gastrointestinal tract for the treatment of disease. In an aspect, the pharmaceutical compositions described herein are provided to increase the gastrointestinal luminal solubility of rifaximin, while limiting systemic exposure. In some embodiments, the pharmaceutical compositions described herein result in less systemic rifaximin than administering XIFAXAN® (rifaximin) 550 mg tablets. In some embodiments, the pharmaceutical compositions described herein have greater accumulation ratios than XIFAXAN® (rifaximin) 550 mg tablets. In some embodiments, the pharmaceutical compositions described herein provide for prolonged luminal rifaximin exposure as compared to XIFAXAN® (rifaximin) 550 mg tablets. In some embodiments, the compositions described herein are useful in treating irritable bowel syndrome (IBS) (e.g., IBS-D), diarrhea, microbe associated diarrhea, infectious diarrhea, *Clostridium difficile* infections and symptoms (e.g., *Clostridium difficile* associated diarrhea), travelers' diarrhea, small intestinal bacterial overgrowth (SIBO), Crohn's disease, diverticular disease, pancreatitis (including chronic), pancreatic insufficiency, enteritis, colitis (e.g., ulcerative colitis, antibiotic associated colitis, and microscopic colitis), hepatic encephalopathy (or other diseases which lead to increased ammonia levels) and symptoms thereof, gastric dyspepsia, cirrhosis (e.g., alcoholic cirrhosis), polycystic liver disease, pouchitis, peritonitis, short bowel syndrome, inflammatory bowel disease, rosacea, sickle cell disease, and *H. pylori* infection.

Regarding sickle cell disease (SCD), the targeted release technology described herein provides a therapy in a patient by, for example, and without being limited to any one theory of the invention, (1) reducing levels of elevated circulating aged neutrophils (CANs), and/or (2) reducing or preventing the occurrence of vaso-occlusive crises (VOCs). As opposed to prior therapies, and the knowledge in the art, the benefits offered by the invention described herein are provided at a substantially reduced dosage of rifaximin while providing clinical benefit.

Patients having SCD may have recurrent painful vaso-occlusive crises (VOCs), which is the most common clinical manifestation of SCD. VOC occurs when the patient's microcirculation is obstructed by sickled red blood cells (RBCs), which may result in ischemic injury, ulcers, priapism, organ damage, and spontaneous abortion. Furthermore, patients having SCD may, overall, have a poor quality of life and a shortened lifespan.

Neutrophils have been implicated in regulating VOC in SCD patients. SCD patients with WBC>$15\times10^9$/L are more likely to develop stroke, acute chest syndrome, and premature death. Neutrophils in SCD patients are also shown to exhibit increased levels of activation molecules, including CD64 and CD11b/CD18, with their sera having elevated levels of soluble CD62L. A subset of neutrophils known as circulating aged neutrophils (CANs) are substantially elevated. CANs are characterized by having a high surface expression of CXCR4 and low CD62L. Activated and aged neutrophils may be immobilized in the circulatory system on the endothelium and form the nidus for the adhesion of sickled RBCs, which may lead to VOC.

It has been reported that modulating intestinal microbial composition may be a therapeutic option in treating SCD patients to reduce VOC through the reduction of activated and aged neutrophils. In one study, it was found that a 550 mg dose of rifaximin (i.e., XIFAXAN® 550 mg tablets), delivered BID, was capable of reducing CANs in SCD patients (Clinical Trial Identifier: NCT03719729). Furthermore, when SCD patients received a 550 mg dose of rifaximin (i.e., XIFAXAN® 550 mg tablets) BID for 6 months, the result was a decrease in the number of VOCs, and thus an increased quality of life.

In an embodiment, the invention described herein includes a method of treating sickle cell disease (SCD) in a patient in need thereof comprising administering a disclosed targeted release composition to the patient. In some embodiments, the method of treating sickle cell disease (SCD) comprises reducing elevated levels of circulating aged neutrophils (CANs) in the patient. In some embodiments, the method of treating sickle cell disease (SCD) in a patient comprises treating vaso-occlusive crisis (VOC) in the patient. In some embodiments, treating vaso-occlusive crisis (VOC) in the patient comprises (1) alleviating one or more symptoms of VOC in the patient; (2) reducing or preventing the occurrence of VOCs in the patient; (3) reducing the duration or severity of VOC in the patient; and/or (4) mediating or otherwise reducing the patient's opioid usage during VOC. In some embodiments, the method of treating sickle cell (SCD) in the patient comprises alleviating one or more symptoms of vaso-occlusive crisis (VOC) in the patient. In some embodiments, the method of treating sickle cell disease (SCD) in the patient comprises reducing or preventing the occurrence of vaso-occlusive crises (VOCs) in the patient. In some embodiments, the method of treating sickle cell disease (SCD) comprises reducing the duration or severity of VOC in the patient. In some embodiments, the method of treating sickle cell disease (SCD) in the patient comprises mediating or otherwise reducing the patient's opioid usage during vaso-occlusive crisis (VOC) in the patient.

In some embodiments, the methods described herein further include administering an additional therapeutic agent, such as an SCD therapeutic agent. In some embodiments, the additional therapeutic agent is an SCD therapeutic agent. In some embodiments, the SCD therapeutic agent is selected from the group consisting of hydroxyurea, L-glutamine, hydroxycarbamide, an erythropoietin stimulating agent, an opioid analgesic, and combinations thereof. In some embodiments, the opioid analgesic is selected from the group consisting of morphine, codeine, hydrocodone, hydromorphone, methadone, tramadol, oxycodone, tapentadol, fentanyl, and combinations thereof. In some embodiments, the SCD therapeutic agent comprises an opioid analgesic.

Further provided is the use of the targeted release technology described herein for the delivery of poorly soluble therapeutic compounds. Thus, in an aspect, provided are compositions for targeted release to at least one of the upper, lower, and mid GI tract comprising a nonpareil bead substrate such as a sugar sphere and at least one polymer described herein. Additional components such as one or more surfactants, one or more pharmaceutically acceptable plasticizers, one or more enteric coatings, and/or one or more anti-adherent additives are also contemplated for this aspect.

DETAILED DESCRIPTION

Unless defined otherwise, all technical and scientific terms used herein have the same meaning as is commonly understood by a person having ordinary skill in the art to which this invention pertains.

When ranges are used herein to describe, for example, amounts of particular compounds or ingredients, all combinations and sub-combinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The term "comprising" (and related terms such as "comprise" or "comprises" or "having" or "including") includes those embodiments such as, for example, an embodiment of any composition of matter, method or process that "consist of" or "consist essentially of" the described features.

1. Description of Compositions

Disclosed herein are targeted release rifaximin compositions which are useful for delivering rifaximin to different areas of the GI tract. See e.g., FIG. 2, where it is shown that disclosed compositions can be adjusted to provide extended release in a pH independent or pH dependent manner. These properties are beneficial in view of the finding that the exposure of rifaximin is different between the colon and mid-, proximal, and distal small bowel suggesting the varying pH has a substantial effect on rifaximin absorption. See e.g., FIG. 1 and Table 1.

Figure 3:
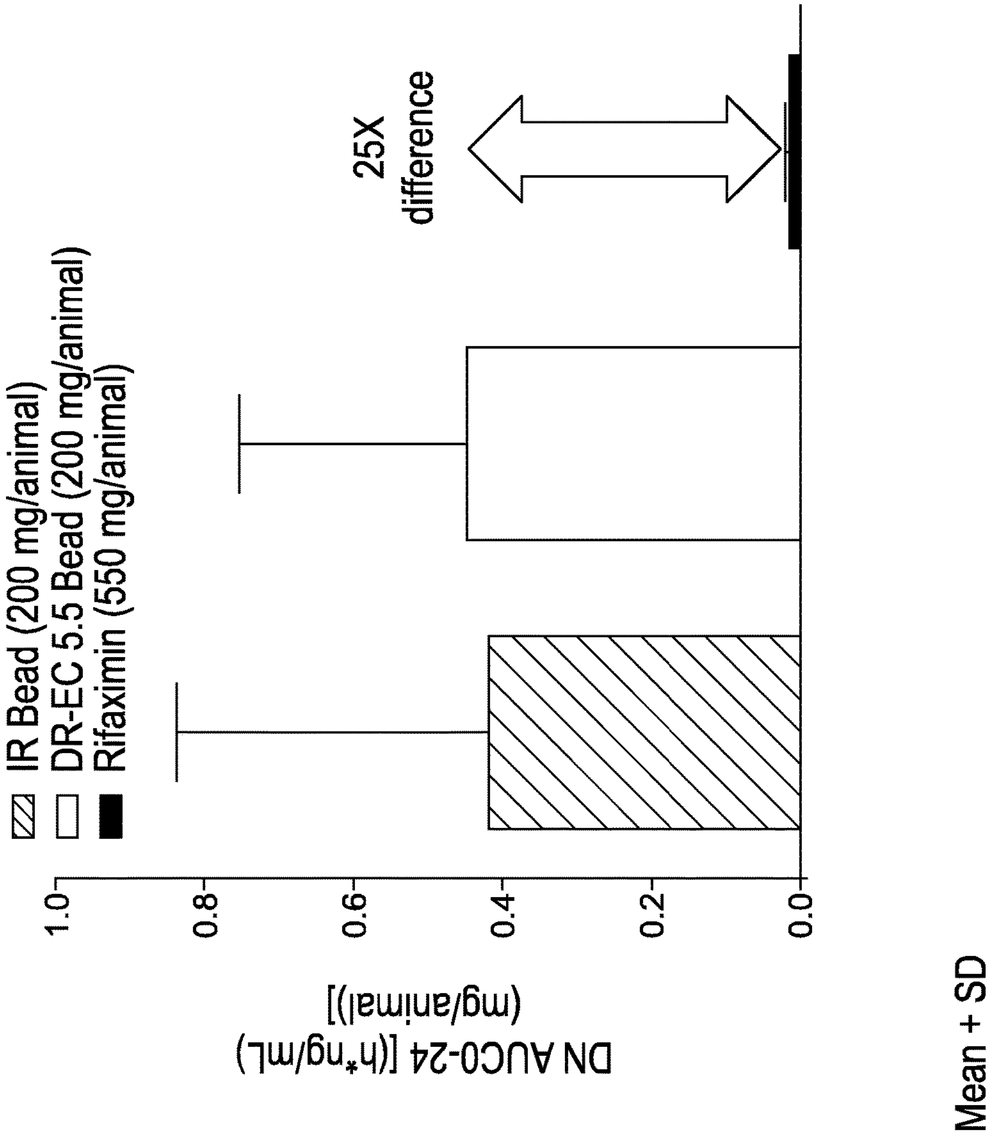
FIG. 3 shows the PK results ($AUC_{0-24}$) between MGI and UGI compositions and 550 mg Xifaxin tablet in dogs.

The mean PK parameters ($C_{max}$, AUC) are about 10-fold higher for 200 mg strength upper GI and mid GI inventive compositions compared to XIFAXAN® 550 tablet. When dose normalized, about a 25-fold difference in $AUC_{0-24}$ was found between inventive compositions beads and XIFAXAN® 550 tablet drug absorption See e.g., FIG. 3.

In one aspect, the invention described herein includes bead compositions comprising a nonpareil bead substrate coated with a compound having poor aqueous solubility and at least one polymer. In some embodiments, the compound having poor aqueous solubility may be a rifamycin compound selected from the group consisting of rifaximin, rifamycin A, rifamycin B, rifamycin C, rifamycin D, rifamycin E, rifamycin S, rifamycin SV, rifampin (rifampicin), rifapentine, rifabutin, rifalazil, and pharmaceutically acceptable salts thereof, which may be in a crystalline, non-crystalline, and/or amorphous form. In some embodiments, the rifamycin compound is rifaximin. Accordingly, the invention described herein includes rifaximin bead compositions comprising a nonpareil bead substrate coated with rifaximin and at least one polymer.

In one embodiment, the nonpareil bead substrate is selected from a sugar sphere or a cellulose bead. In one embodiment, the nonpareil bead substrate is a sugar sphere. Elements from this embodiment may be combined with one or more of the additional embodiments and/or aspects described herein.

In one embodiment, the at least one polymer is selected from a pH independent polymer and a pH dependent polymer. In some embodiments, the pH independent polymer includes one or more pH independent polymers such as, for example, a first pH independent polymer and a second pH independent polymer. In some embodiments, the pH dependent polymer includes one or more pH dependent polymers. In some embodiments, the at least one polymer is selected from a first pH independent polymer, a second pH independent polymer, and a pH dependent polymer. Elements from this embodiment may be combined with one or more of the additional embodiments and/or aspects described herein.

In one embodiment, the at least one polymer is selected from a first pH independent polymer and a second pH independent polymer. Elements from this embodiment may be combined with one or more of the additional embodiments and/or aspects described herein.

In one embodiment, the first pH independent polymer is present in an amount of from about 5% to about 15% by weight based on the total weight of rifaximin in the composition. In some embodiments, the first pH independent polymer is present in an amount of from about 6% to about 12% by weight based on the total weight of rifaximin in the composition. In some embodiments, the first pH independent polymer is present in an amount of from about 6% to about 10% by weight based on the total weight of rifaximin in the combination. In some embodiments, the first pH independent polymer is present in an amount of from about 5% to about 9% by weight based on the total weight of rifaximin in the combination. In some embodiments, the first pH independent polymer is present in an amount of from about 5% to about 8% by weight based on the total weight of rifaximin in the combination. In some embodiments, the first pH independent polymer is present in an amount of from about 5% to about 7% by weight based on the total weight of rifaximin in the combination. In some embodiments, the first pH independent polymer is present in an amount of from about 6% to about 7% by weight based on the total weight of rifaximin in the combination. In some embodiments, the first pH independent polymer is present in an amount of from about 7% to about 10% by weight based on the total weight of rifaximin in the composition. In some embodiments, the first pH independent polymer is present in an amount of from about 8% to about 9% by weight based on the total weight of rifaximin in the composition. In some embodiments, the first pH independent polymer is present in an amount of from about 0.1% to about 2.5% by weight based on the total weight of the composition. In some embodiments, the first pH independent polymer is present in an amount of from about 0.3% to about 2.3% by weight based on the total weight of the composition. In some embodiments, the first pH independent polymer is present in an amount of from about 0.3% to about 0.5% or from about 1.8% to about 2.0% by weight based on the total weight of the composition. In some embodiments, the first pH independent polymer is present in an amount of from about 0.4% to about 0.5% or from about 1.9% to about 2.0% by weight based on the total weight of the composition. Elements from these embodiments may be combined with one or more of the additional embodiments and/or aspects described herein.

In one embodiment, the second pH independent polymer is present in an amount of from about 15% to about 35% by weight based on the total weight of rifaximin in the combination. In some embodiments, the second pH independent polymer is present in an amount of from about 15% to about 25% by weight based on the total weight of rifaximin in the combination. In some embodiments, the second pH independent polymer is present in an amount of from about 15% to about 20% by weight based on the total weight of rifaximin in the combination. In some embodiments, the second pH independent polymer is present in an amount of from about 18% to about 20% by weight based on the total weight of rifaximin in the combination. In some embodiments, the second pH independent polymer is present in an amount of from about 19% to about 20% by weight based on the total weight of rifaximin in the combination. In some embodiments, the second pH independent polymer is present in an amount of from about 20% to about 35% by weight based on the total weight of rifaximin in the composition. In some embodiments, the second pH independent polymer is present in an amount of from about 25% to about 30% by weight based on the total weight of rifaximin in the composition. In some embodiments, the second pH independent polymer is present in an amount of from about 26% to about 27% by weight based on the total weight of rifaximin in the composition. In some embodiments, the second pH independent polymer is present in an amount of from about 0.5% to about 4.0% or from about 3.0% to about 8.0% by weight based on the total weight of the composition. In some embodiments, the second pH independent polymer is present in an amount of from about 0.5% to about 2.0% or from about 4.0% to about 7.0% by weight based on the total weight of the composition. In some embodiments, the second pH independent polymer is present in an amount of from about 0.1% to about 2.0% or from about 5.0% to about 6.0% by weight based on the total weight of the composition. Elements from these embodiments may be combined with one or more of the additional embodiments and/or aspects described herein.

In one embodiment, the rifaximin to pH independent polymer in the compositions is provided in a weight ratio of about 65:35 to about 85:15, respectively. In some embodiments, the rifaximin to pH independent polymer in the compositions is provided in a weight ratio of about 70:30 to about 80:20, respectively. In some embodiments, the rifaximin to pH independent polymer in the compositions is provided in a weight ratio of about 70:30 to about 75:25, respectively. In some embodiments, the rifaximin and pH independent polymer, which may be included in the compositions described herein, are not provided in a weight ratio of 25:75, 50:50, or 75:25, respectively. In some embodiments, the compositions described herein include more rifaximin than pH independent polymer, by weight, when such compositions include both rifaximin and pH independent polymer.

In one embodiment, the pH independent polymer comprises one or more of hydroxypropyl methylcellulose (HPMC), polyvinylpyrrolidone (PVP), hydroxyethyl cellulose (HEC) polyethylene glycol (PEG), polyvinyl alcohol (PVA), polyacrylic acid (PAA), hydroxypropyl cellulose, methyl cellulose, ethyl cellulose, and divinyl ether maleic anhydride copolymer (DIVEMA). In some embodiments, the first and second pH independent polymer are selected from hydroxypropyl methylcellulose (HPMC), polyvinylpyrrolidone (PVP), hydroxyethyl cellulose (HEC) polyethylene glycol (PEG), polyvinyl alcohol (PVA), polyacrylic acid (PAA), hydroxypropyl cellulose, methyl cellulose, ethyl cellulose, and divinyl ether maleic anhydride copolymer (DIVEMA). In some embodiments, the first pH independent polymer is HPMC. In some embodiments, the second pH independent polymer is PVP. Elements from these embodiments may be combined with one or more of the additional embodiments and/or aspects described herein.

In one embodiment, the at least one polymer is a pH dependent polymer. Elements from this embodiment may be combined with one or more of the additional embodiments and/or aspects described herein.

In one embodiment, the pH dependent polymer is present in an amount of from about 20% to about 60% by weight based on the total weight of rifaximin in the composition. In some embodiments, the pH dependent polymer is present in an amount of from about 20% to about 50% by weight based on the total weight of rifaximin in the composition. In some embodiments, the pH dependent polymer is present in an amount of from about 25% to about 45% by weight based on the total weight of rifaximin in the composition. In some embodiments, the pH dependent polymer is present in an amount of from about 30% to about 40% by weight based on the total weight of rifaximin in the composition. In some embodiments, the pH dependent polymer is present in an amount of from about 30% to about 35% by weight based on the total weight of rifaximin in the composition. In some embodiments, the pH dependent polymer is present in an amount of from about 40% to about 60% by weight based on the total weight of rifaximin in the composition. In some embodiments, the pH dependent polymer is present in an amount of from about 40% to about 50% by weight based on the total weight of rifaximin in the composition. In some embodiments, the pH dependent polymer is present in an amount of from about 43% to about 47% by weight based on the total weight of rifaximin in the composition. In some embodiments, the pH dependent polymer is present in an amount of from about 44% to about 45% by weight based on the total weight of rifaximin in the composition. In some embodiments, the pH dependent polymer is present in an amount of from about 1% to about 12% by weight based on the total weight of rifaximin in the composition. In some embodiments, the pH dependent polymer is present in an amount of from about 1% to about 4% or from about 8% to about 11% by weight based on the total weight of the composition. In some embodiments, the pH dependent polymer is present in an amount of from about 1% to about 3% or from about 8% to about 10% by weight based on the total weight of the composition. In some embodiments, the pH dependent polymer is present in an amount of from about 2% to about 3% or from about 9% to about 10% by weight based on the total weight of the composition. Elements from these embodiments may be combined with one or more of the additional embodiments and/or aspects described herein.

In one embodiment, the rifaximin to pH dependent polymer in the compositions is provided in a weight ratio of about 65:35 to about 75:25, respectively. In some embodiments, the rifaximin to pH dependent polymer in the compositions is provided in a weight ratio of about 60:40 to about 70:30, respectively. In some embodiments, the rifaximin to pH dependent polymer in the compositions is provided in a weight ratio of about 65:35 to about 70:30, respectively. In some embodiments, the rifaximin and pH dependent polymer, which may be included in the compositions described herein, are not provided in a weight ratio of 25:75, 50:50, or 75:25, respectively. In some embodiments, the compositions described herein include more rifaximin than pH dependent polymer, by weight, when such compositions include both rifaximin and pH dependent polymer.

In one embodiment, the pH dependent polymer comprises one or more of hydroxypropyl methylcellulose acetate succinate (HPMC-AS), methacrylic/ethylacrylic copolymer, hydroxypropyl methylcellulose acetate phthalate (HPMC-P), cellulose acetate phthalate (CAP), and cellulose acetate trimellitate (CAT). In some embodiments, the pH dependent polymer is selected from hydroxypropyl methylcellulose acetate succinate (HPMC-AS), methacrylic/ethylacrylic copolymer, hydroxypropyl methylcellulose acetate phthalate (HPMC-P), cellulose acetate phthalate (CAP), and cellulose acetate trimellitate (CAT). In some embodiments, the at least one pH dependent polymer is HPMC-AS. In some embodiments, the at least one pH dependent polymer is HPMC-AS grade M. Elements from these embodiments may be combined with one or more of the additional embodiments and/or aspects described herein.

In one embodiment, the composition further comprises a surfactant. In some embodiments, the surfactant is a non-ionic surfactant. In some embodiments, the surfactant is poloxamer 407. Elements from these embodiments may be combined with one or more of the additional embodiments and/or aspects described herein.

In one embodiment, the surfactant is present in an amount of from about 5% to about 15% by weight based on the total weight of rifaximin in the composition. In some embodiments, the surfactant is present in an amount of from about 7% to about 9% by weight based on the total weight of rifaximin in the composition. In some embodiments, the surfactant is present in an amount of from about 8% to about 9% by weight based on the total weight of rifaximin in the composition. Elements from these embodiments may be combined with one or more of the additional embodiments and/or aspects described herein.

In one embodiment, the composition further comprises diethyl phthalate or dibutyl phthalate. In some embodiments, the composition comprises diethyl phthalate. Elements from these embodiments may be combined with one or more of the additional embodiments and/or aspects described herein.

In one embodiment, the composition further comprises a pharmaceutically acceptable plasticizer. In some embodiments, the pharmaceutically acceptable plasticizer is an alkyl citrate. In some embodiments, the pharmaceutically acceptable plasticizer is selected from triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), and trimethyl citrate (TMC). In some embodiments, the pharmaceutically acceptable plasticizer is TEC. Elements from these embodiments may be combined with one or more of the additional embodiments and/or aspects described herein.

In one embodiment, the composition further comprises an enteric coating. In some embodiments, the enteric coating surrounds the nonpareil bead substrate coated with rifaximin and at least one polymer. In some embodiments, the enteric coating comprises a methacrylic acid-acrylate copolymer and, optionally, a combination of glycerol monostearate, triethyl citrate, and polysorbate 80 (e.g., Plasacryl HTP 20). In some embodiments, the enteric coating comprises a methacrylic acid ethylacrylate copolymer (e.g., Eudragit L30D55) and, optionally, a combination of glycerol monostearate, triethyl citrate, and polysorbate 80 (e.g., Plasacryl HTP 20). In some embodiments, the enteric coating further comprises an anti-adherent additive. Elements from these embodiments may be combined with one or more of the additional embodiments and/or aspects described herein.

In one embodiment, the composition further comprises an antioxidant and/or a chelating agent. In some embodiments, the compositions described herein include one or more antioxidants or chelating agents selected from ascorbyl palmitate, butylated hydroxyanisole (BHA), butylated hydroxytoluene (BHT), citric acid, sodium metabisulfite, cysteine, potassium metabisulfite, propyl gallate, sodium thiosulfate, vitamin E (e.g., Vitamin E TPGS), and 3,4-dihydroxybenzoic acid.

In one embodiment, the rifaximin in the provided composition is crystalline, non-crystalline, and/or amorphous. Elements from this embodiment may be combined with one or more of the additional embodiments and/or aspects described herein.

In one embodiment, the rifaximin in the provided composition is in a solid dispersion form with the at least one polymer, as described herein. Elements from this embodiment may be combined with one or more of the additional embodiments and/or aspects described herein.

In one embodiment, the rifaximin in the provided composition is present in an amount of from about 1% to about 30% by weight based on the total weight of the composition. In some embodiments, the rifaximin is present in an amount of from about 1% to about 10% by weight based on the total weight of the composition. In some embodiments, the rifaximin is present in an amount of from about 4% to about 6% by weight based on the total weight of the composition. In some embodiments, the rifaximin is present in an amount of from about 15% to about 25% by weight based on the total weight of the composition. In some embodiments, the rifaximin is present in an amount of from about 20% to about 23% by weight based on the total weight of the composition. Elements from these embodiments may be combined with one or more of the additional embodiments and/or aspects described herein.

2. Definitions

"Rifaximin" refers to the antibiotic 4-Deoxy-4'-methylpyrido[1',2'-1,2]imidazo[5,4-c]rifamycin SV, having the chemical structure depicted below:

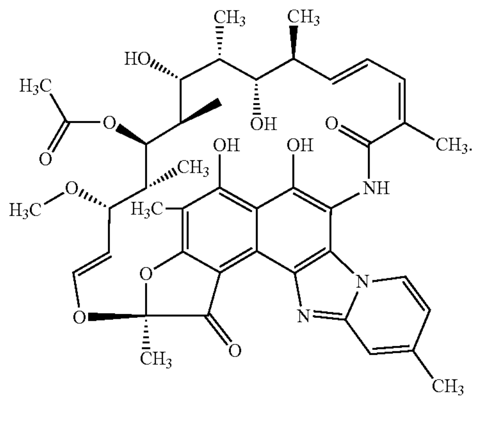 [SMILES: CO[C@H]1/C=C/O[C@@]2(C)Oc3c(C)c(O)c4c(O)c(c5c(nc6cc(C)ccn65)c4c3C2=O)NC(=O)/C(C)=C\C=C\[C@H](C)[C@H](O)[C@@H](C)[C@@H](O)[C@@H](C)[C@H](OC(C)=O)[C@@H]1C]

Rifaximin may exist in a number of different solvate, hydrate, polymorphic, and/or crystalline forms, including form α, form β, form γ, form δ, form ε, and amorphous forms of rifaximin. In some embodiments, rifaximin as set forth herein may be form α, form β, form γ, form δ, form ε, amorphous, or a combination thereof. Forms, formulations, and methods of using rifaximin are described, for example, in U.S. Pat. Nos. 7,045,620, 7,906,542, 7,915,275, 8,193,196, 8,309,569, 8,518,949, 8,741,904, 9,737,610, the entirety of which are incorporated herein by reference.

The term "solid dispersion" as used herein refers to a dispersion of rifaximin and an inert carrier matrix in a solid form, i.e., rifaximin is homogenously mixed with an inert carrier. The inert matrix is generally hydrophilic (e.g., a polymer such as HPMC-AS) and may be crystalline, non-crystalline, and/or amorphous. It will be understood that it is not necessarily the preparation method that governs the properties of the solid dispersion, but rather the molecular arrangement of the contents of the dispersion. Thus, absent an expression to do so, or an incorporation of process restrictions, solid dispersions are not to be limited by the process to which they are made. The terms "solid dispersion", "soluble solid dispersion", and the abbreviations "SD" or "SSD" are used interchangeably and each refer to the disclosed solid dispersion of rifaximin.

The term "upper GI tract" refers to, collectively, the stomach and proximal small bowel.

The term "mid GI tract" refers to the mid small bowel.

The term "lower GI tract" refers to the distal small bowel.

A "pH independent polymer" refers to those polymers which are not overly sensitive to changes in the pH of the surrounding media (e.g., the GI tract). In one aspect, their dimensional properties (e.g., ability to swell or deswell) is not contingent on the acidity or basicity of the media to which it is exposed to. As used herein, a pH independent polymer may refer to one or more of hydroxypropyl methylcellulose (HPMC), polyvinylpyrrolidone (PVP), hydroxyethyl cellulose (HEC) polyethylene glycol (PEG), polyvinyl alcohol (PVA), polyacrylic acid (PAA), hydroxypropyl cellulose, methyl cellulose, ethyl cellulose, and divinyl ether maleic anhydride copolymer (DIVEMA).

A "pH dependent" or "pH responsive" polymer refers to those polymers which will respond to changes in the pH of the surrounding media (e.g., the GI tract) by e.g., altering their dimension. In one aspect, the polymer may swell or deswell based on the pH of the environment. pH independent polymers can comprise natural polymer blocks, poly acids, or poly bases. In another aspect, the polymer may exhibit pH dependent solubility such that it dissolves or begins to dissolve when a certain pH is achieved or exceeded. As used herein, a pH dependent polymer may refer to one or more of hydroxypropyl methylcellulose acetate succinate (HPMC-AS), methacrylic/ethylacrylic copolymer, hydroxypropyl methylcellulose acetate phthalate (HPMC-P), cellulose acetate phthalate (CAP), cellulose acetate trimellitate (CAT), and methacrylic acid ethylacrylate copolymer.

"Hepatic encephalopathy" or "HE" for shorthand is defined as an altered mental status diagnosed as HE and defined as an increase of the Conn score to Grade≥2 (i.e., 0 or 1 to ≥2). HE may be considered "covert" or "overt" HE (CHE or OHE, respectively) depending upon the severity of the symptoms associated therewith. HE may be described as a continuum denoted by the West Haven Criteria (WHC): Grade 0—Minimal hepatic encephalopathy with symptoms potentially including impaired complex and sustained attention; Grade 1 (CHE)—Symptoms include trivial lack of awareness, euphoria or anxiety, shortened attention span, impairment of addition or subtraction, and altered sleep rhythm where clinical findings include mild asterixis or tremor; Grade 2 (OHE)—Symptoms include lethargy or apathy, disorientation for time, obvious personality change, and inappropriate behavior where clinical findings include obvious asterixis, dyspraxia, and slurred speech; Grade 3 (OHE)—Symptoms include somnolence to semistupor, responsive to stimuli, confused, gross disorientation, and bizarre behavior where clinical findings include muscular rigidity, clonus, and hyperreflexia; and Grade 4 (OHE)—Symptoms include coma where clinical findings include decerebrate posturing. OHE may also be observed on the Hepatic Encephalopathy Grading Instrument (HEGI), which uses clinical findings (present for at least 1 hour) to measure a patient's disorientation and thereby the severity of an HE episode (on a scale of Grade 2 to Grade 4)—Grade 4 being the most severe and Grade 2 being the least severe.

"Esophageal variceal bleeding" or "EVB" for shorthand is defined as the occurrence of a clinically significant gastrointestinal bleed being defined as 1) bleeding from an esophageal or gastric varix at the time of endoscopy or 2) the presence of large varices with blood evident in the stomach, and no other identifiable cause of bleeding observed during endoscopy, and at least one or more of the following criteria is present: i) drop in hemoglobin of greater than 2 g/dL over the first 48 hours post hospital admission, ii) transfusion requirement of 2 units of blood or more within 24 hours of hospital admission, iii) a systolic blood pressure of less than 100 mm Hg, or iv) pulse rate greater than 100 beat/min at the time of admission.

"Spontaneous bacterial peritonitis" or "SBP" for shorthand is defined as greater than 250 polymorphonuclear (PMN) cells/$mm^3$ and/or positive monomicrobial culture in the ascitic fluid.

"Hepatorenal syndrome" (HRS) is defined as i) progressive rise in serum creatinine (>1.5 mg/dL) with no improvement after at least 2 days with diuretic withdrawal and volume expansion with albumin, ii) absence of parenchymal kidney disease, iii) oliguria, iv) absence of shock, and v) no current or recent (within 3 months prior randomization) treatment with nephrotoxic drugs.

As used herein the term "treatment of sickle cell disease (SCD)" refers to the amelioration, prevention, or reduction in frequency of one or more symptoms of SCD. For example, "treatment of sickle cell disease (SCD)" may refer to the reduction of elevated levels of circulating aged neutrophils (CANs) in a patient, where such levels of CANs are elevated as compared, for example, to levels of CANs that would be expected in a patient who is not diagnosed as having SCD. As another example, the "treatment of sickle cell disease (SCD)" may refer to treating vaso-occlusive crisis (VOC) in the patient, where "treating vaso-occlusive crisis (VOC) or "treating vaso-occlusive crises (VOCs)," as the case may be, may refer to (1) alleviating one or more symptoms of VOC in the patient; (2) reducing or preventing the occurrence of VOCs in the patient; (3) reducing the duration or severity of VOC in the patient; and/or (4) mediating or otherwise reducing the patient's opioid usage during VOC. For example, symptoms of VOC include, without limitation, pain, swelling, ischemic injury, ulcers, priapism, organ damage, and spontaneous abortion. The "treatment of sickle cell disease (SCD)" may refer to preventing the occurrence of vaso-occlusive crisis (VOC) in a patient, such as a patient having a history of VOC (e.g., at least one VOC in the 12 months prior to treatment). The "treatment of sickle cell disease (SCD)" may refer to reducing the occurrence or frequency of vaso-occlusive crisis (VOC) in a patient, such as a patient having a history of VOC. The "treatment of sickle cell disease (SCD)" may refer to reducing the severity of vaso-occlusive crisis (VOC) occurrences in a patient, such as a patient having a history of VOC. The "treatment of sickle cell disease (SCD)" may refer to mediating or reducing a patient's opioid usage during VOC. The mediation or reduction of a patient's opioid usage during VOC may refer to, for example, mediating or reducing the patient's reliance on opioids (e.g., opioid analgesics) for pain management during VOC as compared to the patient's history of reliance on such opioids during VOC. Alternatively, the mediation or reduction of a patient's opioid usage during VOC may refer to mediating or reducing the patient's reliance on opioids (e.g., opioid analgesics) for pain management during VOC as compared to a patient during VOC who is not receiving a targeted release composition as described herein.

The term "effective amount" or "therapeutically effective amount" refers to an amount of a composition described herein that will elicit a biological or medical response of a subject, e.g., a composition having a dosage of rifaximin between about 0.001 to about 100 mg/kg body weight/day.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

"Pharmaceutically acceptable" means molecular entities and compositions that do not produce an adverse, allergic or other untoward reaction when administered to an animal, or a human, as appropriate.

The terms "treatment," "treat," and "treating" refer to reversing, alleviating, reducing the likelihood of developing, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

3. Dual Release Compositions

In one aspect, provided are rifaximin delivery compositions comprising a plurality of first targeted release rifaximin beads and a plurality of second targeted release rifaximin beads, wherein the first targeted release rifaximin beads comprise a sugar sphere coated with a combination comprising rifaximin, a first pH independent polymer (e.g., HPMC), and a second pH independent polymer (e.g., PVP); and the second targeted release rifaximin beads comprise a sugar sphere coated with a combination comprising rifaximin and a pH dependent polymer (e.g., HPMC-AS), wherein the first and second targeted release rifaximin beads are configured to release rifaximin at different locations in a subject's gastrointestinal tract.

In the embodiments described herein, the first targeted release rifaximin beads may be referred to as upper gastrointestinal (UGI) beads or extended release (ER) beads. As used herein, the terms "UGI beads" and "ER beads" are interchangeable.

In the embodiments described herein, the second targeted release rifaximin beads may be referred to as mid-gastrointestinal (MGI) beads or delayed extended release (DER) beads. As used herein, the terms "MGI beads" and "DER beads" are interchangeable. In some embodiments, the MGI beads may be prepared to target the mid-GI tract and may also be prepared to target the mid-GI tract and the lower GI tract. In some embodiments, MGI beads may be prepared to target the mid-GI tract, the lower GI tract, and the colon.

In one embodiment, the rifaximin delivery composition further comprises at least one surfactant. In some embodiments, the surfactant is a non-ionic surfactant. In some embodiments, the surfactant is poloxamer 407. Elements from these embodiments may be combined with one or more of the additional embodiments and/or aspects described herein.

In one embodiment, the rifaximin delivery composition further comprises diethyl phthalate or dibutyl phthalate. In some embodiments, the composition comprises diethyl phthalate. Elements from these embodiments may be combined with one or more of the additional embodiments and/or aspects described herein.

In one embodiment, the rifaximin delivery composition further comprises a pharmaceutically acceptable plasticizer. In some embodiments, the pharmaceutically acceptable plasticizer is an alkyl citrate. In some embodiments, the pharmaceutically acceptable plasticizer is selected from triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), and trimethyl citrate (TMC). In some embodiments, the pharmaceutically acceptable plasticizer is TEC. Elements from these embodiments may be combined with one or more of the additional embodiments and/or aspects described herein.

In one embodiment, the rifaximin delivery composition further comprises an enteric coating. In some embodiments, the rifaximin delivery composition further comprises an enteric coating surrounding the sugar sphere coated with a combination comprising rifaximin and HPMC-AS of the second targeted release beads. In some embodiments, the enteric coating comprises a methacrylic acid-acrylate copolymer and, optionally, a combination of glycerol monostearate, triethyl citrate, and polysorbate 80 (e.g., Plasacryl HTP 20). In some embodiments, the enteric coating comprises an anionic methacrylic acid-acrylate copolymer. In some embodiments, the enteric coating comprises copolymers of methacrylic acid and ethylacrylate (e.g., Eudragit L30D55) and, optionally, a combination of glycerol monostearate, triethyl citrate, and polysorbate 80 (e.g., Plasacryl HTP 20). In some embodiments, the enteric coating further comprises an anti-adherent additive. Elements from these embodiments may be combined with one or more of the additional embodiments and/or aspects described herein.

In one embodiment, the rifaximin of the combination of the first targeted release beads is crystalline, non-crystalline, and/or amorphous. Elements from this embodiment may be combined with one or more of the additional embodiments and/or aspects described herein.

In one embodiment, the rifaximin of the combination of the second targeted release beads is crystalline, non-crystalline, and/or amorphous. Elements from this embodiment may be combined with one or more of the additional embodiments and/or aspects described herein.

In one embodiment, the first target release beads are configured to release rifaximin to the upper GI tract. In some embodiments, the first target release beads are configured to release rifaximin into the first part of the small intestine. In some embodiments, the second target release beads are configured to release rifaximin into the mid-GI tract. In some embodiments, the second target release beads are configured to release rifaximin into the mid-GI tract and lower GI tract. In some embodiments, the second target release beads are configured to release rifaximin into the mid-GI tract, the lower GI tract, and the colon. Elements from these embodiments may be combined with one or more of the additional embodiments and/or aspects described herein.

In one embodiment, the second target release beads are configured to release into the mid gastrointestinal tract. Elements from this embodiment may be combined with one or more of the additional embodiments and/or aspects described herein.

4. Upper GI Targeted Compositions

Provided are rifaximin compositions which are formulated for delivery of rifaximin to the upper GI tract (referred to herein as UGI beads or ER beads). Such compositions include a rifaximin targeted release composition comprising a sugar sphere coated with a combination comprising rifaximin and pH independent polymer, including a first pH independent polymer (e.g., Hypromellose (HPMC)) and a second pH independent polymer (e.g., PVP). In some embodiments, the first pH independent polymer is HPMC (2910 50 mPa*s U.S.P.). In some embodiments, the second pH independent polymer is povidone (PVP) K-90 (e.g., Plasdone™ K-90 USP, EP, JP).

In one embodiment, the rifaximin to pH independent polymer in the compositions is provided in a weight ratio of about 65:35 to about 85:15, respectively. In some embodiments, the rifaximin to pH independent polymer in the compositions is provided in a weight ratio of about 70:30 to about 80:20, respectively. In some embodiments, the rifaximin to pH independent polymer in the compositions is provided in a weight ratio of about 70:30 to about 75:25, respectively. In some embodiments, the rifaximin and pH independent polymer, which may be included in the compositions described herein, are not provided in a weight ratio of 25:75, 50:50, or 75:25, respectively. In some embodiments, the compositions described herein include more rifaximin than pH independent polymer, by weight, when such compositions include both rifaximin and pH independent polymer.

In one embodiment, the HPMC is present in an amount of from about 5% to about 15% by weight based on the total weight of rifaximin in the combination. In some embodiments, the HPMC is present in an amount of from about 6% to about 12% by weight based on the total weight of rifaximin in the combination. In some embodiments, the HPMC is present in an amount of from about 6% to about 10% by weight based on the total weight of rifaximin in the combination. In some embodiments, the HPMC is present in an amount of from about 5% to about 9% by weight based on the total weight of rifaximin in the combination. In some embodiments, the HPMC is present in an amount of from about 5% to about 8% by weight based on the total weight of rifaximin in the combination. In some embodiments, the HPMC is present in an amount of from about 5% to about 7% by weight based on the total weight of rifaximin in the combination. In some embodiments, the HPMC is present in an amount of from about 6% to about 7% by weight based on the total weight of rifaximin in the combination. In some embodiments, the HPMC is present in an amount of about 6.5% by weight based on the total weight of rifaximin in the combination. In some embodiments, the HPMC is present in an amount of from about 7% to about 10% by weight based on the total weight of rifaximin in the combination. In some embodiments, the HPMC is present in an amount of from about 8% to about 9% by weight based on the total weight of rifaximin in the combination. In some embodiments, the HPMC is present in an amount of from about 0.1% to about 2.5% by weight based on the total weight of the composition. In some embodiments, the HPMC is present in an amount of from about 0.3% to about 2.3% by weight based on the total weight of the composition. In some embodiments, the HPMC is present in an amount of from about 0.3% to about 0.5% or from about 1.8% to about 2.0% by weight based on the total weight of the composition. In some embodiments, the HPMC is present in an amount of from about 0.4% to about 0.5% or from about 1.9% to about 2.0% by weight based on the total weight of the composition. Elements from these embodiments may be combined with one or more of the additional embodiments and/or aspects described herein.

In one embodiment, the PVP is present in an amount of from about 15% to about 35% by weight based on the total weight of rifaximin in the combination. In some embodiments, the PVP is present in an amount of from about 15% to about 25% by weight based on the total weight of rifaximin in the combination. In some embodiments, the PVP is present in an amount of from about 15% to about 20% by weight based on the total weight of rifaximin in the combination. In some embodiments, the PVP is present in an amount of from about 18% to about 20% by weight based on the total weight of rifaximin in the combination. In some embodiments, the PVP is present in an amount of from about 19% to about 20% by weight based on the total weight of rifaximin in the combination. In some embodiments, the PVP is present in an amount of about 19.7% by weight based on the total weight of rifaximin in the combination. In some embodiments, the PVP is present in an amount of from about 20% to about 35% by weight based on the total weight of rifaximin in the combination. In some embodiments, the PVP is present in an amount of from about 25% to about 30% by weight based on the total weight of rifaximin in the combination. In some embodiments, the PVP is present in an amount of from about 26% to about 27% by weight based on the total weight of rifaximin in the combination. In some embodiments, the PVP is present in an amount of from about 0.5% to about 4.0% or from about 3.0% to about 8.0% by weight based on the total weight of the composition. In some embodiments, the PVP is present in an amount of from about 0.5% to about 2.0% or from about 4.0% to about 7.0% by weight based on the total weight of the composition. In some embodiments, the PVP is present in an amount of from about 0.1% to about 2.0% or from about 5.0% to about 6.0% by weight based on the total weight of the composition. Elements from these embodiments may be combined with one or more of the additional embodiments and/or aspects described herein.

In one embodiment, the combination further comprises a surfactant. In some embodiments, the surfactant is the combination further comprises a non-ionic surfactant. In some embodiments, the combination further comprises poloxamer 407. In some embodiments, the poloxamer 407 is Pluronic F127. Elements from these embodiments may be combined with one or more of the additional embodiments and/or aspects described herein.

In one embodiment, the surfactant is present in an amount of from about 5% to about 15% by weight based on the total weight of rifaximin in the composition. In some embodiments, the surfactant is present in an amount of from about 7% to about 9% by weight based on the total weight of rifaximin in the composition. In some embodiments, the surfactant is present in an amount of from about 8% to about 9% by weight based on the total weight of rifaximin in the composition. Elements from these embodiments may be combined with one or more of the additional embodiments and/or aspects described herein.

In one embodiment, the composition further comprises diethyl phthalate or dibutyl phthalate. In some embodiments, is the composition comprises diethyl phthalate. Elements from these embodiments may be combined with one or more of the additional embodiments and/or aspects described herein.

In one embodiment, the rifaximin is present in an amount of from about 1% to about 30% by weight based on the total weight of the composition. In some embodiments, the rifaximin is present in an amount of from about 1% to about 10% by weight based on the total weight of the composition. In some embodiments, the rifaximin is present in an amount of from about 4% to about 6% by weight based on the total weight of the composition. In some embodiments, the rifaximin is present in an amount of from about 15% to about 25% by weight based on the total weight of the composition. In some embodiments, the rifaximin is present in an amount of from about 20% to about 23% by weight based on the total weight of the composition. Elements from these embodiments may be combined with one or more of the additional embodiments and/or aspects described herein.

In one embodiment, the composition is a pH independent release composition. Elements from this embodiment may be combined with one or more of the additional embodiments and/or aspects described herein.

In one embodiment, the composition is for release into the upper gastrointestinal tract. In some embodiments, the composition is for release into the first part of the small intestine. Elements from these embodiments may be combined with one or more of the additional embodiments and/or aspects described herein.

5. Mid GI Targeted Compositions

Provided are rifaximin compositions which are formulated for delivery of rifaximin to the mid GI tract, lower GI tract, and/or the colon (referred to herein as MGI beads or DER beads). Such compositions include a rifaximin targeted release composition comprising a sugar sphere coated with a combination comprising rifaximin and a pH dependent polymer (e.g., HPMC-AS). In some embodiments, the pH dependent polymer includes hypromellose acetate succinate (HPMC-AS) (e.g., Ashland HPMC-AS MF, NF, JP).

In one embodiment, the rifaximin to pH dependent polymer in the compositions is provided in a weight ratio of about 65:35 to about 75:25, respectively. In some embodiments, the rifaximin to pH dependent polymer in the compositions is provided in a weight ratio of about 60:40 to about 70:30, respectively. In some embodiments, the rifaximin to pH dependent polymer in the compositions is provided in a weight ratio of about 65:35 to about 70:30, respectively. In some embodiments, the rifaximin and pH dependent polymer, which may be included in the compositions described herein, are not provided in a weight ratio of 25:75, 50:50, or 75:25, respectively. In some embodiments, the compositions described herein include more rifaximin than pH dependent polymer, by weight, when such compositions include both rifaximin and pH dependent polymer.

In one embodiment, the HPMC-AS is grade M. Elements from this embodiment may be combined with one or more of the additional embodiments and/or aspects described herein.

In one embodiment, the HPMC-AS is present in an amount of from about 20% to about 60% by weight based on the total weight of rifaximin in the composition. In some embodiments, the HPMC-AS is present in an amount of from about 20% to about 50% by weight based on the total weight of rifaximin in the composition. In some embodiments, the HPMC-AS is present in an amount of from about 25% to about 45% by weight based on the total weight of rifaximin in the composition. In some embodiments, the HPMC-AS is present in an amount of from about 30% to about 40% by weight based on the total weight of rifaximin in the composition. In some embodiments, the HPMC-AS is present in an amount of from about 30% to about 35% by weight based on the total weight of rifaximin in the composition. In some embodiments, the HPMC-AS is present in an amount of about 31% by weight based on the total weight of rifaximin in the composition. In some embodiments, the HPMC-AS is present in an amount of from about 40% to about 60% by weight based on the total weight of rifaximin in the mixture. In some embodiments, the HPMC-AS is present in an amount of from about 40% to about 50% by weight based on the total weight of rifaximin in the mixture. In some embodiments, the HPMC-AS is present in an amount of from about 43% to about 47% by weight based on the total weight of rifaximin in the mixture. In some embodiments, the HPMC-AS is present in an amount of from about 44% to about 45% by weight based on the total weight of rifaximin in the mixture. In some embodiments, the HPMC-AS is present in an amount of from about 1% to about 4% or from about 8% to about 11% by weight based on the total weight of the composition. In some embodiments, the HPMC-AS is present in an amount of from about 1% to about 3% or from about 8% to about 10% by weight based on the total weight of the composition. In some embodiments, the HPMC-AS is present in an amount of from about 2% to about 3% or from about 9% to about 10% by weight based on the total weight of the composition. Elements from these embodiments may be combined with one or more of the additional embodiments and/or aspects described herein.

In one embodiment, the combination further comprises a surfactant. In some embodiments, the combination further comprises a non-ionic surfactant. In some embodiments, the combination further comprises poloxamer 407. In some embodiments, the poloxamer 407 is Pluronic F127. Elements from these embodiments may be combined with one or more of the additional embodiments and/or aspects described herein.

In one embodiment, the surfactant is present in an amount of from about 5% to about 15% by weight based on the total weight of rifaximin in the composition. In some embodiments, the surfactant is present in an amount of from about 7% to about 9% by weight based on the total weight of rifaximin in the composition. In some embodiments, the surfactant is present in an amount of from about 8% to about 9% by weight based on the total weight of rifaximin in the composition. Elements from these embodiments may be combined with one or more of the additional embodiments and/or aspects described herein.

In one embodiment, the composition further comprises diethyl phthalate or dibutyl phthalate. In some embodiments, the composition comprises diethylphthalate. Elements from these embodiments may be combined with one or more of the additional embodiments and/or aspects described herein.

In one embodiment, the composition further comprises a pharmaceutically acceptable plasticizer. In some embodiments, the pharmaceutically acceptable plasticizer is an alkyl citrate. In some embodiments, the pharmaceutically acceptable plasticizer is selected from triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), and trimethyl citrate (TMC). In some embodiments, the pharmaceutically acceptable plasticizer is TEC. Elements from these embodiments may be combined with one or more of the additional embodiments and/or aspects described herein.

In one embodiment, the composition further comprises an enteric coating. In some embodiment, the composition further comprises an enteric coating around said combination and sugar sphere. In some embodiments, the enteric coating comprises a methacrylic acid-acrylate copolymer and, optionally, a combination of glycerol monostearate, triethyl citrate, and polysorbate 80 (i.e., Plasacryl HTP 20). In some embodiments, the enteric coating comprises a methacrylic acid ethylacrylate copolymer (e.g., Eudragit L30D55) and, optionally, a combination of glycerol monostearate, triethyl citrate, and polysorbate 80 (e.g., Plasacryl HTP 20). In some embodiments, the enteric coating further comprising an anti-adherent additive. Elements from these embodiments may be combined with one or more of the additional embodiments and/or aspects described herein.

In one embodiment, the rifaximin is present in an amount of from about 1% to about 30% by weight based on the total weight of the composition. In some embodiments, the rifaximin is present in an amount of from about 1% to about 10% by weight based on the total weight of the composition. In some embodiments, the rifaximin is present in an amount of from about 4% to about 6% by weight based on the total weight of the composition. In some embodiments, the rifaximin is present in an amount of from about 15% to about 25% by weight based on the total weight of the composition. In some embodiments, the rifaximin is present in an amount of from about 20% to about 23% by weight based on the total weight of the composition. Elements from these embodiments may be combined with one or more of the additional embodiments and/or aspects described herein.

In one embodiment, the composition is a pH dependent release composition. Elements from this embodiment may be combined with one or more of the additional embodiments and/or aspects described herein.

In one embodiment, the composition is for release into the mid gastrointestinal tract. Elements from this embodiment may be combined with one or more of the additional embodiments and/or aspects described herein.

5. Dosages

In one embodiment, the total amount of rifaximin in the disclosed compositions is less than about 250 mg (e.g., less than about 240 mg, less than about 230 mg, less than about 220 mg, less than about 210 mg, less than about 200 mg, less than about 190 mg, less than about 180 mg, less than about 170 mg, less than about 160 mg, less than about 150 mg, less than about 140 mg, less than about 130 mg, less than about 120 mg, less than about 110 mg, less than about 100 mg, less than about 90 mg, less than about 80 mg, less than about 70 mg, less than about 60 mg, less than about 50 mg, less than about 40 mg, less than about 30 mg, less than about 20 mg, or less than about 10 mg). In some aspects, the total amount of rifaximin ranges from about 2.5 mg to about 250 mg (e.g., about 5 mg to about 250 mg, about 5 mg to about 200 mg, about 5 mg to about 150 mg, about 5 mg to about 125 mg, about 10 mg to about 125 mg, about 10 mg to about 100 mg, about 25 mg to about 125 mg, about 25 mg to about 100 mg, about 25 mg to about 75 mg, about 30 mg to about 70 mg, about 35 mg to about 65 mg, about 40 mg to about 60 mg, about 45 mg to about 55 mg, about 75 mg to about 125 mg, about 80 mg to about 120 mg, 85 mg to about 115 mg, about 90 mg to about 110 mg, or about 95 mg to about 105 mg). In some aspects, the total amount of rifaximin (in milligrams) in the disclosed compositions ranges from about 10 mg to about 30 mg, about 15 mg to about 25 mg, about 30 mg to about 50 mg, about 35 mg to about 45 mg, about 70 mg to about 90 mg, or about 75 to about 85 mg, In some aspects, the total amount of rifaximin (in milligrams) in the disclosed compositions is about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, or about 125 mg, or about 126, or about 127, or about 128, or about 129, or about 130, or about 131, or about 132, or about 133, or about 134, or about 135, or about 140, or about 145, or about 150, or about 155, or about 160, or about 165, or about 170, or about 175, or about 180, or about 185, or about 190, or about 195, or about 200, or about 205, or about 210, or about 215, or about 220, or about 225, or about 230, or about 235, or about 240, or about 245, or about 250 mg; or at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100, at least about 101, at least about 102, at least about 103, at least about 104, at least about 105, at least about 106, at least about 107, at least about 108, at least about 109, at least about 110, at least about 111, at least about 112, at least about 113, at least about 114, at least about 115, at least about 116, at least about 117, at least about 118, at least about 119, at least about 120, at least about 121, at least about 122, at least about 123, at least about 124, or at least about 125, or at least about 126, or at least about 127, or at least about 128, or at least about 129, or at least about 130, or at least about 131, or at least about 132, or at least about 133, or at least about 134, or at least about 135, or at least about 140, or at least about 145, or at least about 150, or at least about 155, or at least about 160, or at least about 165, or at least about 170, or at least about 175, or at least about 180, or at least about 185, or at least about 190, or at least about 195, or at least about 200, or at least about 205, or at least about 210, or at least about 215, or at least about 220, or at least about 225, or at least about 230, or at least about 235, or at least about 240, or at least about 245, or at least about 250 mg; or is at most about 5, at most about 6, at most about 7, at most about 8, at most about 9, at most about 10, at most about 11, at most about 12, at most about 13, at most about 14, at most about 15, at most about 16, at most about 17, at most about 18, at most about 19, at most about 20, at most about 21, at most about 22, at most about 23, at most about 24, at most about 25, at most about 26, at most about 27, at most about 28, at most about 29, at most about 30, at most about 31, at most about 32, at most about 33, at most about 34, at most about 35, at most about 36, at most about 37, at most about 38, at most about 39, at most about 40, at most about 41, at most about 42, at most about 43, at most about 44, at most about 45, at most about 46, at most about 47, at most about 48, at most about 49, at most about 50, at most about 51, at most about 52, at most about 53, at most about 54, at most about 55, at most about 56, at most about 57, at most about 58, at most about 59, at most about 60, at most about 61, at most about 62, at most about 63, at most about 64, at most about 65, at most about 66, at most about 67, at most about 68, at most about 69, at most about 70, at most about 71, at most about 72, at most about 73, at most about 74, at most about 75, at most about 76, at most about 77, at most about 78, at most about 79, at most about 80, at most about 81, at most about 82, at most about 83, at most about 84, at most about 85, at most about 86, at most about 87, at most about 88, at most about 89, at most about 90, at most about 91, at most about 92, at most about 93, at most about 94, at most about 95, at most about 96, at most about 97, at most about 98, at most about 99, at most about 100, at most about 101, at most about 102, at most about 103, at most about 104, at most about 105, at most about 106, at most about 107, at most about 108, at most about 109, at most about 110, at most about 111, at most about 112, at most about 113, at most about 114, at most about 115, at most about 116, at most about 117, at most about 118, at most about 119, at most about 120, at most about 121, at most about 122, at most about 123, at most about 124, or at most about 125, or at most about 126, or at most about 127, or at most about 128, or at most about 129, or at most about 130, or at most about 131, or at most about 132, or at most about 133, or at most about 134, or at most about 135, or at most about 140, or at most about 145, or at most about 150, or at most about 155, or at most about 160, or at most about 165, or at most about 170, or at most about 175, or at most about 180, or at most about 185, or at most about 190, or at most about 195, or at most about 200, or at most about 205, or at most about 210, or at most about 215, or at most about 220, or at most about 225, or at most about 230, or at most about 235, or at most about 240, or at most about 245, or at most about 250 mg. In some aspects, the total amount of rifaximin (in milligrams) in the disclosed compositions is about 20 mg, or about 40 mg or about 80 mg. Elements from these embodiments may be combined with one or more of the additional embodiments and/or aspects described herein.

7. Application to Drugs Having Poor Aqueous Solubility

The present technology can also be applied to other therapeutic compounds which may benefit from targeted release to one or more of the upper, lower, or mid-GI tract. Such compounds include e.g., those which have poor aqueous solubility in one or more of the upper GI tract, mid-GI tract, and lower GI tract. In some embodiments, such compounds may be a rifamycin compound. In some embodiments, the rifamycin compound may be selected from the group consisting of rifaximin, rifamycin A, rifamycin B, rifamycin C, rifamycin D, rifamycin E, rifamycin S, rifamycin SV, rifampin (rifampicin), rifapentine, rifabutin, rifalazil, and pharmaceutically acceptable salts thereof. In some embodiments, the rifamycin compound is rifaximin.

Provided, therefore, is a composition for targeted release to one or more of the upper GI tract, mid-GI tract, and lower GI tract, comprising, as the case may be:

a. first targeted release beads comprising a sugar sphere coated with a combination comprising a rifamycin compound, a first pH independent polymer, and a second pH independent polymer, wherein the first targeted release beads are configured to release the rifamycin compound to the upper GI tract; and/or
b. second targeted release beads comprising a sugar sphere coated with a combination comprising a rifamycin compound and a pH dependent polymer, wherein the second targeted release beads are configured to release the rifamycin compound to the mid-GI tract, lower GI tract, and/or colon.

In some embodiments, the first pH independent polymer and the second pH independent polymer are selected from the group consisting of hydroxypropyl methylcellulose (HPMC), polyvinylpyrrolidone (PVP), hydroxyethyl cellulose (HEC) polyethylene glycol (PEG), polyvinyl alcohol (PVA), polyacrylic acid (PAA), hydroxypropyl cellulose, methyl cellulose, ethyl cellulose, and divinyl ether maleic anhydride copolymer (DIVEMA). In some embodiments, the first pH independent polymer is HPMC. In some embodiments, the second pH independent polymer is PVP.

In some embodiments, the pH dependent polymer is selected from the group consisting of hydroxypropyl methylcellulose acetate succinate (HPMC-AS), methacrylic/ethylacrylic copolymer, hydroxypropyl methylcellulose acetate phthalate (HPMC-P), cellulose acetate phthalate (CAP), and cellulose acetate trimellitate (CAT). In some embodiments, the pH dependent polymer is HPMC-AS.

In some embodiments, the first and/or second targeted release beads may include a surfactant. In some embodiments, the surfactant is a non-ionic surfactant. In some embodiments, the surfactant is poloxamer 407.

In some embodiments, the first and/or second targeted release beads may include a pharmaceutically acceptable plasticizer. In some embodiments, the pharmaceutically acceptable plasticizer is an alkyl citrate. In some embodiments, the pharmaceutically acceptable plasticizer is selected from triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), and trimethyl citrate (TMC). In some embodiments, the pharmaceutically acceptable plasticizer is TEC. In some embodiments, the first and/or second targeted release beads may include diethyl phthalate and/or dibutyl phthalate. In some embodiments, the first and/or second targeted release beads include diethyl phthalate.

In some embodiments, the second targeted release beads include an enteric coating. In some embodiments, the enteric coating surrounds the sugar sphere coated with the rifamycin compound and a pH dependent polymer. In some embodiments, the enteric coating comprises a methacrylic acid-acrylate copolymer and, optionally, a combination of glycerol monostearate, triethyl citrate, and polysorbate 80 (e.g., Plasacryl HTP 20). In some embodiments, the enteric coating comprises a methacrylic acid ethylacrylate copolymer (e.g., Eudragit L30D55) and, optionally, a combination of glycerol monostearate, triethyl citrate, and polysorbate 80 (e.g., Plasacryl HTP 20). In some embodiments, the enteric coating further comprises an anti-adherent additive.

In one embodiment, the first pH independent polymer is present in an amount of from about 5% to about 15% by weight based on the total weight of rifamycin compound in the composition. In some embodiments, the first pH independent polymer is present in an amount of from about 6% to about 12% by weight based on the total weight of rifamycin compound in the composition. In some embodiments, the first pH independent polymer is present in an amount of from about 6% to about 10% by weight based on the total weight of rifamycin compound in the combination. In some embodiments, the first pH independent polymer is present in an amount of from about 5% to about 9% by weight based on the total weight of rifamycin compound in the combination. In some embodiments, the first pH independent polymer is present in an amount of from about 5% to about 8% by weight based on the total weight of rifamycin compound in the combination. In some embodiments, the first pH independent polymer is present in an amount of from about 5% to about 7% by weight based on the total weight of rifamycin compound in the combination. In some embodiments, the first pH independent polymer is present in an amount of from about 6% to about 7% by weight based on the total weight of rifamycin compound in the combination. In some embodiments, the first pH independent polymer is present in an amount of from about 7% to about 10% by weight based on the total weight of rifamycin compound in the composition. In some embodiments, the first pH independent polymer is present in an amount of from about 8% to about 9% by weight based on the total weight of rifamycin compound in the composition. In some embodiments, the first pH independent polymer is present in an amount of from about 0.1% to about 2.5% by weight based on the total weight of the composition. In some embodiments, the first pH independent polymer is present in an amount of from about 0.3% to about 2.3% by weight based on the total weight of the composition. In some embodiments, the first pH independent polymer is present in an amount of from about 0.3% to about 0.5% or from about 1.8% to about 2.0% by weight based on the total weight of the composition. In some embodiments, the first pH independent polymer is present in an amount of from about 0.4% to about 0.5% or from about 1.9% to about 2.0% by weight based on the total weight of the composition.

In one embodiment, the second pH independent polymer is present in an amount of from about 15% to about 35% by weight based on the total weight of rifamycin compound in the combination. In some embodiments, the second pH independent polymer is present in an amount of from about 15% to about 25% by weight based on the total weight of rifamycin compound in the combination. In some embodiments, the second pH independent polymer is present in an amount of from about 15% to about 20% by weight based on the total weight of rifamycin compound in the combination. In some embodiments, the second pH independent polymer is present in an amount of from about 18% to about 20% by weight based on the total weight of rifamycin compound in the combination. In some embodiments, the second pH independent polymer is present in an amount of from about 19% to about 20% by weight based on the total weight of rifamycin compound in the combination. In some embodiments, the second pH independent polymer is present in an amount of from about 20% to about 35% by weight based on the total weight of rifamycin compound in the composition. In some embodiments, the second pH independent polymer is present in an amount of from about 25% to about 30% by weight based on the total weight of rifamycin compound in the composition. In some embodiments, the second pH independent polymer is present in an amount of from about 26% to about 27% by weight based on the total weight of rifamycin compound in the composition. In some embodiments, the second pH independent polymer is present in an amount of from about 0.5% to about 4.0% or from about 3.0% to about 8.0% by weight based on the total weight of the composition. In some embodiments, the second pH independent polymer is present in an amount of from about 0.5% to about 2.0% or from about 4.0% to about 7.0% by weight based on the total weight of the composition. In some embodiments, the second pH independent polymer is present in an amount of from about 0.1% to about 2.0% or from about 5.0% to about 6.0% by weight based on the total weight of the composition.

In one embodiment, the pH dependent polymer is present in an amount of from about 20% to about 60% by weight based on the total weight of rifamycin compound in the composition. In some embodiments, the pH dependent polymer is present in an amount of from about 20% to about 50% by weight based on the total weight of rifamycin compound in the composition. In some embodiments, the pH dependent polymer is present in an amount of from about 25% to about 45% by weight based on the total weight of rifamycin compound in the composition. In some embodiments, the pH dependent polymer is present in an amount of from about 30% to about 40% by weight based on the total weight of rifamycin compound in the composition. In some embodiments, the pH dependent polymer is present in an amount of from about 30% to about 35% by weight based on the total weight of rifamycin compound in the composition. In some embodiments, the pH dependent polymer is present in an amount of from about 40% to about 60% by weight based on the total weight of the rifamycin compound in the composition. In some embodiments, the pH dependent polymer is present in an amount of from about 40% to about 50% by weight based on the total weight of the rifamycin compound in the composition. In some embodiments, the pH dependent polymer is present in an amount of from about 43% to about 47% by weight based on the total weight of the rifamycin compound in the composition. In some embodiments, the pH dependent polymer is present in an amount of from about 44% to about 45% by weight based on the total weight of the rifamycin compound in the composition. In some embodiments, the pH dependent polymer is present in an amount of from about 1% to about 12% by weight based on the total weight of the rifamycin compound in the composition. In some embodiments, the pH dependent polymer is present in an amount of from about 1% to about 4% or from about 8% to about 11% by weight based on the total weight of the composition. In some embodiments, the pH dependent polymer is present in an amount of from about 1% to about 3% or from about 8% to about 10% by weight based on the total weight of the composition. In some embodiments, the pH dependent polymer is present in an amount of from about 2% to about 3% or from about 9% to about 10% by weight based on the total weight of the composition.

In one embodiment, the rifamycin compound to pH independent polymer in the compositions is provided in a weight ratio of about 65:35 to about 85:15, respectively. In some embodiments, the rifamycin compound to pH independent polymer in the compositions is provided in a weight ratio of about 70:30 to about 80:20, respectively. In some embodiments, the rifamycin compound to pH independent polymer in the compositions is provided in a weight ratio of about 70:30 to about 75:25, respectively. In some embodiments, the rifamycin compound and pH independent polymer, which may be included in the compositions described herein, are not provided in a weight ratio of 25:75, 50:50, or 75:25, respectively. In some embodiments, the compositions described herein include more rifamycin compound than pH independent polymer, by weight, when such compositions include both rifamycin compound and pH independent polymer.

In one embodiment, the rifamycin compound to pH dependent polymer in the compositions is provided in a weight ratio of about 65:35 to about 75:25, respectively. In some embodiments, the rifamycin compound to pH dependent polymer in the compositions is provided in a weight ratio of about 60:40 to about 70:30, respectively. In some embodiments, the rifamycin compound to pH dependent polymer in the compositions is provided in a weight ratio of about 65:35 to about 70:30, respectively. In some embodiments, the rifamycin compound and pH dependent polymer, which may be included in the compositions described herein, are not provided in a weight ratio of 25:75, 50:50, or 75:25, respectively. In some embodiments, the compositions described herein include more rifamycin compound than pH dependent polymer, by weight, when such compositions include both rifamycin compound and pH dependent polymer.

In one embodiment, the surfactant is present in an amount of from about 5% to about 15% by weight based on the total weight of the rifamycin compound in the composition. In some embodiments, the surfactant is present in an amount of from about 7% to about 9% by weight based on the total weight of rifamycin compound in the composition. In some embodiments, the surfactant is present in an amount of from about 8% to about 9% by weight based on the total weight of rifamycin compound in the composition.

In one embodiment, the rifamycin compound in the provided composition is present in an amount of from about 1% to about 30% by weight based on the total weight of the composition. In some embodiments, the rifamycin compound is present in an amount of from about 1% to about 10% by weight based on the total weight of the composition. In some embodiments, the rifamycin compound is present in an amount of from about 4% to about 6% by weight based on the total weight of the composition. In some embodiments, the rifamycin compound is present in an amount of from about 15% to about 25% by weight based on the total weight of the composition. In some embodiments, the rifamycin compound is present in an amount of from about 20% to about 23% by weight based on the total weight of the composition.

In some embodiments, the foregoing composition, which includes first and/or second targeted release beads, may include the rifamycin compound according to any of the following doses. In one embodiment, the total amount of rifamycin compound in the disclosed compositions is less than about 250 mg (e.g., less than about 240 mg, less than about 230 mg, less than about 220 mg, less than about 210 mg, less than about 200 mg, less than about 190 mg, less than about 180 mg, less than about 170 mg, less than about 160 mg, less than about 150 mg, less than about 140 mg, less than about 130 mg, less than about 120 mg, less than about 110 mg, less than about 100 mg, less than about 90 mg, less than about 80 mg, less than about 70 mg, less than about 60 mg, less than about 50 mg, less than about 40 mg, less than about 30 mg, less than about 20 mg, or less than about 10 mg). In some aspects, the total amount of rifamycin compound ranges from about 2.5 mg to about 250 mg (e.g., about 5 mg to about 250 mg, about 5 mg to about 200 mg, about 5 mg to about 150 mg, about 5 mg to about 125 mg, about 10 mg to about 125 mg, about 10 mg to about 100 mg, about 25 mg to about 125 mg, about 25 mg to about 100 mg, about 25 mg to about 75 mg, about 30 mg to about 70 mg, about 35 mg to about 65 mg, about 40 mg to about 60 mg, about 45 mg to about 55 mg, about 75 mg to about 125 mg, about 80 mg to about 120 mg, 85 mg to about 115 mg, about 90 mg to about 110 mg, or about 95 mg to about 105 mg). In some aspects, the total amount (in milligrams) of rifamycin compound in the disclosed compositions is about 5, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, or about 125 mg, or about 126 mg, or about 127 mg, or about 128 mg, or about 129 mg, or about 130 mg, or about 131 mg, or about 132 mg, or about 133 mg, or about 134 mg, or about 135 mg, or about 140 mg, or about 145 mg, or about 150 mg, or about 155 mg, or about 160 mg, or about 165 mg, or about 170 mg, or about 175 mg, or about 180 mg, or about 185 mg, or about 190 mg, or about 195 mg, or about 200 mg, or about 205 mg, or about 210 mg, or about 215 mg, or about 220 mg, or about 225 mg, or about 230 mg, or about 235 mg, or about 240 mg, or about 245 mg, or about 250 mg; or at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100, at least about 101, at least about 102, at least about 103, at least about 104, at least about 105, at least about 106, at least about 107, at least about 108, at least about 109, at least about 110, at least about 111, at least about 112, at least about 113, at least about 114, at least about 115, at least about 116, at least about 117, at least about 118, at least about 119, at least about 120, at least about 121, at least about 122, at least about 123, at least about 124, or at least about 125 mg, or at least about 126 mg, or at least about 127 mg, or at least about 128 mg, or at least about 129 mg, or at least about 130 mg, or at least about 131 mg, or at least about 132 mg, or at least about 133 mg, or at least about 134 mg, or at least about 135 mg, or at least about 140 mg, or at least about 145 mg, or at least about 150 mg, or at least about 155 mg, or at least about 160 mg, or at least about 165 mg, or at least about 170 mg, or at least about 175 mg, or at least about 180 mg, or at least about 185 mg, or at least about 190 mg, or at least about 195 mg, or at least about 200 mg, or at least about 205 mg, or at least about 210 mg, or at least about 215 mg, or at least about 220 mg, or at least about 225 mg, or at least about 230 mg, or at least about 235 mg, or at least about 240 mg, or at least about 245 mg, or at least about 250 mg; or is at most about 10, at most about 11, at most about 12, at most about 13, at most about 14, at most about 15, at most about 16, at most about 17, at most about 18, at most about 19, at most about 20, at most about 21, at most about 22, at most about 23, at most about 24, at most about 25, at most about 26, at most about 27, at most about 28, at most about 29, at most about 30, at most about 31, at most about 32, at most about 33, at most about 34, at most about 35, at most about 36, at most about 37, at most about 38, at most about 39, at most about 40, at most about 41, at most about 42, at most about 43, at most about 44, at most about 45, at most about 46, at most about 47, at most about 48, at most about 49, at most about 50, at most about 51, at most about 52, at most about 53, at most about 54, at most about 55, at most about 56, at most about 57, at most about 58, at most about 59, at most about 60, at most about 61, at most about 62, at most about 63, at most about 64, at most about 65, at most about 66, at most about 67, at most about 68, at most about 69, at most about 70, at most about 71, at most about 72, at most about 73, at most about 74, at most about 75, at most about 76, at most about 77, at most about 78, at most about 79, at most about 80, at most about 81, at most about 82, at most about 83, at most about 84, at most about 85, at most about 86, at most about 87, at most about 88, at most about 89, at most about 90, at most about 91, at most about 92, at most about 93, at most about 94, at most about 95, at most about 96, at most about 97, at most about 98, at most about 99, at most about 100, at most about 101, at most about 102, at most about 103, at most about 104, at most about 105, at most about 106, at most about 107, at most about 108, at most about 109, at most about 110, at most about 111, at most about 112, at most about 113, at most about 114, at most about 115, at most about 116, at most about 117, at most about 118, at most about 119, at most about 120, at most about 121, at most about 122, at most about 123, at most about 124, or at most about 125 mg, or at most about 126 mg, or at most about 127 mg, or at most about 128 mg, or at most about 129 mg, or at most about 130 mg, or at most about 131 mg, or at most about 132 mg, or at most about 133 mg, or at most about 134 mg, or at most about 135 mg, or at most about 140 mg, or at most about 145 mg, or at most about 150 mg, or at most about 155 mg, or at most about 160 mg, or at most about 165 mg, or at most about 170 mg, or at most about 175 mg, or at most about 180 mg, or at most about 185 mg, or at most about 190 mg, or at most about 195 mg, or at most about 200 mg, or at most about 205 mg, or at most about 210 mg, or at most about 215 mg, or at most about 220 mg, or at most about 225 mg, or at most about 230 mg, or at most about 235 mg, or at most about 240 mg, or at most about 245 mg, or at most about 250 mg.

8. Dosage Forms

For the purposes of administration, in certain embodiments, the compositions described herein may be administered as is or formulated as alternative dosage forms, e.g., for oral delivery. Formulations for oral delivery can be in the form of lozenges, aqueous or oily suspensions, emulsions, capsules, syrups, or elixirs. Orally administered compositions can comprise one or more optional agents, for example, sweetening agents such as fructose, aspartame or saccharin; flavoring agents such as peppermint, oil of wintergreen, or cherry; coloring agents; and preserving agents, to provide a pharmaceutically-palatable preparation. The compositions may be coated to delay disintegration and absorption in the gastrointestinal tract thereby providing a sustained action over an extended period of time.

In certain embodiments, the disclosed compositions are formulated in capsule dosage forms. In certain embodiments, the disclosed compositions are formulated in soft or hard capsule dosage forms. In certain embodiments, the disclosed compositions are formulated in soft or hard gelatin capsule dosage forms.

It should be noted that a specific dosage and treatment regimen for any particular patient will depend upon a variety of factors, including age, body weight, general health, sex, diet, time of administration, rate of excretion, drug combination, the judgment of the treating physician, and the severity of the particular disease being treated.

9. Antioxidants/Chelating Agents

In some embodiments, the compositions described herein may further comprise an antioxidant and/or a chelating agent.

In some embodiments, the compositions described herein further comprise an antioxidant and/or chelating agent selected from ascorbyl palmitate, butylated hydroxyanisole (BHA), butylated hydroxytoluene (BHT), citric acid, sodium metabisulfite, cysteine, potassium metabisulfite, propyl gallate, sodium thiosulfate, vitamin E (e.g., Vitamin E TPGS), and 3,4-dihydroxybenzoic acid. Without being limited to any one theory of the invention, BHT and citric acid, for example, may be used as antioxidants and/or chelating agents to minimize potential degradation of rifaximin via oxidation.

In some embodiments, the compositions described herein include an antioxidant and/or chelating agent in an amount of about 0.001% to about 3% by weight of the composition.

In some embodiments, the compositions described herein includes an antioxidant and/or chelating agent in an amount of about 0.05% to about 3%, or about 0.1% to about 3%, or about 0.1% to about 1%, or about 0.1% to about 0.5% by weight of the composition. In some embodiments, the compositions described herein includes an antioxidant and/or chelating agent in an amount of at least about 0.1%, 0.2%, 0.3%, 0.4%, 0.5%, 0.6%, 0.7%, 0.8%, 0.9%, 1%, 2%, or 3% by weight of the composition. In some embodiments, the compositions described herein includes an antioxidant and/or chelating agent in an amount of at most about 0.1%, 0.2%, 0.3%, 0.4%, 0.5%, 0.6%, 0.7%, 0.8%, 0.9%, 1%, 2%, or 3% by weight of the composition. In some embodiments, the compositions described herein includes an antioxidant and/or chelating agent in an amount of about 0.1%, 0.2%, 0.3%, 0.4%, 0.5%, 0.6%, 0.7%, 0.8%, 0.9%, 1%, 2%, or 3% by weight of the composition.

In some embodiments, the compositions described herein include BHA, BHT, and/or vitamin E TPGS in an amount of about 0.05% to about 3%, or about 0.1% to about 2%, or about 0.1% to about 1%, or about 0.1% to about 0.5% by weight of the composition. In some embodiments, the compositions described herein include BHA, BHT, and/or vitamin E TPGS in an amount of at least about 0.1%, 0.2%, 0.3%, 0.4%, 0.5%, 0.6%, 0.7%, 0.8%, 0.9%, 1%, 2%, or 3% by weight of the composition. In some embodiments, the compositions described herein include BHA, BHT, and/or vitamin E TPGS in an amount of at most about 0.1%, 0.2%, 0.3%, 0.4%, 0.5%, 0.6%, 0.7%, 0.8%, 0.9%, 1%, 2%, or 3% by weight of the composition. In some embodiments, the compositions described herein include BHA, BHT, and/or vitamin E TPGS in an amount of about 0.1%, 0.2%, 0.3%, 0.4%, 0.5%, 0.6%, 0.7%, 0.8%, 0.9%, 1%, 2%, or 3% by weight of the composition.

In some embodiments, the compositions described herein include BHA in an amount of about 0.05% to about 1%, or about 0.1% to about 0.5%, or about 0.1% to about 0.4%, or about 0.1% to about 0.3% by weight of the composition. In some embodiments, the compositions described herein include BHA in an amount of at least about 0.1%, or 0.2%, or 0.3%, or 0.4%, or 0.5% by weight of the composition. In some embodiments, the compositions described herein include BHA in an amount of at most about 0.1%, or 0.2%, or 0.3%, or 0.4%, or 0.5% by weight of the composition. In some embodiments, the compositions described herein include BHA in an amount of about 0.1%, or 0.2%, or 0.3%, or 0.4%, or 0.5% by weight of the composition.

In some embodiments, the compositions described herein include BHT in an amount of about 0.05% to about 1%, or about 0.1% to about 0.5%, or about 0.1% to about 0.4%, or about 0.1% to about 0.3% by weight of the composition. In some embodiments, the compositions described herein include BHT in an amount of at least about 0.1%, or 0.2%, or 0.3%, or 0.4%, or 0.5% by weight of the composition. In some embodiments, the compositions described herein include BHT in an amount of at most about 0.1%, or 0.2%, or 0.3%, or 0.4%, or 0.5% by weight of the composition. In some embodiments, the compositions described herein include BHT in an amount of about 0.1%, or 0.2%, or 0.3%, or 0.4%, or 0.5% by weight of the composition.

In some embodiments, the compositions described herein include vitamin E TPGS in an amount of about 0.1% to about 3%, or about 0.5% to about 3%, or about 0.5% to about 1%, or about 1% to about 3% by weight of the composition. In some embodiments, the compositions described herein include vitamin E TPGS in an amount of at least about 0.1%, 0.2%, 0.3%, 0.4%, 0.5%, 0.6%, 0.7%, 0.8%, 0.9%, 1%, 2%, or 3% by weight of the composition. In some embodiments, the compositions described herein include vitamin E TPGS in an amount of at most about 0.1%, 0.2%, 0.3%, 0.4%, 0.5%, 0.6%, 0.7%, 0.8%, 0.9%, 1%, 2%, or 3% by weight of the composition. In some embodiments, the compositions described herein include vitamin E TPGS in an amount of about 0.1%, 0.2%, 0.3%, 0.4%, 0.5%, 0.6%, 0.7%, 0.8%, 0.9%, 1%, 2%, or 3% by weight of the composition.

10. Methods and Uses

The compositions described herein may be used in methods for treating diseases. For example, the present disclosure includes a method of treating a disease or disorder in a subject in need thereof. Such methods may include the step of administering to said subject a therapeutically effective amount of one or more of any of the aforementioned compositions, which may be in unit dosage form.

The compositions described herein are useful in treating one or more disorders, including bowel related or liver function disorders. Such disorders include, for example, irritable bowel syndrome (IBS) (e.g., IBS-D), diarrhea, microbe associated diarrhea, infectious diarrhea, *Clostridium difficile* infections and symptoms (e.g., *Clostridium difficile* associated diarrhea), travelers' diarrhea, small intestinal bacterial overgrowth (SIBO), Crohn's disease, diverticular disease, pancreatitis (including chronic), pancreatic insufficiency, enteritis, colitis (e.g., ulcerative colitis, antibiotic associated colitis, and microscopic colitis), hepatic encephalopathy (or other diseases which lead to increased ammonia levels) and symptoms thereof, gastric dyspepsia, cirrhosis (e.g., alcoholic cirrhosis), polycystic liver disease, pouchitis, peritonitis, short bowel syndrome, inflammatory bowel disease, rosacea, sickle cell disease, and *H. pylori* infection.

The compositions described herein are useful for the treatment and/or prevention of hepatic encephalopathy. For example, the compositions described herein may be useful for the treatment of hepatic encephalopathy reoccurrence; and/or for the treatment of overt hepatic encephalopathy; and/or for the prevention of overt hepatic encephalopathy.

The compositions described herein are useful for liver transplant preparation.

The compositions described herein are useful in treating cardiovascular conditions (e.g., atherosclerotic cardiovascular disease).

The compositions described herein are useful in treating disorders which affect the central nervous system and those associated with cognitive impairment such as Parkinson's disease, Alzheimer's disease, and autism.

The compositions described herein are useful in treating certain cancers such as acute myeloid leukemia.

The compositions described herein are useful in treating sickle cell disease and/or symptoms associated therewith.

In an embodiment, the invention described herein includes a method of treating sickle cell disease (SCD) in a patient in need thereof comprising administering a disclosed targeted release composition to the patient. In some embodiments, the method of treating sickle cell disease (SCD) comprises reducing elevated levels of circulating aged neutrophils (CANs) in the patient. In some embodiments, the method of treating sickle cell disease (SCD) in a patient comprises treating vaso-occlusive crisis (VOC) in the patient.

In some embodiments, treating vaso-occlusive crisis (VOC) in the patient comprises (1) alleviating one or more symptoms of VOC in the patient; (2) reducing or preventing the occurrence of VOCs in the patient; (3) reducing the duration or severity of VOC in the patient; and/or (4) mediating or otherwise reducing the patient's opioid usage during VOC. In some embodiments, the method of treating sickle cell (SCD) in the patient comprises alleviating one or more symptoms of vaso-occlusive crisis (VOC) in the patient. In some embodiments, the method of treating sickle cell disease (SCD) in the patient comprises reducing or preventing the occurrence of vaso-occlusive crises (VOCs) in the patient. In some embodiments, the method of treating sickle cell disease (SCD) in the patient comprises reducing the duration or severity of VOC in the patient. In some embodiments, the method of treating sickle cell disease (SCD) in the patient comprises mediating or otherwise reducing the patient's opioid usage during vaso-occlusive crisis (VOC) in the patient. Without being limited to any one theory of the invention, the ER and DER bead formulations described herein are understood to have greater benefit to SCD patients as compared to XIFXAN® 550 mg tablets because (1) the ER and DER bead formulations provide for prolonged rifaximin exposure due in part to their release profile; (2) the ER and DER bead formulations have lower Cmax values with comparable systemic exposure (i.e., AUC); and (3) the ER and DER bead formulations have greater accumulation ratios with comparable systemic exposure (i.e., AUC).

In some embodiments, the rifaximin compositions described herein may be administered with an additional SCD therapeutic agent in the foregoing methods of treatment. In some embodiments, the additional SCD therapeutic agent may be, for example, hydroxyurea, L-glutamine, hydroxycarbamide, an erythropoietin stimulating agent, and/or an opioid analgesic. In some embodiments, the opioid analgesic may be selected from the group consisting of morphine, codeine, hydrocodone, hydromorphone, methadone, tramadol, oxycodone, tapentadol, fentanyl, and a combination thereof.

Provided are methods of treating one or more diseases or disorders described herein in a subject in need thereof, comprising administering to the subject a therapeutically effective amount of a disclosed composition. Also provided is the use of a disclosed composition for the manufacture of a medicament for treating one or more diseases or disorders described herein. Further provided is the use of a disclosed composition for treating one or more diseases or disorders described herein.

In accordance with the foregoing, the methods may include administering a composition described herein to provide a dose of a rifamycin compound, such as rifaximin, to a subject in an amount (in milligrams) of at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg. In some embodiments, such methods may include administering a composition described herein to provide a dose of a rifamycin compound, such as rifaximin, to a subject in an amount (in milligrams) of at most about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg. In some embodiments, such methods may include administering a composition described herein to provide a dose of a rifamycin compound, such as rifaximin, to a subject in an amount (in milligrams) of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg.

In accordance with the foregoing, the methods may include administering a composition described herein QD, BID, TID, or QID to provide a daily dose of a rifamycin compound, such as rifaximin, to a subject in an amount (in milligrams) of at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 mg. In some embodiments, the methods may include administering a composition described herein QD, BID, TID, or QID to provide a daily dose of a rifamycin compound, such as rifaximin, to a subject in an amount (in milligrams) of at most about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 mg. In some embodiments, the methods may include administering a composition described herein QD, BID, TID, or QID to provide a daily dose of a rifamycin compound, such as rifaximin, to a subject in an amount (in milligrams) of about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 mg.

In some embodiments, the methods may include administering a composition described herein QD, BID, TID, or QID to provide a daily dose of a rifamycin compound, such as rifaximin, to a subject in an amount (in milligrams) of about 20 mg, 40 mg, 80 mg, 120 mg, 160 mg, 200 mg, 240 mg, 280 mg, or 320 mg.

In some embodiments, the methods may include administering a composition described herein BID to provide a daily dose of a rifamycin compound, such as rifaximin, to a subject in an amount (in milligrams) of about 80 mg or about 160 mg.

For example, the methods may include BID administration of a unit dose of an ER bead or DER bead formulation, containing 40 mg of rifaximin, to a subject in need thereof to provide a daily dose of 80 mg of rifaximin.

In another example, the methods may include BID administration of a unit dose of an ER bead or DER bead formulation, containing 80 mg of rifaximin, to a subject in need thereof to provide a daily dose of 160 mg of rifaximin.

In some embodiments, the foregoing doses or daily doses may be provided by administering at least 1, 2, 3, 4, 5, 6, 7, 8, 9, or 10 unit dosage forms of the composition (e.g., capsules) to a subject per dose or per day, as the case may be. In some embodiments, the foregoing doses or daily doses may be provided by administering at most 1, 2, 3, 4, 5, 6, 7, 8, 9, or 10 unit dosage forms of the composition (e.g., capsules) to a subject per dose or per day, as the case may be. In some embodiments, the foregoing doses or daily doses may be provided by administering about 1, 2, 3, 4, 5, 6, 7, 8, 9, or 10 unit dosage forms of the composition (e.g., capsules) to a subject per dose or per day, as the case may be.

For example, the methods may include BID administration of 2 unit doses (capsules) of an ER bead or DER bead formulation, containing 20 mg of rifaximin each (i.e., 40 mg total), to a subject in need thereof to provide a daily dose of 80 mg of rifaximin.

In another example, the methods may include BID administration of 4 unit doses (capsules) of an ER bead or DER bead formulation, containing 20 mg of rifaximin each (i.e., 80 mg total), to a subject in need thereof to provide a daily dose of 160 mg of rifaximin.

While certain embodiments of the invention have been described and/or exemplified above, various other embodiments will be apparent to those skilled in the art from this disclosure. The invention is, therefore, not limited to the particular embodiments described and/or exemplified, but is capable of considerable variation and modification without departure from the scope and spirit of the appended claims.

Exemplification

The representative examples that follow are intended to help illustrate the present disclosure, and are not intended to, nor should they be construed to, limit the scope of the invention.

Example 1: Regional Bioavailability of Rifaximin

An open-label, 5-way non-randomized, single-sequence, crossover study in healthy male subjects was conducted to investigate the regional bioavailability of rifaximin when delivered to target sites within the gastrointestinal (GI) tract. In period 1, subjects received 150 mg rifaximin formulated as an immediate release (IR) solid dispersion capsule. Solid dispersion forms of rifaximin can be found, e.g., in WO 2018/064472, WO 2012/009388, U.S. Pat. Nos. 9,737,610, and 10,874,647, the entire contents of which are incorporated herein by reference. In period 2, subjects received 150 mg rifaximin formulated as an immediate release (IR) solid dispersion capsule to the proximal small bowel (PSB), distal small bowel (DSB), colon and mid small bowel (MSB). Blood samples were collected pre-dose and at specified time points after dosing for PK analysis.

Figure 1:
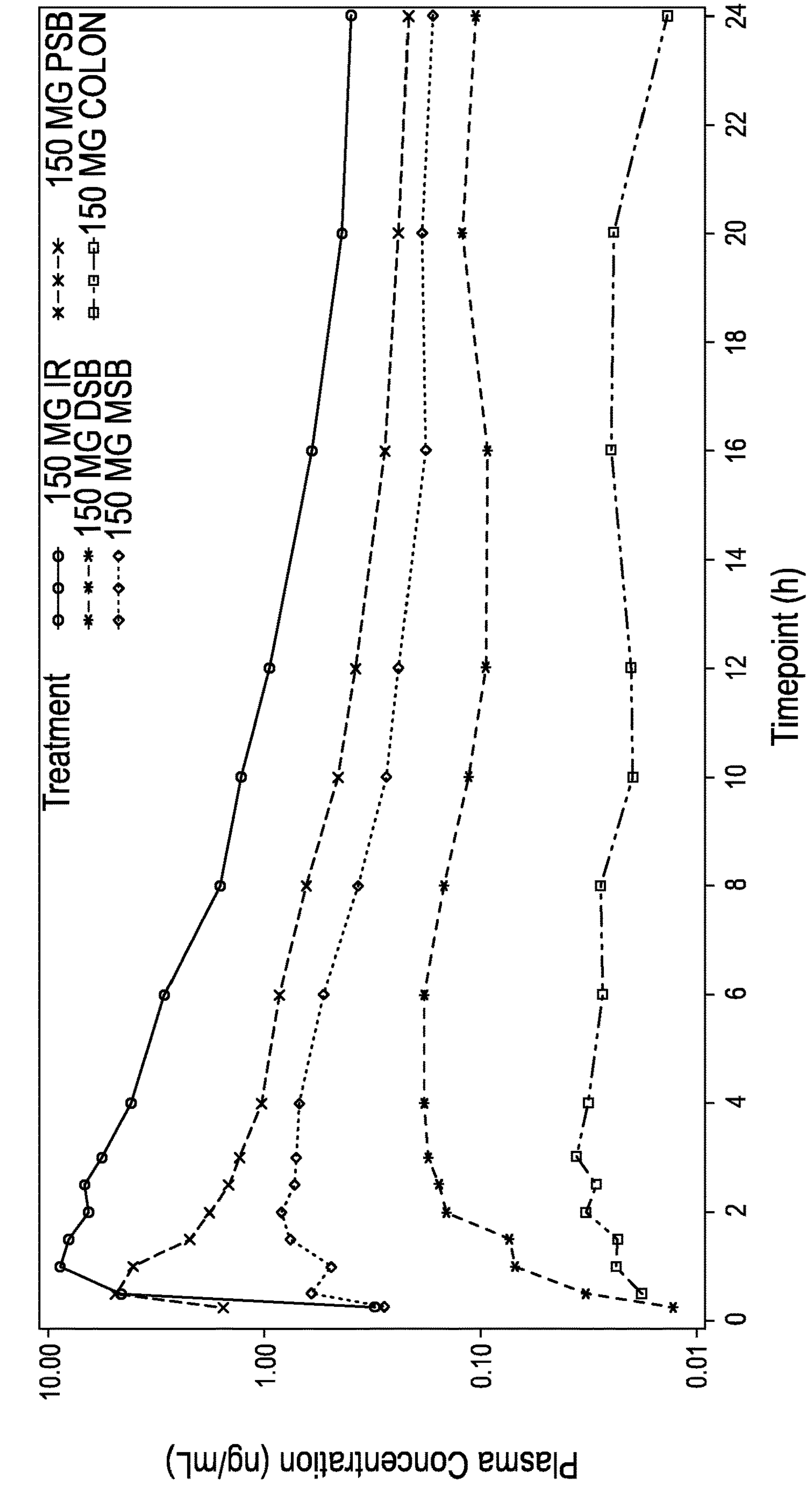
FIG. 1 shows the mean plasma concentration vs time profiles of rifaximin following regional administration of 150 mg of immediate release solid dispersion rifaximin capsules to the GI tract.

As shown by FIG. 1 and Table 1, the extent of rifaximin exposure was greatest following delivery to the proximal small bowel and declined with distance traveled along the intestinal tract. Absorption from the colon was negligible (the plasma samples provided by most subjects failed to contain quantifiable rifaximin following delivery to the colon). This trend was reflected in mean estimates of Frel which were 36.4%, 7.08%, 2.09% and 0.216% in the proximal, mid and distal small bowel.

TABLE 1

Geometric Mean (Geometric CV %) of Pharmacokinetic Parameters for Rifaximin Following Regional Administration of Rifaximin SSD to the GI Tract

| | Regimen | | | | |
|---|---|---|---|---|---|
| Parameter | A (N = 12) | B (N = 12) | C (N = 12) | D (N = 12) | E (N = 10) |
| $C_{max}$ (ng/mL) | 10.1 (67.0%) | 4.49 (82.8%) | 0.197 (128.4%) | 0.0719 (74.1%) | 0.544 (277.1%) |
| $t_{max}$ (h)[a] | 1.500 (0.50-4.00) | 0.500 (0.50-1.50) | 3.000 (1.00-24.00) | 3.000 (2.00-16.00) | 3.000 (0.25-24.00) |

TABLE 1-continued

Geometric Mean (Geometric CV %) of Pharmacokinetic Parameters for Rifaximin Following Regional Administration of Rifaximin SSD to the GI Tract

| Parameter | Regimen A (N = 12) | B (N = 12) | C (N = 12) | D (N = 12) | E (N = 10) |
|---|---|---|---|---|---|
| $t_{lag}$ (h)[a] | 0.250 (0.00-1.50) | 0.000 (0.00-0.25) | 1.500 (0.00-3.00) | 1.500 (0.25-12.00) | 0.125 (0.00-3.00) |
| $AUC_{0-24}$ or $AUC_{act-24}$ (ng · h/mL) | 41.499 (59.8%) | 15.119 (76.7%) | 0.86674 (1003.5%) | 0.10070 (318.7%) | 2.9366 (838.3%) |
| $AUC_{0-last}$ or $AUC_{act-last}$ (ng · h/mL) | 41.504 (59.8%) | 15.016 (80.2%) | 0.80581 (1205.1%) | 0.087671 (307.9%) | 2.9343 (837.5%) |
| Frel (%)[b] | — | 36.4 (45.9%) | 2.09 (686.6%) | 0.216 (318.2%) | 7.08 (446.7%) |

Regimen A: 150 mg rifaximin administered orally as 2 × 75 mg SSD IR capsules
Regimen B: 150 mg rifaximin SSD delivered to the proximal small bowel
Regimen C: 150 mg rifaximin SSD delivered to the distal small bowel
Regimen D: 150 mg rifaximin SSD delivered to the colon
Regimen E: 150 mg rifaximin SSD delivered to the mid small bowel
[a]median (range)
[b]based on comparisons of $AUC_{0-24}$ with $AUC_{act-24}$

Example 2: UGI and MGI Compositions

Two compositions were prepared according to the foregoing invention. A first composition was prepared as an upper GI targeted or ER formulation. The second composition was prepared as mid GI and/or lower GI targeted or DER formulation.

The upper GI (UGI) targeted, ER composition comprises a rifaximin layered sucrose sugar sphere where the rifaximin is non-crystalline and is encased in two polymers (Povidone K-90 and Hypromellose 2910) along with surfactant (Poloxamer 407) and a plasticizer (diethyl phthalate). The amount of rifaximin to accommodate various dosage amounts was adjusted accordingly. The beads were filled in hard opaque Swedish orange size OEL gelatin capsule shell. In particular, high and low drug load beads were prepared and examined.

The mid GI (MGI) targeted, DER composition comprises a rifaximin layered sucrose sugar sphere where the rifaximin is non-crystalline and is encased in an enteric polymer (Hypromellose acetate succinate) along with surfactant (poloxamer 407) and plasticizers (diethyl phthalate and triethyl citrate). The drug layered sphere is then coated with the methacrylic and ethylacrylate copolymer (Eudragit L30 D55) plasticized by Polysorbate 80 and triethylcitrate. Glycerol monostearate is included in the functional coating application as an anti-sticking agent. The amount of rifaximin to accommodate various dosage amounts was adjusted accordingly. The beads were filled in hard opaque Swedish orange size OEL gelatin capsule shell. As above, high and low drug load beads were prepared and examined.

Regarding dissolution, beads are designed to have an Extended Release profile (UGI Beads) where the release is pH independent. The MGI formulation is designed as a delayed release (no release at pH<4.5) and has an extended release profile when pH conditions reach pH 6.8.

Indeed, the UGI formulation is designed for pH independent extended release, where the majority of the drug is released over a period of 2-3 hours. The rifaximin release from this dosage form is intended to be delivered in the upper portions of the gastrointestinal tract, where pH may vary from 1 to 6 as the bead migrates through the stomach, duodenum and jejunum segments. The amount released can be modulated by increasing the dose. Doubling the dose from 20 mg to 40 mg doubles the amount released.

Experimental UGI formulations containing different ratios of HPMC AS to Povidone K90, established that HPMC AS containing formulations do not produce the preferred pH independent drug release. Such formulations produced slower dissolution at lower pH. Without being limited to any one theory, this behavior is attributed to characteristics of the HPMC-AS polymer which requires higher pH to ionize and hydrate. Additionally, such formulations exhibited relatively slow release. To match drug release with small intestine transit time, faster release was targeted where 60-80% of drug is released in 2-3 hours. Therefore, HPMC-AS was not preferred for use in UGI formulations and HPMC was developed as a preferred polymer in such formulations.

In summary, the polymer selection for the UGI formulation dissolution behavior was important from both a dissolution and a processing perspective. Povidone K90 was identified as a preferred polymer to produce satisfactory drug layering properties. Incorporating HPMC-AS into the Povidone polymer system did not offer the desired release properties for the UGI bead, as this polymer has some "enteric" properties and does not hydrate well at pH<6. The dissolution profiles in these formulation studies also demonstrated that hypromellose may offer some solubility enhancement or inhibition of rifaximin precipitation, helping to keep the rifaximin solubilized.

Incorporation of hypromellose into the bead composition produced beads where rifaximin release was more pH independent. Composition studies further supported the lower level, or ~25% of the total polymer being hypromellose and the remainder being povidone K90 as producing suitable beads. Higher concentrations of the hypromellose were produced on a development scale, however, since hypromellose has poor solubility in the methanol solvent used for the drug layer steps, lower concentrations of hypromellose were desired to ensure the polymer was in solution to allow for more molecular interaction of rifaximin with the polymer, plus avoid any solids in the spray solution that could lead to processing challenges (nozzle clogging or non-homogeneous polymer deposition).

Other factors evaluated included sugar sphere size and drug loading to determine its impact on release. Sugar sphere sizes from the 14/18 mesh (largest), 20/25 mesh (middle) and 30/35 mesh (smallest) were evaluated in batches, 4224-120, 3669154 and 4224-155, respectively. Dissolution profiles conducted at pH 4.5 for the UGI formulations demonstrated drug release increases as sugar sphere size decreases. This is expected because at constant dose, smaller bead sizes have larger surface area. For the UGI formulation, the 20/25 mesh spheres were selected since processing with small sugar spheres have increased processing risks (sticking/twinning). Moreover, the lower drug loaded beads exhibit faster release, where at such dose levels (i.e. 5% rifaximin drug load), >80% of the drug is released within 1-2 hrs compared to the higher drug load formulations (i.e., 22% rifaximin drug load), where less than 50% is released within the same timeframe.

With regard to the MGI formulation, it was designed to release rifaximin to the mid sections of the intestinal tract, specifically the jejunum and ileum. The drug release profile is achieved using several compositional design features. First, the drug layered bead is formulated to contain HPMC-AS, which is an enteric polymer designed to hydrate at around pH 6. Secondly, the bead is coated with methacrylic acid ethylacrylate copolymer (Eudragit L30 D55). The pH sensitive properties of this polymer protect the bead when exposed to low pH and do not permit hydration of the coating. When pH conditions approach 5.5, the polymer will begin to hydrate, dissolve and allow for the internal bead to release drug.

Furthermore, studies on the MGI formulation demonstrated that HPMC-AS was preferential over a povidone/HPMC based system. The grade of HPMC-AS was found to be relevant since M grade provided improved performance as compared to H grade with respect to attrition during processing. Additionally, the MGI formulation benefited from the use of a solubilizing enteric polymer as opposed to a water-insoluble enteric polymer with pH dependent hydration properties (e.g., Eudragit RL/RS). Furthermore, drug loading was demonstrated to play a role in release profile where lower drug loading led to faster release rates for the same dose.

Examples of the UGI and MGI compositions are set forth in Tables 2-4, below.

TABLE 2

| | ER (UGI) | | DER (MGI) | |
|---|---|---|---|---|
| | 5 mg Strength mg/capsule | 10 mg Strength mg/capsule | 5 mg Strength mg/capsule | 10 mg Strength mg/capsule |
| Rifaximin | 5 | 10 | 5 | 10 |
| Hypromellose | 0.439 | 0.877 | | |
| Hypromellose acetate succinate | | | 2.234 | 4.469 |
| Povidone | 1.333 | 2.667 | | |
| Poloxamer | 0.421 | 0.842 | 0.425 | 0.851 |
| Diethyl Phthalate | 0.316 | 0.632 | 0.316 | 0.633 |
| TEC (triethyl citrate) | | | 0.648 | 1.296 |
| Methanol | | | | |
| Sugar Spheres | 92.491 | 184.982 | 74.709 | 149.418 |
| Methacrylic acid ethylacrylate copolymer | | | 8.418 | 16.835 |
| Glycerol monostearate, triethylcitrate, and polysorbate 80 combination | | | 0.842 | 1.684 |
| Total fill weight (mg) | 100.000 | 200.000 | 92.593 | 185.185 |

TABLE 3

| | ER (UGI) | | DER (MGI) | |
|---|---|---|---|---|
| | 20 mg Strength mg/capsule | 100 mg Strength mg/capsule | 20 mg Strength mg/capsule | 100 mg Strength mg/capsule |
| Rifaximin | 20 | 100 | 20 | 100 |
| Hypromellose | 1.754 | 8.772 | | |
| Hypromellose acetate succinate | | | 8.938 | 44.688 |
| Povidone | 5.333 | 26.667 | | |
| Poloxamer | 1.684 | 8.421 | 1.702 | 8.508 |
| Diethyl Phthalate | 1.263 | 6.316 | 1.266 | 6.328 |
| TEC (triethyl citrate) | | | 2.593 | 12.964 |
| Methanol | | | | |
| Sugar Spheres | 60.874 | 304.370 | 48.836 | 244.179 |
| Methacrylic acid ethylacrylate copolymer | | | 8.418 | 42.088 |
| Glycerol monostearate, triethylcitrate, and polysorbate 80 combination | | | 0.842 | 4.209 |
| Total fill weight (mg) | 90.909 | 454.545 | 92.593 | 462.963 |

Example 3: In Vitro Dissolution Studies for UGI and MGI Compositions

Figure 2:
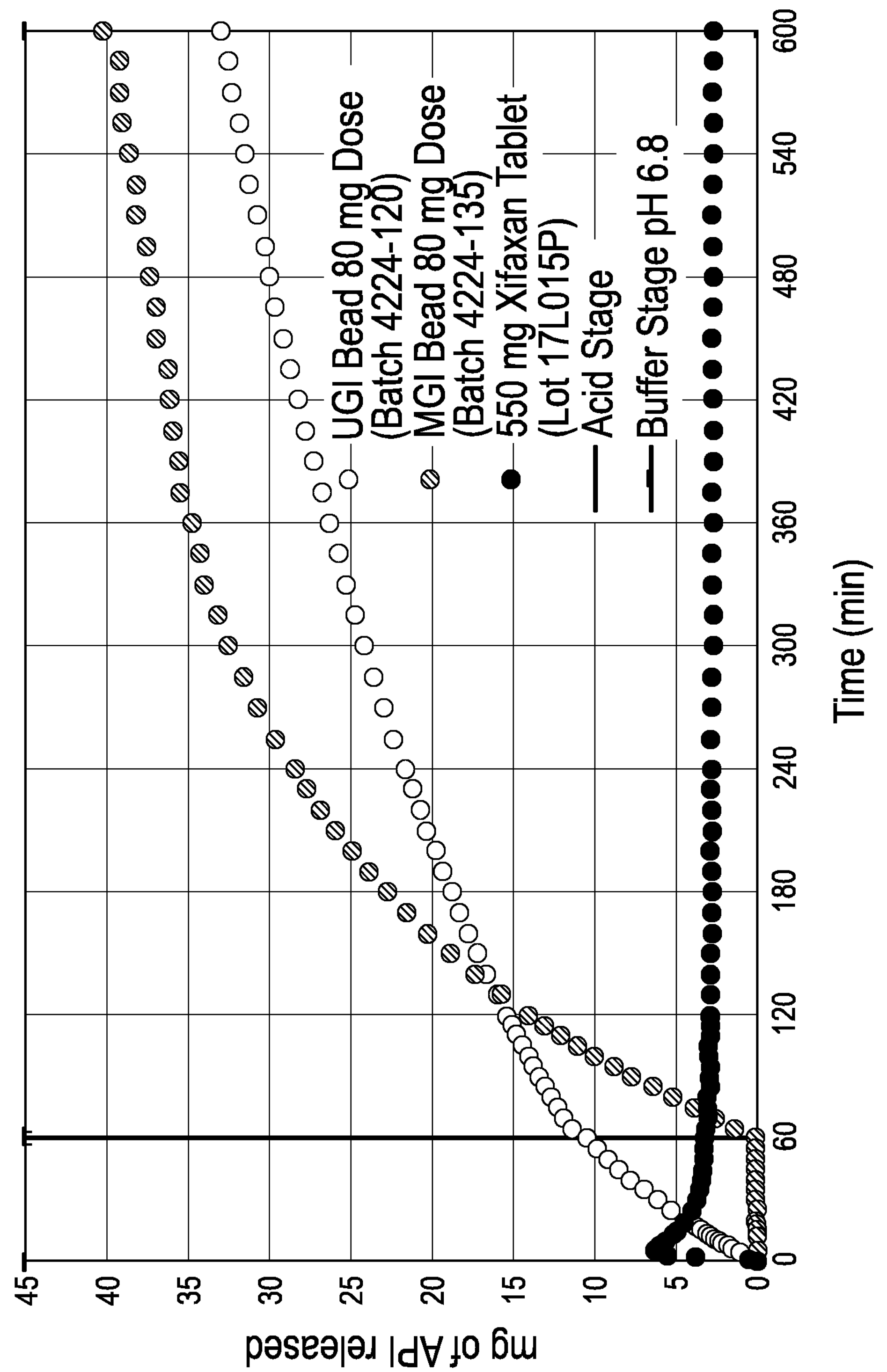
FIG. 2 shows the dissolution profile of inventive MGI and UGI compositions under acid and basic conditions compared with a 550 mg XIFXAN® tablet.

FIG. 2. shows the dissolution profile of 80 mg strength MGI and UGI compositions under acid and basic conditions compared with a 550 mg XIFAXAN® tablet. The data from this figure establishes the pH dependent nature of the rifaximin MGI delivery compositions (e.g., it is designed as a delayed release (no release at pH<4.5) and has an extended release profile when pH conditions reach pH 6.8) and the pH independent nature of the UGI composition. The 550 mg XIFAXAN® tablet has essentially negligible release across both acidic and buffered conditions compared to the inventive compositions.

Example 4: In Vivo Pharmacokinetic Studies for UGI and MGI Compositions

Male and female dogs were pretreated with pentagastrin to stimulate gastric acid secretion and better mimic human stomach pH. The dogs were administered a 200 mg strength UGI composition, a 200 mg strength MGI composition, or a 550 mg Xifaxin tablet. The mean PK parameters ($C_{max}$, AUC) are about 10-fold higher for 200 mg strength inventive UGI (labeled IR bead) and MGI (labeled ER-DC-5.5 bead) targeted composition compared to XIFAXAN® 550 tablet. When dose normalized, about a 25-fold difference in $AUC_{0-24}$ was found between inventive UGI and MGI compositions and XIFAXAN® 550 tablet drug absorption See e.g., FIG. 3.

Figure 4:
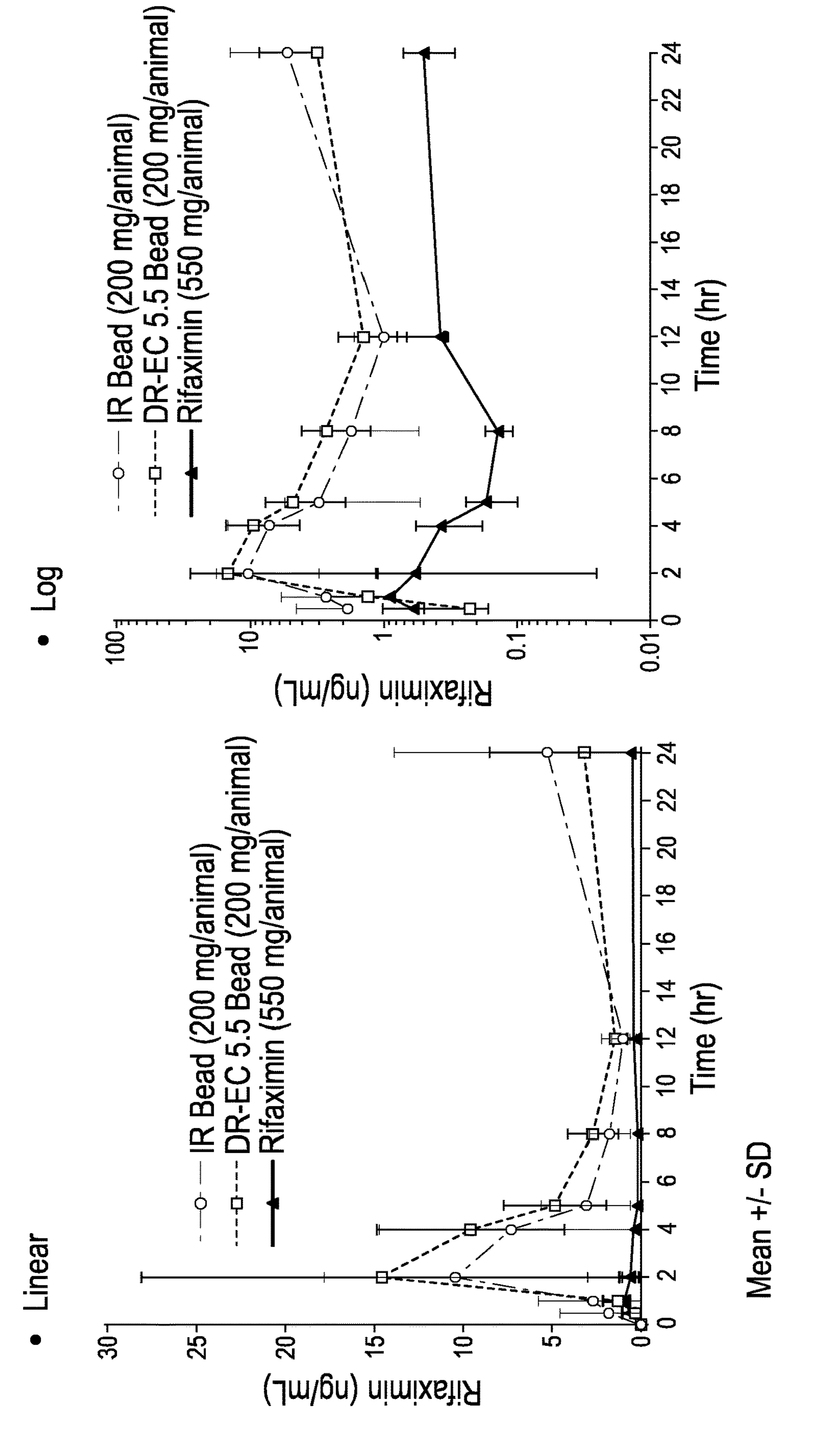
FIG. 4 shows the rifaximin plasma concentration as a function of time for dogs treated with inventive MGI and UGI compositions as compared with rifaximin.

FIG. 4 shows the rifaximin plasma concentration as a function of time. The MGI composition (labeled ER-DC-5.5 bead) has delayed release for about the Pt hour indicating the absence or minimal dissolution in the upper GI tract. The UGI composition (labeled IR bead) shows earlier release indicative of its pH independent design.

Example 5: Randomized, Placebo-Controlled Study to Evaluate the Safety, Tolerability, and Pharmacokinetics of Novel Rifaximin Formulations in Healthy Volunteers A Phase 1, randomized, placebo-controlled, safety, tolerability, and PK study for disclosed 10 mg, 40 mg, and 80 mg rifaximin ER and DER compositions was conducted in healthy volunteers. The study was broken down into two phases: a Single Ascending Dose (SAD) Phase and a Multiple-Dose (MD) Phase.

A. Single Ascending Dose (SAD)

For the SAD study, four single doses were tested: a low-dose, a mid-dose, a high-dose, and a maximum dose (BID administration of the high-dose for 1 day). The single day BID dose is included in the SAD Phase to provide safety data on a single maximum BID dose to support the selection of the BID dose to be evaluated in the Multiple Dose Phase. 2 cohorts were enrolled for each composition and enrollment was staggered, with appropriate safety evaluations and washout periods to expedite the dose escalation. Participants were randomized in a 6:2 ratio (active:placebo) within each of the following 6 dose-escalating cohorts. Participants maintained their initial randomization (active or placebo) throughout the SAD Phase.

Formulation 2: Rifaximin ER Capsule
- Cohort 1: Low-dose (10 mg rifaximin) then high-dose (80 mg rifaximin)
- Cohort 2: Mid-dose (40 mg rifaximin) then max dose (80 mg rifaximin BID)

Formulation 3: Rifaximin DER Capsule
- Cohort 1: Low-dose (10 mg rifaximin) then high-dose (80 mg rifaximin)
- Cohort 2: Mid-dose (40 mg rifaximin) then max dose (80 mg rifaximin BID)

B. Multiple Ascending Dose (MAD)

Within approximately 2 weeks after completion of the SAD Phase, determination for proceeding to the MAD Phase was made for each formulation, and the appropriate dose for BID dosing was selected based on the safety, tolerability, and PK data. For formulations continuing into the MD Phase, the safety, tolerability, and PK of 14 days of BID dosing was evaluated. Eight (8) new participants were randomized (6 active:2 placebo) into Cohort 3 for each formulation as follows:

Formulation 1: Rifaximin ER Capsule
- Cohort 3: 80 mg BID

Formulation 2: Rifaximin DER Capsule
- Cohort 3: 80 mg BID

Results

A. Serious Adverse Events (SAEs) and Treatment-Adverse Events (TEAEs)

There were no SAEs or TEAEs with a severity≥Grade 3 (i.e., severe) reported for the ER compositions with the majority of TEAEs reported being Grade 1 (minor). For the DER composition, there were no SAEs, TEAEs with a severity≥Grade 3 (i.e., severe), or TEAEs leading to study drug withdrawal or discontinuation from the study reported for the DER compositions. All TEAEs reported for the DER compositions were Grade 1 (mild). Similar results were observed for the MAD study.

B. Pharmacokinetics

SAD Dose Rifaximin ER Composition

Administration of the ER composition resulted in similar rifaximin concentrations for 10 mg and 40 mg within 5 hours of dosing (median $T_{max}$ ranged from 2.5 to 3.5 hours) (Table 4). Peak rifaximin concentrations occurred over a broader range (up to 5 hours post-dose) for low, mid, high, and max ER dose levels. BID dosing (2×80 mg) resulted in a greater than proportional increase in rifaximin exposure for $AUC_{last}$ (18.9 h·ng/mL) and $AUC_{inf}$ (19.5 h·ng/mL) relative to high 80 mg ER ($AUC_{last}$ and $AUC_{inf}$ were 6.78 and 7.05 h·ng/mL, respectively) (Table 5). The tin following administration of the ER formulation (5.9 to 13 hours), although variable (% CV up to 38%) indicated that sufficient plasma levels were available to adequately determine the terminal elimination phase. Following the max 80 mg BID ER formulation, considerably higher mean rifaximin levels were observed after administration of the second dose (approximately 1.1 ng/mL) than after the first dose (approximately 0.4 ng/mL).

TABLE 4

| Dose Form | $T_{max}$ (h) | $C_{max}$ (ng/mL) | $AUC_{last}$ (h * ng/mL) | $AUC_{inf}$ (h * ng/mL) | $t_{1/2}$ (h) | Cl/F (L/h) |
|---|---|---|---|---|---|---|
| low 10 mg | 2.5 | 0.3167 | 2.425 | 2.649 | 5.924 | 3775 |
| | (1.00-5.00) | (55.1%) | (66.4%) | (58.5%) | (20.3%) | (58.5%) |
| mid-40 mg | 3.5 | 0.3063 | 3.640 | 3.991 | 13.07 | 10020 |
| | (1.50-5.00) | (38.7%) | (13.9%) | (13.0%) | (32.0%) | (13.0%) |

TABLE 4-continued

| Dose Form | $T_{max}$ (h) | $C_{max}$ (ng/mL) | $AUC_{last}$ (h * ng/mL) | $AUC_{inf}$ (h * ng/mL) | $t_{1/2}$ (h) | Cl/F (L/h) |
|---|---|---|---|---|---|---|
| high 80 mg | 3.00 (2.00-5.00) | 0.7443 (53.8%) | 6.787 (53.1%) | 7.082 (51.2%) | 9.980 (38.3%) | 11300 (51.2%) |
| max 80 mg BID | 18.0 (14.0-24.0) | 1.111 (35.7%) | 18.91 (28.3%) | 19.52 (26.8%) | 10.68 (24.5%) | 27120 (20.4%) |

SAR Dose Rifaximin DER Composition

Administration of DER showed an increase in mean rifaximin concentration (Cmax) according to the following rank order: 10 mg (0.22 ng/mL)<40 mg (0.36 ng/mL)<80 mg (0.65 ng/mL)<80 mg BID (0.72 ng/mL; Table 5). The t1/2 following administration of the DER formulation (9.7 to 15.7 hours), although variable (geometric % CV up to 33%), was similar to that obtained for the ER composition.

TABLE 5

| Dose Form | $T_{max}$ (h) | $C_{max}$ (ng/mL) | $AUC_{last}$ (h * ng/mL) | $AUC_{inf}$ (h * ng/mL) | $t_{1/2}$ (h) | Cl/F (L/h) |
|---|---|---|---|---|---|---|
| low 10 mg | 5.00 (5.00, 8.00) | 0.2203 (86.4%) | 2.319 (54.4%) | 3.066 (35.9%) | 14.92 (20.1%) | 3262 (35.9%) |
| mid-40 mg | 5.00 (3.00, 10.00) | 0.3559 (47.4%) | 4.276 (39.7%) | 4.736 (33.6%) | 13.69 (25.3%) | 8447 (33.6%) |
| high 80 mg | 5.00 (5.00, 8.00) | 0.6481 (69.7%) | 7.170 (44.5%) | 6.926 (46.4%) | 15.71 (25.9%) | 11550 (46.4%) |
| max 80 mg BID | 7.50 (5.00-18.0) | 0.718 (61.4%) | 15.29 (36.2%) | 16.28 (37.3%) | 9.763* (32.6%) | 20490 (54.1%) |

MAD Dose Rifaximin ER Composition

Following administration of Rifaximin ER composition, a short lag time was observed (median 0.25 hours) on Day 1, before Cmax was achieved at approximately 2 hours post-dose, whereas on Day 14, Cmax was approximately 3.5 hours with zero lag time. On Day 14, higher mean rifaximin plasma concentration levels were observed (Day 14: 1.33 ng/mL) compared to Day 1 (0.82 ng/mL) with absorption phases to 6 hours. Where it was possible to determine, t1/2 on Day 1 was an underestimate at 3.6 hours (n=3), but when determined on Day 14, t1/2 of 17.9 hours reflected the potential for accumulation over time (Table 6A and 6B). Trough rifaximin plasma concentrations were approximately 0.5 ng/mL. Comparison of $C_{max}$ (Day14/Day1) indicated a modest mean accumulation ratio of 1.6 (% CV 79%) which was likely affected by an observed 2-step absorption phase occurring at 1.5 and 5 hours post-first dose. However, when determined using $AUC_{0-12}$ (Day 14/Day 1), the dependence upon time was reduced and as such, formulation specific characteristics were a more accurate ratio was determined at 2.0 (CV 55%) (Table 7).

MAD Dose Rifaximin DER Composition

Following administration of rifaximin DER capsules, a marginally longer median Tlag was observed (1 hour) on Day 1 (Table 6A and 6B). In addition, Day 1 Cmax and AUC parameters were lower than those observed for ER (Table 6A and 6B). By Day 14, however, Cmax and AUC had reached a steady state level which was approximately 5-fold higher than those observed on Day 1. Mean (% CV) Cavg was 0.138 ng/mL (37.4%) on Day 1 and 0.594 ng/mL (18.2%) on Day 14 which confirmed an accumulation. Trough rifaximin levels on Days 4 to 13 were approximately 0.5 ng/mL. Accumulation ratio for DER was 4.1 and 4.3 for Cmax and AUCtau, respectively (Table 7).

By comparison to 80 mg ER (BID) and 80 mg DER (BID) pharmacokinetics, XIFAXAN® 550 mg tablets (TID) have been shown to display, at Day 14 in healthy patients, a Cmax of 2.39±1.28 ng/mL, a Tmax of 5.63±5.27 h, and an AUCtau of 9.3±2.7 ng·hr/mL.

TABLE 6A

| Dose Form | Dosing Day | $C_{max}$ (ng/mL) | $T_{max}$ (h) | $T_{lag}$ (h) | $C_{avg}$ (ng/mL) | $t_{1/2}$ (h) |
|---|---|---|---|---|---|---|
| ER Rifaximin (80.0 mg BID, n = 6) | 1 | 0.8226 (58.4%) | 2.00 (1.00-5.00) | 0.25 (0.0-0.25) | 0.354 (35.0%) | 3.605 (7.7%) |
| | 14 | 1.328 (43.7%) | 3.50 (1.00-6.00) | 0.00 (0.00-0.00) | 0.717 (55.3%) | 17.975 (46.3%) |
| DER Rifaximin (80 mg BID, n = 6) | 1 | 0.264 (39.8%) | 5.00 (3.00-12.00) | 1.00 (0.25-3.00) | 0.138 (37.4%) | 4.839 |
| | 14 | 1.086 (32.3%) | 5.00 (1.00-5.00) | 0.00 (0.00-0.00) | 0.594 (18.2%) | 20.334 (34.6%) |

TABLE 6B

| Dose Form | Dosing Day | $AUC_{0-12}$ (h*ng/mL) | $AUC_{inf}$ (h*ng/mL) | $C_{max}$/D (ng/mL/mg) | $AUC_{inf}$/D (h*ng/mL/mg) |
|---|---|---|---|---|---|
| ER Rifaximin (80.0 mg BID, n = 6) | 1 | 4.253 (35.0%) | 6.058 (37.8%) | 0.010 (58.4%) | 0.076 (37.8%) |
| | 14 | 8.610 (55.3%) | 14.710 (48.8%) | 0.017 (43.7%) | 0.184 (48.8%) |
| DER Rifaximin (80 mg BID, n = 6) | 1 | 1.661 (37.4%) | 2.763 | 0.003 (39.8%) | 0.035 |
| | 14 | 7.134 (18.2%) | 16.770 (21.8%) | 0.014 (32.3%) | 0.210 (21.8%) |

TABLE 7

| Dose Form | Ratio $C_{max}$ d 14/$C_{max}$ d 1 | Ratio $AUC_{tau}$ d 14/$AUC_{0-12}$ d 1 |
|---|---|---|
| ER Rifaximin (80.0 mg BID, n = 6) | 1.6 (78.8%) | 2.0 (54.8%) |
| DER Rifaximin (80 mg BID, n = 6) | 4.1 (47.7%) | 2.0 (54.8%) |

Example 6: Exemplary Anti-Oxidant Containing Rifaximin ER and DER Compositions In addition to the foregoing, Tables 8-14 include high BHA, low BHA, and TPGS containing rifaximin ER and DER formulations.

TABLE 8

Exemplary High BHA Rifaximin DER Formulation

| Component | Function | Amount per capsule (mg) | % w/w |
|---|---|---|---|
| Rifaximin | Active | 80 | 20.71% |
| Hypromellose Acetate Succinate | Enteric polymer | 35.752 | 9.25% |
| Poloxamer 407 | Surfactant | 6.808 | 1.76% |
| Diethyl Phthalate | Plasticizer | 5.064 | 1.31% |
| Triethyl Citrate | Plasticizer | 10.372 | 2.68% |
| BHA | Antioxidant | 16 | 4.14% |
| Sugar Spheres | Filler/substrate | 195.344 | 50.56% |
| Eudragit L 30D 55 (methacrylic acid ethyl acrylate copolymer) | Enteric Polymer | 33.672 | 8.71% |
| Plasacryl HTP 20 (glycerol monostearate, triethyl citrate, polysorbate 80) | Plasticizer | 3.368 | 0.87% |
| Methanol | Processing Aid | 0.000* | * |
| Purified Water | Processing Aid | 0.000* | * |
| Size 0 EL Swedish Orange hard gelatin Capsule (Bovine/Porcine gelatin-Red Iron Oxide, Titanium dioxide) | Capsule | 106 mg | Not applicable |
| Total Weight of formulation | | 386.38 | 100.00% |

TABLE 9

Exemplary Low BHA Rifaximin DER Formulation

| Component | Function | Amount per capsule (mg) | % w/w |
|---|---|---|---|
| Rifaximin | Active | 80.000 | 21.51% |
| Hypromellose Acetate Succinate | Enteric polymer | 35.752 | 9.61% |
| Poloxamer 407 | Surfactant | 6.808 | 1.83% |
| Diethyl Phthalate | Plasticizer | 5.064 | 1.36% |
| Triethyl Citrate | Plasticizer | 10.372 | 2.79% |
| BHA | Antioxidant | 1.600 | 0.43% |
| Sugar Spheres | Filler/substrate | 195.344 | 52.51% |
| Eudragit L 30D 55 (methacrylic acid ethyl acrylate copolymer) | Enteric Polymer | 33.672 | 9.05% |
| Plasacryl HTP 20 (glycerol monostearate, triethyl citrate, polysorbate 80) | Plasticizer | 3.368 | 0.91% |
| Methanol | Processing Aid | 0.000* | * |
| Purified Water | Processing Aid | 0.000* | * |
| Size 0 EL Swedish Orange hardgelatin Capsule (Bovine/Porcine gelatin-Red Iron Oxide, Titanium dioxide) | Capsule | 106 mg | Not applicable |
| Total Weight of formulation | | 371.980 | 100.00% |

TABLE 10

Exemplary TPGS Rifaximin DER Formulation

| Component | Function | Amount per capsule (mg) | % w/w |
|---|---|---|---|
| Rifaximin | Active | 80.000 | 21.48% |
| Hypromellose Acetate Succinate | Enteric polymer | 35.752 | 9.60% |
| Poloxamer 407 | Surfactant | 6.808 | 1.83% |
| Diethyl Phthalate | Plasticizer | 5.064 | 1.36% |
| Triethyl Citrate | Plasticizer | 10.372 | 2.79% |
| Vitamin E TPGS | Antioxidant | 2.000 | 0.54% |
| Sugar Spheres | Filler/substrate | 195.344 | 52.46% |
| Eudragit L 30D 55 (methacrylic acid ethyl acrylate copolymer) | Enteric Polymer | 33.672 | 9.04% |
| Plasacryl HTP 20 (glycerol monostearate, triethyl citrate, polysorbate 80) | Plasticizer | 3.368 | 0.90% |
| Methanol | Processing Aid | 0.000* | * |
| Purified Water | Processing Aid | 0.000* | * |
| Size 0 EL Swedish Orange hard gelatin Capsule (Bovine/Porcine gelatin-Red Iron Oxide, Titanium dioxide) | Capsule | 106 mg | Not applicable |
| Total Weight of formulation | | 372.380 | 100.00% |

TABLE 11

| Exemplary TPGS Rifaximin DER Formulation | | | |
|---|---|---|---|
| Component | Function | Amount per capsule (mg) | % w/w |
| Rifaximin | Active | 80.000 | 21.78% |
| Hypromellose Acetate Succinate | Enteric polymer | 35.752 | 9.73% |
| Poloxamer 407 | Surfactant | 6.808 | 1.85% |
| Diethyl Phthalate | Plasticizer | | 0.00% |
| Triethyl Citrate | Plasticizer | 10.372 | 2.82% |
| Vitamin E TPGS | Antioxidant | 2.000 | 0.54% |
| Sugar Spheres | Filler/substrate | 195.344 | 53.18% |
| Eudragit L 30D 55 (methacrylic acid ethyl acrylate copolymer) | Enteric Polymer | 33.672 | 9.17% |
| Plasacryl HTP 20 (glycerol monostearate, triethyl citrate, polysorbate 80) | Plasticizer | 3.368 | 0.92% |
| Methanol | Processing Aid | 0.000* | * |
| Purified Water | Processing Aid | 0.000* | * |
| Size 0 EL Swedish Orange hard gelatin Capsule (Bovine/Porcine gelatin-Red Iron Oxide, Titanium dioxide) | Capsule | 106 mg | Not applicable |
| Total Weight of formulation | | 367.316 | 100.00% |

TABLE 12

| Exemplary High BHA Rifaximin ER Formulation | | | |
|---|---|---|---|
| Component | Function | Amount per capsule (mg) | % w/w |
| Rifaximin | Active | 80 | 21.76% |
| Hypromellose | Solubilizer | 7.016 | 1.91% |
| Povidone | Stabilizer | 21.332 | 5.80% |
| Poloxamer 407 | Surfactant | 6.736 | 1.83% |
| Diethyl Phthalate | Plasticizer | 5.052 | 1.37% |
| BHA | antioxidant | 4 | 1.09% |
| Sugar Spheres | Filler/substrate | 243.496 | 66.23% |
| Methanol | Processing Aid | 0.000* | * |
| Size 0 EL Swedish Orange hard gelatin Capsule (Bovine/Porcine gelatin-Red Iron Oxide, Titanium dioxide) | Capsule | 106 mg | Not applicable |
| Total Weight of formulation | | 367.632 | 100.00% |

TABLE 13

| Exemplary Low BHA Rifaximin ER Formulation | | | |
|---|---|---|---|
| Component | Function | Amount per capsule (mg) | % w/w |
| Rifaximin | Active | 80 | 21.98% |
| Hypromellose | Solubilizer | 7.016 | 1.93% |
| Povidone | Stabilizer | 21.332 | 5.86% |
| Poloxamer 407 | Surfactant | 6.736 | 1.85% |
| Diethyl Phthalate | Plasticizer | 5.052 | 1.39% |
| BHA | antioxidant | 0.4 | 0.11% |
| Sugar Spheres | Filler/substrate | 243.496 | 66.89% |

TABLE 13-continued

| Exemplary Low BHA Rifaximin ER Formulation | | | |
|---|---|---|---|
| Component | Function | Amount per capsule (mg) | % w/w |
| Methanol | Processing Aid | 0.000* | * |
| Size 0 EL Swedish Orange hard gelatin Capsule (Bovine/Porcine gelatin-Red Iron Oxide, Titanium dioxide) | Capsule | 106 mg | Not applicable |
| Total Weight of formulation | | 364.032 | 100.00% |

TABLE 14

| Exemplary TPGS Rifaximin ER Formulation | | | |
|---|---|---|---|
| Component | Function | Amount per capsule (mg) | % w/w |
| Rifaximin | Active | 80 | 21.41% |
| Hypromellose | Solubilizer | 7.016 | 1.88% |
| Povidone | Stabilizer | 21.332 | 5.71% |
| Poloxamer 407 | Surfactant | 6.736 | 1.80% |
| Diethyl Phthalate | Plasticizer | 5.052 | 1.35% |
| Vitamin E TPGS | antioxidant | 10 | 2.68% |
| Sugar Spheres | Filler/substrate | 243.496 | 65.17% |
| Methanol | Processing Aid | 0.000* | * |
| Size 0 EL Swedish Orange hard gelatin Capsule (Bovine/Porcine gelatin-Red Iron Oxide, Titanium dioxide) | Capsule | 106 mg | Not applicable |
| Total Weight of formulation | | 373.632 | 100.00% |

Example 7: Proposed Randomized, Double-Blind, Placebo-Controlled Study to Characterize the Safety, Efficacy, Pharmacokinetics, and Pharmacodynamics of Rifaximin Compositions in Sickle Cell Disease Patients with Vaso-Occlusive Crisis The purpose of this study is to evaluate the safety, efficacy, and pharmacokinetics of rifaximin after oral administration of one or more of the disclosed rifaximin compositions disclosed herein in sickle cell disease (SCD) patients with history of vaso-occlusive crisis (VOC). Any potential pharmacokinetic-pharmacodynamic (PK/PD) relationship between rifaximin systemic exposure and potential biomarkers of microbially-associated induction of VOC will also be evaluated. Previous clinical studies have shown rifaximin treatment (i.e., XIFAXAN® 550 mg tablets) to have potential benefit in reducing the number of VOCs and use of intravenous opioid analgesia (IOA). One possible explanation of this benefit may be due to modulation of intestinal microbial composition in SCD patients. Significant elevation of circulating aged neutrophils (CANs), with high CXCR4 and low CD62L surface expression, has been observed during VOCs and has been implicated in the development of the condition. It is proposed that this may occur in response to increased translocation of intestinal bacteria and bacterial products, which may be controlled with the administration of rifaximin.

This study will evaluate the safety, efficacy, and PK of rifaximin in SCD patients, as well as PK/PD relationships between rifaximin and several putative biomarkers associated with the proposed mechanism.

Objectives

The primary objective of this study is to assess the efficacy of the disclosed composition(s) in reducing VOCs in SCD patients.

Secondary objectives of this study are: (1) assessment of efficacy of the disclosed composition(s) in reducing subcategories of VOCs in SCD patients; (2) assessment of the disclosed composition(s) impact on IOA usage during VOC; (3) assessment of the disclosed composition(s)impact on outpatient opioid usage; (4) assessment of safety and tolerability of the disclosed composition(s) in SCD patients; and (5) characterization of PK and the PK/PD relationships between the disclosed rifaximin compositions tested herein and potential biomarkers of microbially-associated VOCs.

Endpoints

The primary efficacy endpoint of this study will be measured by the annualized rate of VOCs (overall and leading to healthcare visits).

The secondary efficacy endpoints of this study will be measured by the annualized rate of VOCs by subcategory (overall and leading to healthcare visits); the annualized rate of SCD-associated medical facility visits and/or hospitalization visits; and the duration of SCD-associated medical facility visits and/or hospitalization visits.

The secondary endpoint of impact on IOA use for this study is measured by the annualized rate of days using IOA; the time to readiness-for-discharge from first use of IOA during VOC; cumulative IOA consumption during VOC; and time to discontinuation of IOA use during VOC.

The secondary endpoint of assessment of the rifaximin composition's impact on outpatient opioid usage is measured in MME units.

The secondary endpoint of safety is measured by AEs, vital signs, and clinical labs.

The secondary endpoint of PK (rifaximin and 25-desacetyl rifaximin in plasma) is measured by subjects with intensive PK sampling (Day 1): $C_{max}$, $T_{max}$, $AUC_{last}$, $AUC_{0-12}$, $AUC_{inf}$, λz, $t_{1/2}$, CL/F, Vz/F, $MR_{\_AUCinf}$; subjects with intensive PK sampling (Day 29): $C_{trough}$, $C_{max,ss}$, $T_{max,ss}$, $AUC_{tau}$, $C_{ss,av}$ λz, $t_{1/2}$, $CL/F_{ss}$, $Vz/F_{ss}$, $R_{AUC}$, $R_{Cmax}$, $MR\_AUC_{tau}$; and subjects with sparse sampling: (Day 1, Day 8 [±1 day], Day 15 [±1 day], Day 29 [±1 day], Month 3, and Month 6): $C_{trough}$, $C_{max}$, AUC.

The secondary PD endpoint is measured by number and change from predose on Day 1 (at Day 8 [±1 day], Day 15 [±1 day], Day 29 [±1 day], Month 3, and Month 6) for total neutrophils and CANs, serum CD62L, urine 3-indoxyl sulfate, LPS, zonulin, serum citrulline, intestinal fatty-acid binding protein (iFABP).

The secondary PK/PD endpoint will be measured by evaluating the PK/PD relationships between rifaximin PK and each PD endpoint.

Proposed exploratory endpoints include use of a FANLTC questionnaire; examination of relative taxonomic abundance of fecal microbiota at baseline (screening window), Day 29, and Month; examination of iFABP levels; evaluation of CAN levels; evaluation of Zonulin levels; and evaluation of serum LPS levels.

Patient Population

SCD Patients that have experienced at least 1 VOC in the 12 months prior to enrollment.

Key Inclusion and Exclusion Criteria

Inclusion Criteria:

- Give informed consent.
- Has SCD of any genotype (HbSS, HbSC, HbS β-thalassemia).
- 18 to 70 years of age (inclusive) on day of consent.
- Experienced at least 1 VOC within the preceding 12 months prior to Screening. Prior VOC should include occurrence of appropriate symptoms, visit to medical facility and/or healthcare professional, receipt of parenteral opioid or NSAID analgesia or oral opioid.
- If receiving hydroxyurea or hydroxycarbamide (HU/HC) or erythropoietin stimulating agents, patient must have been receiving treatment for at least 6 months prior to Screening and plan to maintain the same dose and schedule during the study.
- Must meet the following lab values at screening:
  - Absolute Neutrophil Count≥$1.0\times10^9$/L
  - Platelets≥$75\times10^9$/L
  - Hemoglobin (Hgb)≥4.0 g/dL
  - Glomerular filtration rate≥45 mL/min/1.73 $m^2$ using CKD-EPI formula
  - Direct (conjugated) bilirubin≤2.0×ULN
  - Alanine transaminase (ALT)≤3.0×ULN
  - INR≥2.0
- ECOG performance status<2

Exclusion Criteria:

- History of stem cell transplant.
- Acute VOC ending within 7 days prior to Day 1 dosing.
- Received any blood products within 30 days of Day 1 dosing.
- Uncontrolled liver disease or renal insufficiency, colitis, or inflammatory bowel disease.
- Received active treatment on another investigational trial or has taken penicillin prophylaxis or antibiotics for treatment of infection within 30 days or 5 half-lives of the treatment, whichever is greater, prior to screening.
- Significant medical condition that requires hospitalization (other than SCD with VOC) within 2 months prior to screening.
- Participating in a chronic transfusion program (pre-planned series of transfusions for prophylactic purposes).
- Planning on undergoing an exchange transfusion during the duration of the study; episodic transfusion in response to worsened anemia or VOC is permitted.
- Hypersensitivity to rifaximin, rifampin, rifamycin antimicrobial agents, or any components of the rifaximin composition.
- Use of therapeutic anticoagulation (prophylactic doses permitted) or antiplatelet therapy (other than aspirin or NSAIDs) within the 10 days prior to Day 1 dosing.
- Pregnant or nursing women.
- Women of child-bearing potential, defined as all women physiologically capable of becoming pregnant, unless tested negative by serum pregnancy test at screening and agrees to standard prevention methods.
- History of drug abuse, documented or in opinion of investigator.
- Requirement for use of any medications on the prohibited medications list (CYP3A4 inhibitors/inducers, PPIs, PgP substrates).
- Any prior gastrointestinal surgery which has altered the anatomy of the esophagus, stomach, or small/large intestine (exceptions include appendectomy, cholecystectomy, and fundoplication).
- Colonoscopy or sigmoidoscopy, or any other use of bowel prep, laxative, or enema, within 30 days prior to Day 1 or plans to undergo such a procedure during the duration of the study.

Any documented history of clinical stroke or intracranial hemorrhage, or an uninvestigated neurologic finding within the 12 months prior to screening. Silent infarct only present on imaging is allowed.

Patients with bleeding disorders.

Planning to undergo a major surgical procedure during the duration of the study

Positive for HIV or other concomitant immunodeficiency.

Active Hepatitis B infection (HBsAg positive). Prior infection but not active (i.e., anti-HBc positive, HBsAg and HBV-DNA negative) is allowed.

Positive for Hepatitis C (HCV RNA). Prior infection with spontaneous resolution or sustained resolution after antiviral treatment (i.e., no detectible HCV RNA) for ≥6 months (with IFN-free treatments) or for ≥12 months (with use of IFN treatment) after cessation of antivirals are allowed.

Malignant disease. Exceptions include malignancies that were treated curatively and have not recurred within 2 years prior to study treatment, completely resected basal cell and squamous cell skin cancers, and any completely resected carcinoma in situ.

Serious mental or physical illness which, in the opinion of the Investigator, would compromise participation in the study.

Any condition which, in the opinion of the Investigator, is likely to interfere with the successful collection of the measurements required for the study.

Resting QTcF≥470 msec at screening.

Cardiac or cardiac repolarization abnormality, including any of the following:

- History of myocardial infarction (MI) angina pectoris, coronary artery bypass graft (CABG), or uncontrolled congestive heart failure within 6 months prior to Day 1.
- Clinically significant cardiac arrhythmias (e.g., ventricular tachycardia), complete left bundle branch block, high-grade AV block (e.g., bifascicular block, Mobitz type II and third-degree AV block).
- Long QT syndrome, family history of idiopathic sudden death or congenital long QT syndrome, or any of the following:
  - Risk factors for Torsade de Pointes (TdP) including uncorrected hypokalemia or hypomagnesemia, history of cardiac failure, or history of clinically significant/symptomatic bradycardia.
  - Concomitant medications with a known risk of TdP that cannot be discontinued or replaced by safe alternative (within 5 half-lives prior to starting study drug).
  - Inability to determine the QTcF interval.

Not able to understand or comply with study instructions and requirements.

For subjects in intensive PK group, subjects with hepatic impairment (Child-Pugh Class A, B, or C) should be excluded.

Subject Assessments

Efficacy assessments to be made include:

Number of VOCs during treatment and history thereof for 12 months prior to treatment. Crises identified by trial investigators will be adjudicated in a blinded fashion by an independent crisis-review committee.

Number of VOCs by subcategory (uncomplicated pain crisis, acute chest syndrome, hepatic sequestration, splenic sequestration, priapism) during treatment and history thereof for 12 months prior to treatment. Crises identified by trial investigators will be adjudicated in a blinded fashion by an independent crisis-review committee.

Number of SCD-associated hospitalization and ER visits during treatment and history thereof for 12 months prior to treatment.

Date and time for each start and stop of IOA use during VOCs.

Duration of hospitalization during each VOC, date/time of first use of IOA, and date/time of readiness-for-discharge.

Cumulative consumption of IOAs during each VOC during treatment and history thereof for 12 months prior to treatment.

Cumulative time of IOA usage during each VOC.

Safety and tolerability assessments include AEs, vital signs, clinical labs, and ECGs.

Other assessments include:

Functional Analysis of Non-life-Threatening Conditions (FANLTC) questionnaire predose on Day 1, at Day 29, 3 months, and 6 months.

Stool sample for microbiome profiling during screening window, at Day 29 and at 6 Months.

PK assessments will be provided as follows:

For intensive PK Subjects (Day 1 & Day 29): Predose, 0.5, 1, 1.5, 2, 3, 4, 5, 8, and 12 hr post dose (12 hr timepoint should be prior to second dose). For all other scheduled visits, predose and up to 3 additional post-dose samples (TBD by pharmacometrician).

For subjects with Sparse Sampling: Predose and up to 3 additional post-dose samples (TBD by pharmacometrician) on Day 1, Day 8, Day 15, Day 29, Month 3, and Month 6.

For all subjects: During medical facility visit for VOC with estimated time of last dose, when possible.

Dosing diary kept with time of dose recorded.

PD assessments will be provided as follows:

Predose on Day 1, during Day 8, Day 15, Day 29, Month 3, and Month 6 visits, and during medical facility visit for VOC when possible:

- Neutrophil markers: Total Neutrophils (Count and % WBC), CANs (Count and % Neutrophils), Serum CD62L.
- Gut permeability markers: Zonulin, serum citrulline, iFABP.
- Gut bacteria markers: LPS, Urine 3-indoxyl sulfate.

Data Analysis

The primary efficacy end point is the annual rate of VOC, which will be calculated as follows: total number of adjudicated VOC×365÷(end date-date of randomization+1), with the end date defined as the date of the last dose plus 14 days. The difference in the annual VOC rate for each rifaximin group versus the placebo group will be analyzed with a Wilcoxon rank-sum test, stratified by use of categorized history of crises in the previous year (<5; >=5 POV).

Change from Baseline in rate of VOCs, days using IOA, SCD-associated hospitalization and ER events and duration will be summarized by treatment and compared to placebo.

Time to readiness-for-discharge from first use of IOAs during each VOC and time to discontinuation of IOA use during VOCs will be summarized by treatment group with descriptive statistics and presented as Kaplan-Meier plots.

Cumulative use of IOA consumption during VOCs will be summarized by treatment group with descriptive statistics and compared to placebo.

AEs to be summarized by MedDRA System Organ Class (SOC) and Preferred Term (PT) and reported by treatment group and relationship to treatment. Observed and Change from Baseline in Vital Signs, labs, and ECG parameters (RR, PR, QTcF, QRS)

PK will be evaluated in intensive PK subjects using noncompartmental analysis. A population PK model will be developed using data from all subjects providing quantifiable post-dose samples. Steady-state will be assessed for all subjects using C trough measurements on Day 8, Day 15, and Day 29, and may be simulated using the population PK model.

PD endpoints will be summarized by treatment with quantity and change from baseline at each visit.

Relationship between rifaximin PK parameters and each PD endpoint will be evaluated using ANOVA models. A population PK/PD model may be developed as a separate analysis if warranted.

Change from Baseline in FANLTC questionnaire scores will be summarized by treatment and compared to placebo.

Change from Baseline in intestinal microbiome composition may be summarized by treatment and compared to placebo.

Example 8: Proposed Phase 1b Randomized, Double-Blind, Placebo-Controlled Study to Characterize the Pharmacokinetics and Pharmacodynamics of Rifaximin Novel Formulations in Patients with Sickle Cell Disease The objectives of this study are to characterize the pharmacokinetic properties of rifaximin ER and DER in subjects with sickle cell disease (SCD), to assess the safety and tolerability of rifaximin ER and DER, and to assess the response to treatment of pharmacodynamic markers associated with VOCs including total neutrophils, CANs, serum CD62L, the gut permeability biomarker iFABP, and the gut bacteria biomarker urine 3-indoxyl sulfate.

Subjects will be enrolled and randomized 2:2:1:2:2:1 to one of the following 6 parallel dosing arms to receive oral treatment twice daily (BID) for approximately 29 days:

Group 1: 40 mg rifaximin ER, BID
Group 2: 40 mg rifaximin DER, BID
Group 3: Placebo for 40 mg rifaximin, BID
Group 4: 80 mg rifaximin ER, BID
Group 5: 80 mg rifaximin DER, BID
Group 6: Placebo for 80 mg rifaximin, BID The foregoing dosing arms recited herein may be provided as follows:

40 mg rifaximin ER, BID (may be provided as single 40 mg rifaximin ER capsules BID or, alternatively, as two 20 mg rifaximin ER capsules BID);

40 mg rifaximin DER, BID (may be provided as single 40 mg rifaximin DER capsules BID or, alternatively, as two 20 mg rifaximin DER capsules BID);

80 mg rifaximin ER, BID (may be provided, alternatively, as single 80 mg rifaximin ER capsules BID, as four 20 mg rifaximin ER capsules BID, or as two 40 mg rifaximin ER capsules BID); and 80 mg rifaximin DER, BID (may be provided, alternatively, as single 80 mg rifaximin DER capsules BID, as four 20 mg rifaximin DER capsules BID, or as two 40 mg rifaximin DER capsules BID).

The rifaximin ER capsules for use in this study may be described as a controlled release solid oral dosage form for oral administration designed to deliver rifaximin to the proximal small bowel. The formulation contains drug and polymer layered beads in a hard gelatin capsule (bovine and/or porcine). The drug product contains 20 mg of the active ingredient, rifaximin, and the following inactive ingredients: Sucrose, gelatin, hypromellose, povidone, poloxamer 407, diethyl phthalate, titanium dioxide and iron oxide.

The rifaximin DER capsules for use in this study may be described as a controlled release solid oral dosage form for oral administration designed to target delivery of rifaximin to the mid small bowel. The formulation contains drug and polymer layered beads with an enteric coating in a hard gelatin capsule (bovine and/or porcine). The drug product contains 20 mg of the active ingredient, rifaximin, and the following inactive ingredients: Sucrose, gelatin, hypromellose acetate succinate, methacrylic acid and ethyl acrylate copolymer, poloxamer 407, glycerol monostearate, triethyl citrate, diethyl phthalate, polysorbate 80, titanium dioxide and iron oxide.

The subject population will include male and non-pregnant, non-nursing females of 18 to 70 years with SCD and at least 2 VOCs in the previous 12 months.

Subject participation will be up to 9 weeks, including a Screening Period of up to 21-days, a 4-week Treatment Period, and 2-week Follow-up. Outcomes will be assessed.

The contents of all references (including literature references, issued patents, published patent applications, and co-pending patent applications) cited throughout this application are hereby expressly incorporated herein in their entireties by reference.

Further Embodiments

Embodiment 1. A rifaximin delivery composition for use in a unit dosage form comprising a plurality of first targeted release rifaximin beads and a plurality of second targeted release rifaximin beads, wherein the first targeted release rifaximin beads comprise a sugar sphere coated with a combination comprising rifaximin, HPMC, and PVP; and the second targeted release rifaximin beads comprise a sugar sphere coated with a combination comprising rifaximin and HPMC-AS, and wherein the first and second targeted release rifaximin beads are configured to release rifaximin at different locations in a subject's gastrointestinal tract.

Embodiment 2. The rifaximin delivery composition of embodiment 1, further comprising a surfactant.

Embodiment 3. The rifaximin delivery composition of embodiment 1 or 2, further comprising a non-ionic surfactant.

Embodiment 4. The rifaximin delivery composition of any one of embodiments 1 to 3, further comprising poloxamer 407.

Embodiment 5. The rifaximin delivery composition of any one of embodiments 1 to 4, further comprising at least one pharmaceutically acceptable plasticizer and/or at least one agent selected from the group consisting of ascorbyl palmitate, butylated hydroxyanisole (BHA), butylated hydroxytoluene (BHT), citric acid, sodium metabisulfite, cysteine, potassium metabisulfite, propyl gallate, sodium thiosulfate, vitamin E (e.g., Vitamin E TPGS), and 3,4-dihydroxybenzoic acid.

Embodiment 6. The rifaximin delivery composition of embodiment 5, wherein the at least one pharmaceutically acceptable plasticizer is selected from an alkyl citrate and a phthalate, or a combination thereof.

Embodiment 7. The rifaximin delivery composition of embodiment 5 or 6, wherein the at least one pharmaceutically acceptable plasticizer is selected from triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), trimethyl citrate (TMC), diethyl phthalate or dibutyl phthalate.

Embodiment 8. The rifaximin delivery composition of any one of embodiments 5 to 7, wherein the at least one pharmaceutically acceptable plasticizer is selected form TEC and diethyl phthalate, or a combination thereof.

Embodiment 9. The rifaximin delivery composition of any one of embodiments 5 to 8, wherein the at least one pharmaceutically acceptable plasticizer is TEC.

Embodiment 10. The rifaximin delivery composition of any one of embodiments 5 to 8, wherein the at least one pharmaceutically acceptable plasticizer is a combination of TEC and diethyl phthalate.

Embodiment 11. The rifaximin delivery composition of any one of embodiments 1 to 10, further comprising an enteric coating.

Embodiment 12. The rifaximin delivery composition of any one of embodiments 1 to 11, further comprising an enteric coating surrounding the sugar sphere coated with a combination comprising rifaximin and HPMC-AS of the second targeted release beads.

Embodiment 13. The rifaximin delivery composition of embodiment 11 or 12 wherein the enteric coating comprises a methacrylic acid-acrylate copolymer.

Embodiment 14. The rifaximin delivery composition of any one of embodiments 11 to 13, wherein the enteric coating comprises an anionic methacrylic acid-acrylate copolymer.

Embodiment 15. The rifaximin delivery composition of any one of embodiments 11 to 14, wherein the enteric coating comprises copolymers of methacrylic acid and ethylacrylate.

Embodiment 16. The rifaximin delivery composition of any one of embodiments 11 to 15, wherein the enteric coating further comprises an anti-adherent additive.

Embodiment 17. The rifaximin delivery composition of any one of embodiments 1 to 16, wherein the rifaximin of the combination of the first targeted release beads is crystalline, non-crystalline, and/or amorphous.

Embodiment 18. The rifaximin delivery composition of any one of embodiments 1 to 16, wherein the rifaximin of the combination of the second targeted release beads is crystalline, non-crystalline, and/or amorphous.

Embodiment 19. The rifaximin delivery composition of any one of embodiments 1 to 18, wherein the first target release beads are configured to release into the upper gastrointestinal tract.

Embodiment 20. The rifaximin delivery composition of any one of embodiments 1 to 19, wherein the first target release beads are configured to release into the first part of the small intestine.

Embodiment 21. The rifaximin delivery composition of any one of embodiments 1 to 20, wherein the second target release beads are configured to release into the mid gastrointestinal tract.

Embodiment 22. A rifaximin composition for use in targeted release comprising a sugar sphere coated with a combination comprising rifaximin, HPMC, and PVP.

Embodiment 23. The rifaximin composition of embodiment 22, wherein the HPMC is present in an amount of from about 5% to about 15% by weight based on the total weight of rifaximin in the combination.

Embodiment 24. The rifaximin composition of embodiment 22 or 23, wherein the HPMC is present in an amount of from about 6% to about 12% by weight based on the total weight of rifaximin in the combination.

Embodiment 25. The rifaximin composition of any one of embodiments 22 to 24, wherein the HPMC is present in an amount of from about 6% to about 10% by weight based on the total weight of rifaximin in the combination.

Embodiment 26. The rifaximin composition of any one of embodiments 22 to 25, wherein the HPMC is present in an amount of from about 6% to about 9% by weight based on the total weight of rifaximin in the combination.

Embodiment 27. The rifaximin composition of any one of embodiments 22 to 26, wherein the HPMC is present in an amount of from about 0.1% to about 2.5% by weight based on the total weight of the composition.

Embodiment 28. The rifaximin composition of any one of embodiments 22 to 27, wherein the HPMC is present in an amount of from about 0.3% to about 2.3% by weight based on the total weight of the composition.

Embodiment 29. The rifaximin composition of any one of embodiments 22 to 28, wherein the HPMC is present in an amount of from about 0.3% to about 0.5% or from about 1.8% to about 2.0% by weight based on the total weight of the composition.

Embodiment 30. The rifaximin composition of any one of embodiments 22 to 29, wherein the HPMC is present in an amount of from about 0.4% to about 0.5% or from about 1.9% to about 2.0% by weight based on the total weight of the composition.

Embodiment 31. The rifaximin composition of any one of embodiments 22 to 30, wherein the PVP is present in an amount of from about 15% to about 35% by weight based on the total weight of rifaximin in the combination.

Embodiment 32. The rifaximin composition of any one of embodiments 22 to 31, wherein the PVP is present in an amount of from about 15% to about 30% by weight based on the total weight of rifaximin in the combination.

Embodiment 33. The rifaximin composition of any one of embodiments 22 to 32, wherein the PVP is present in an amount of from about 20% to about 30% by weight based on the total weight of rifaximin in the combination.

Embodiment 34. The rifaximin composition of any one of embodiments 22 to 33, wherein the PVP is present in an amount of from about 0.5% to about 4.0% or from about 3.0% to about 8.0% by weight based on the total weight of the composition.

Embodiment 35. The rifaximin composition of any one of embodiments 22 to 34, wherein the PVP is present in an amount of from about 0.5% to about 2.0% or from about 4.0% to about 7.0% by weight based on the total weight of the composition.

Embodiment 36. The rifaximin composition of any one of embodiments 22 to 35, wherein the PVP is present in an amount of from about 0.1% to about 2.0% or from about 5.0% to about 6.0% by weight based on the total weight of the composition.

Embodiment 37. The rifaximin composition of any one of embodiments 22 to 36, wherein the combination further comprises a surfactant.

Embodiment 38. The rifaximin composition of any one of embodiments 22 to 37, wherein the combination further comprises a non-ionic surfactant.

Embodiment 39. The rifaximin composition of any one of embodiments 22 to 38, wherein the combination further comprises poloxamer 407.

Embodiment 40. The rifaximin composition of any one of embodiments 37 to 39, wherein the surfactant is present in an amount of from about 5% to about 15% by weight based on the total weight of rifaximin in the composition.

Embodiment 41. The rifaximin composition of any one of embodiments 37 to 40, wherein the surfactant is present in an amount of from about 7% to about 9% by weight based on the total weight of rifaximin in the composition.

Embodiment 42. The rifaximin composition of any one of embodiments 37 to 41, wherein the surfactant is present in an amount of from about 8% to about 9% by weight based on the total weight of rifaximin in the composition.

Embodiment 43. The rifaximin composition of any one of embodiments 22 to 42, wherein the combination comprises crystalline, non-crystalline, and/or amorphous rifaximin.

Embodiment 44. The rifaximin composition of any one of embodiments 22 to 43, wherein the composition further comprises at least one plasticizer and/or at least one agent selected from the group consisting of ascorbyl palmitate, butylated hydroxyanisole (BHA), butylated hydroxytoluene (BHT), citric acid, sodium metabisulfite, cysteine, potassium metabisulfite, propyl gallate, sodium thiosulfate, vitamin E (e.g., Vitamin E TPGS), and 3,4-dihydroxybenzoic acid.

Embodiment 45. The rifaximin composition of embodiment 44, wherein the at least one plasticizer is selected from diethyl phthalate and dibutyl phthalate.

Embodiment 46. The rifaximin composition of embodiment 44 or 45, wherein the at least one plasticizer is diethyl phthalate.

Embodiment 47. The rifaximin composition of any one of embodiments 22 to 46, wherein the rifaximin is present in an amount of from about 1% to about 30% by weight based on the total weight of the composition.

Embodiment 48. The rifaximin composition of any one of embodiments 22 to 47, wherein the rifaximin is present in an amount of from about 1% to about 10% by weight based on the total weight of the composition.

Embodiment 49. The rifaximin composition of any one of embodiments 22 to 48, wherein the rifaximin is present in an amount of from about 4% to about 6% by weight based on the total weight of the composition.

Embodiment 50. The rifaximin composition of any one of embodiments 22 to 47, wherein the rifaximin is present in an amount of from about 15% to about 25% by weight based on the total weight of the composition.

Embodiment 51. The rifaximin composition of any one of embodiments 22 to 47 and 50, wherein the rifaximin is present in an amount of from about 20% to about 23% by weight based on the total weight of the composition.

Embodiment 52. The rifaximin composition of any one of embodiments 22 to 51, wherein the composition is a pH independent release composition.

Embodiment 53. The rifaximin composition of any one of embodiments 22 to 52, wherein the composition is for release into the upper gastrointestinal tract.

Embodiment 54. The rifaximin composition of any one of embodiments 22 to 53, wherein the composition is for release into the first part of the small intestine.

Embodiment 55. A rifaximin composition for use in targeted release comprising a sugar sphere coated with a combination comprising rifaximin and HPMC-AS.

Embodiment 56. The rifaximin composition of embodiment 55, wherein the HPMC-AS is grade M.

Embodiment 57. The rifaximin composition of embodiment 55 or 56, wherein the HPMC-AS is present in an amount of from about 20% to about 60% by weight based on the total weight of rifaximin in the mixture.

Embodiment 58. The rifaximin composition of any one of embodiments 55 to 57, wherein the HPMC-AS is present in an amount of from about 25% to about 50% by weight based on the total weight of rifaximin in the mixture.

Embodiment 59. The rifaximin composition of any one of embodiments 55 to 58, wherein the HPMC-AS is present in an amount of from about 30% to about 47% by weight based on the total weight of rifaximin in the mixture.

Embodiment 60. The rifaximin composition of any one of embodiments 55 to 59, wherein the HPMC-AS is present in an amount of from about 30% to about 45% by weight based on the total weight of rifaximin in the mixture.

Embodiment 61. The rifaximin composition of any one of embodiments 55 to 60, wherein the HPMC-AS is present in an amount of from about 1% to about 4% or from about 8% to about 11% by weight based on the total weight of the composition.

Embodiment 62. The rifaximin composition of any one of embodiments 55 to 61, wherein the HPMC-AS is present in an amount of from about 1% to about 3% or from about 8% to about 10% by weight based on the total weight of the composition.

Embodiment 63. The rifaximin composition of any one of embodiments 55 to 62, wherein the HPMC-AS is present in an amount of from about 2% to about 3% or from about 9% to about 10% by weight based on the total weight of the composition.

Embodiment 64. The rifaximin composition of any one of embodiments 55 to 63, wherein the combination further comprises a surfactant.

Embodiment 65. The rifaximin composition of any one of embodiments 55 to 64, wherein the combination further comprises a non-ionic surfactant.

Embodiment 66. The rifaximin composition of any one of embodiments 55 to 65, wherein the combination further comprises poloxamer 407.

Embodiment 67. The rifaximin composition of any one of embodiments 55 to 66, wherein the surfactant is present in an amount of from about 5% to about 15% by weight based on the total weight of rifaximin in the composition.

Embodiment 68. The rifaximin composition of any one of embodiments 55 to 67, wherein the surfactant is present in an amount of from about 7% to about 9% by weight based on the total weight of rifaximin in the composition.

Embodiment 69. The rifaximin composition of any one of embodiments 55 to 68, wherein the surfactant is present in an amount of from about 8% to about 9% by weight based on the total weight of rifaximin in the composition.

Embodiment 70. The rifaximin composition of any one of embodiments 52 to 69, further comprising at least one pharmaceutically acceptable plasticizer and/or at least one agent selected from the group consisting of ascorbyl palmitate, butylated hydroxyanisole (BHA), butylated hydroxytoluene (BHT), citric acid, sodium metabisulfite, cysteine, potassium metabisulfite, propyl gallate, sodium thiosulfate, vitamin E (e.g., Vitamin E TPGS), and 3,4-dihydroxybenzoic acid.

Embodiment 71. The rifaximin composition of embodiment 70, wherein the at least one pharmaceutically acceptable plasticizer is selected from an alkyl citrate and a phthalate, or a combination thereof.

Embodiment 72. The rifaximin composition of embodiment 70 or 71, wherein the at least one pharmaceutically acceptable plasticizer is selected from triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC, trihexyl o-butyryl citrate), trimethyl citrate (TMC), diethyl phthalate or dibutyl phthalate.

Embodiment 73. The rifaximin composition of any one of embodiments 70 to 72, wherein the at least one pharmaceutically acceptable plasticizer is selected form TEC, diethyl phthalate, diethyl phthalate, or a combination thereof.

Embodiment 74. The rifaximin composition of any one of embodiments 70 to 73, wherein the at least one pharmaceutically acceptable plasticizer is selected form TEC and diethyl phthalate, or a combination thereof.

Embodiment 75. The rifaximin composition of any one of embodiments 70 to 74, wherein the at least one pharmaceutically acceptable plasticizer is TEC.

Embodiment 76. The rifaximin composition of any one of embodiments 70 to 74, wherein the at least one pharmaceutically acceptable plasticizer is a combination of TEC and diethyl phthalate.

Embodiment 77. The rifaximin composition of any one of embodiments 55 to 76, further comprising an enteric coating.

Embodiment 78. The rifaximin composition of any one of embodiments 55 to 77, further comprising an enteric coating around said combination and sugar sphere.

Embodiment 79. The rifaximin composition of embodiment 77 or 78, wherein the enteric coating comprises a methacrylic acid-acrylate copolymer.

Embodiment 80. The rifaximin composition of any one of embodiments 77 to 79, wherein the enteric coating comprises an anionic methacrylic acid-acrylate copolymer.

Embodiment 81. The rifaximin composition of any one of embodiments 77 to 80, wherein the enteric coating comprises copolymers of methacrylic acid and ethylacrylate.

Embodiment 82. The rifaximin composition of any one of embodiments 77 to 81, wherein the enteric coating further comprising an anti-adherent additive.

Embodiment 83. The rifaximin composition of any one of embodiments 55 to 82, wherein the rifaximin is present in an amount of from about 1% to about 30% by weight based on the total weight of the composition.

Embodiment 84. The rifaximin composition of any one of embodiments 55 to 83, wherein the rifaximin is present in an amount of from about 1% to about 10% by weight based on the total weight of the composition.

Embodiment 85. The rifaximin composition of any one of embodiments 55 to 84, wherein the rifaximin is present in an amount of from about 4% to about 6% by weight based on the total weight of the composition.

Embodiment 86. The rifaximin composition of any one of embodiments 55 to 83, wherein the rifaximin is present in an amount of from about 15% to about 25% by weight based on the total weight of the composition.

Embodiment 87. The rifaximin composition of any one of embodiments 55 to 83 and 86, wherein the rifaximin is present in an amount of from about 20% to about 23% by weight based on the total weight of the composition.

Embodiment 88. The rifaximin composition of any one of embodiments 55 to 87, wherein the composition is a pH dependent release composition.

Embodiment 89. The rifaximin targeted release composition of any one of embodiments 55 to 88, wherein the composition is for release into the mid gastrointestinal tract.

Embodiment 90. A composition as described herein, especially a composition of any one of embodiments 1 to 148 or of embodiments 1 to 89, for use in a method of treating one or more disorders in a subject in need thereof, comprising the step of administering to said subject a therapeutically effective amount of the composition.

Embodiment 91. The composition of embodiment 90, wherein the one or more disorders are selected from irritable bowel syndrome (IBS), diarrhea, microbe associated diarrhea, infectious diarrhea, *Clostridium difficile* infections and symptoms, travelers' diarrhea, small intestinal bacterial overgrowth (SIBO), Crohn's disease, sickle-cell disease, diverticular disease, pancreatitis, pancreatic insufficiency, enteritis, colitis, antibiotic associated colitis, hepatic encephalopathy, gastric dyspepsia, cirrhosis, polycystic liver disease, pouchitis, peritonitis, short bowel syndrome, inflammatory bowel disease, rosacea, and *H. pylori* infection.

Embodiment 92. The composition of embodiment 90, wherein the one or more disorders are selected from Parkinson's disease, Alzheimer's disease, autism, and acute myeloid leukemia.

Embodiment 93. The composition of embodiment 90, wherein the one or more disorders are selected from *Clostridium difficile* associated diarrhea, chronic pancreatitis, ulcerative colitis, antibiotic associated colitis, microscopic colitis, and alcoholic cirrhosis.

Embodiment 94. The composition of embodiment 90, wherein the one or more disorders is atherosclerotic cardiovascular disease.

Embodiment 95. The composition of embodiment 90, wherein the one or more disorders is sickle cell disease.

Embodiment 96. A composition as described herein, especially a composition of any one of embodiments 1 to 148 or of embodiments 1 to 89, for use in a method of treating sickle cell disease (SCD) in a patient in need thereof comprising the step of administering to said patient an amount of the composition.

Embodiment 97. A composition as described herein, especially a composition of any one of embodiments 1 to 148 or of embodiments 1 to 89, for use in a method of reducing elevated levels of circulating aged neutrophils (CANs) in a patient in need thereof comprising the step of administering to said patient an amount of the composition.

Embodiment 98. A composition as described herein, especially a composition of any one of embodiments 1 to 148 or of embodiments 1 to 89, for use in a method of treating vaso-occlusive crises (VOCs) in a patient in need thereof comprising the step of administering to said patient an amount of the composition.

Embodiment 99. The composition for use of any one of embodiments 96 to 98, further comprising administering an additional SCD therapeutic agent to the patient.

Embodiment 100. The composition for use of embodiment 99, wherein the additional SCD therapeutic agent comprises hydroxyurea, L-glutamine, hydroxycarbamide, an erythropoietin stimulating agent, an opioid analgesic, or a combination thereof.

Embodiment 101. The composition for use of embodiment 100, wherein the opioid analgesic comprises morphine, codeine, hydrocodone, hydromorphone, methadone, tramadol, oxycodone, tapentadol, fentanyl, or a combination thereof.

Embodiment 102. The composition for use of any one of embodiments 98 to 101, wherein the method of treating vaso-occlusive crises (VOCs) in the patient in need thereof comprises alleviating one or more symptoms of VOCs in the patient.

Embodiment 103. The composition for use of any one of embodiments 98 to 101, wherein the method of treating vaso-occlusive crises (VOCs) in the patient in need thereof comprises reducing or preventing the occurrence of VOCs in the patient.

Embodiment 104. The composition for use of any one of embodiments 98 to 101, wherein the method of treating vaso-occlusive crises (VOCs) in the patient in need thereof comprises reducing the duration or severity of VOCs in the patient.

Embodiment 105. The composition for use of any one of embodiments 98 to 101, wherein the method of treating vaso-occlusive crises (VOCs) in the patient in need thereof comprises mediating or otherwise reducing the patient's opioid usage during VOCs.

Embodiment 106. The composition for use of any one of embodiments 96 to 101, wherein the step of administering to said patient an amount of the composition as described herein, especially a composition of any one of embodiments 1 to 148 or of embodiments 1 to 89, comprises administering a dose of the composition QD, BID, TID, or QID to the patient.

Embodiment 107. The composition for use of any one of embodiments 96 to 101, wherein the step of administering to said patient an amount of the composition as described herein, especially a composition of any one of embodiments 1 to 148 or of embodiments 1 to 89, comprises administering a dose of the composition BID to the patient.

Embodiment 108. The composition for use of any one of embodiments 96 to 101, wherein the step of administering to said patient an amount of the composition as described herein, especially a composition of any one of embodiments 1 to 148 or of embodiments 1 to 89, comprises administering a dose of the composition BID to the patient, wherein the dose comprises about 20, 40, 60, or 80 mg of rifaximin.

Embodiment 109. The composition for use of any one of embodiments 96 to 101, wherein the step of administering to said patient an amount of the composition as described herein, especially a composition of any one of embodiments 1 to 148 or of embodiments 1 to 89, comprises administering about 20, 40, 60, or 80 mg of rifaximin provided in an ER bead formulation.

Embodiment 110. The composition for use of any one of embodiments 96 to 101, wherein the step of administering to said patient an amount of the composition as described herein, especially a composition of any one of embodiments 1 to 148 or of embodiments 1 to 89, comprises administering about 20, 40, 60, or 80 mg of rifaximin provided in an DER bead formulation.

Embodiment 111. A composition, especially a composition as described herein, preferably a composition of any one of embodiments 1 to 148 or of embodiments 1 to 89, for use in targeted release to the upper, mid-, or lower gastrointestinal tract, comprising a sugar sphere encapsulated with a combination comprising a poorly soluble therapeutic compound layered with at least one pH independent or pH dependent polymer, or both as defined herein.

The invention claimed is:

1. A rifaximin bead composition comprising a plurality of sugar spheres coated with rifaximin and a combination of hydroxypropyl methylcellulose (HPMC) and polyvinylpyrrolidone (PVP);

wherein:

HPMC is present in an amount of from about 5% to about 15% by weight based on the total weight of rifaximin in the composition or from about 0.1% to about 2.5% by weight based on the total weight of the composition, and PVP is present in an amount of from about 15% to about 35% by weight based on the total weight of rifaximin in the composition, or from about 0.5% to about 4.0%, or from about 3.0% to about 8.0% by weight based on the total weight of the composition.

2. The rifaximin bead composition of claim 1, wherein HPMC is present in an amount of from about 5% to about 15% by weight based on the total weight of rifaximin in the composition.

3. The rifaximin bead composition of claim 1, wherein PVP is present in an amount of from about 15% to about 35% by weight based on the total weight of rifaximin in the composition.

4. The rifaximin bead composition of claim 1, further comprising a surfactant.

5. The rifaximin bead composition of claim 1, wherein the rifaximin is present in an amount of from about 1% to about 30% by weight based on the total weight of the composition.

6. A method of treating one or more disorders in a subject in need thereof, comprising the step of administering to said subject a therapeutically effective amount of the composition of claim 1, wherein the one or more disorders are selected from irritable bowel syndrome (IBS), diarrhea, microbe associated diarrhea, infectious diarrhea, *Clostridium difficile* infections and symptoms, travelers' diarrhea, small intestinal bacterial overgrowth (SIBO), Crohn's disease, sickle-cell disease, diverticular disease, pancreatitis, pancreatic insufficiency, enteritis, colitis, antibiotic associated colitis, hepatic encephalopathy, gastric dyspepsia, cirrhosis, polycystic liver disease, pouchitis, peritonitis, short bowel syndrome, inflammatory bowel disease, rosacea, and *H. pylori* infection.

* * * * *